(12) United States Patent
Piddington et al.

(10) Patent No.: US 6,531,576 B1
(45) Date of Patent: Mar. 11, 2003

(54) FOUR-HELICAL BUNDLE PROTEIN ZSIG81

(75) Inventors: Christopher S. Piddington, Thousand Oaks, CA (US); James W. West, Seattle, WA (US); Richard D. Holly, Seattle, WA (US); Steven K. Burkhead, Hershey, PA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/585,228

(22) Filed: Jun. 1, 2000

Related U.S. Application Data

(60) Provisional application No. 60/137,057, filed on Jun. 1, 1999.

(51) Int. Cl.[7] ................. C07K 14/475; C07K 14/47
(52) U.S. Cl. ....................................... 530/350
(58) Field of Search .................. 530/350, 300, 530/326, 328; 514/12, 14, 15

(56) References Cited

PUBLICATIONS

Bowie et al. Deciphering the message in protein sequences: tolerance to amino acid substitutions. Science, (Mar. 16, 1990) 247 (4948) 1306–10.*
Ngo et al., in The Protein Folding Problem and Tertiary Structure Prediction, Merz and Le Grand (Eds), August 1994, Springer Verlag, pp. 433 and 492–495.*
Incyte Pharmaceuticals, Inc. EST, INC1209538, 1996.
Incyte Pharmaceuticals, Inc. EST, INC1209224, 1996.
Genbank Acc. No. AA501097, EST1145727, 1997.
Incyte Pharmaceuticals, Inc. EST, INC3347129, 1997.
Genbank Acc. No. A104519567, 1998.
Incyte Pharmaceuticals, Inc. EST, INC4922572, 1998.
Incyte Pharmaceuticals, Inc. EST, INC4883838H2, 1998.
Incyte Pharmaceuticals, Inc. EST, INC4883096, 1998.
Genbank Acc. No. AW482402, EST3893275, 2000.
Incyte Pharmaceuticals, Inc. EST, INC7081907, 2000.

* cited by examiner

*Primary Examiner*—David S. Romeo
(74) *Attorney, Agent, or Firm*—Deborah A. Sawislak

(57) ABSTRACT

This present invention is directed to polypeptide and polynucleotide molecules that encode a four-helical bundle cytokine. The cytokine has been designated zsig81, and has restricted expression in primarily heart, lung and liver. zsig81 has been shown to stimulate proliferation of hematopoietic cells and will be useful expansion of these cells, as well as conditions associated with hematopoietic cells. The invention is directed to antibodies and methods of making zsig81 polypeptides, as well.

9 Claims, 4 Drawing Sheets

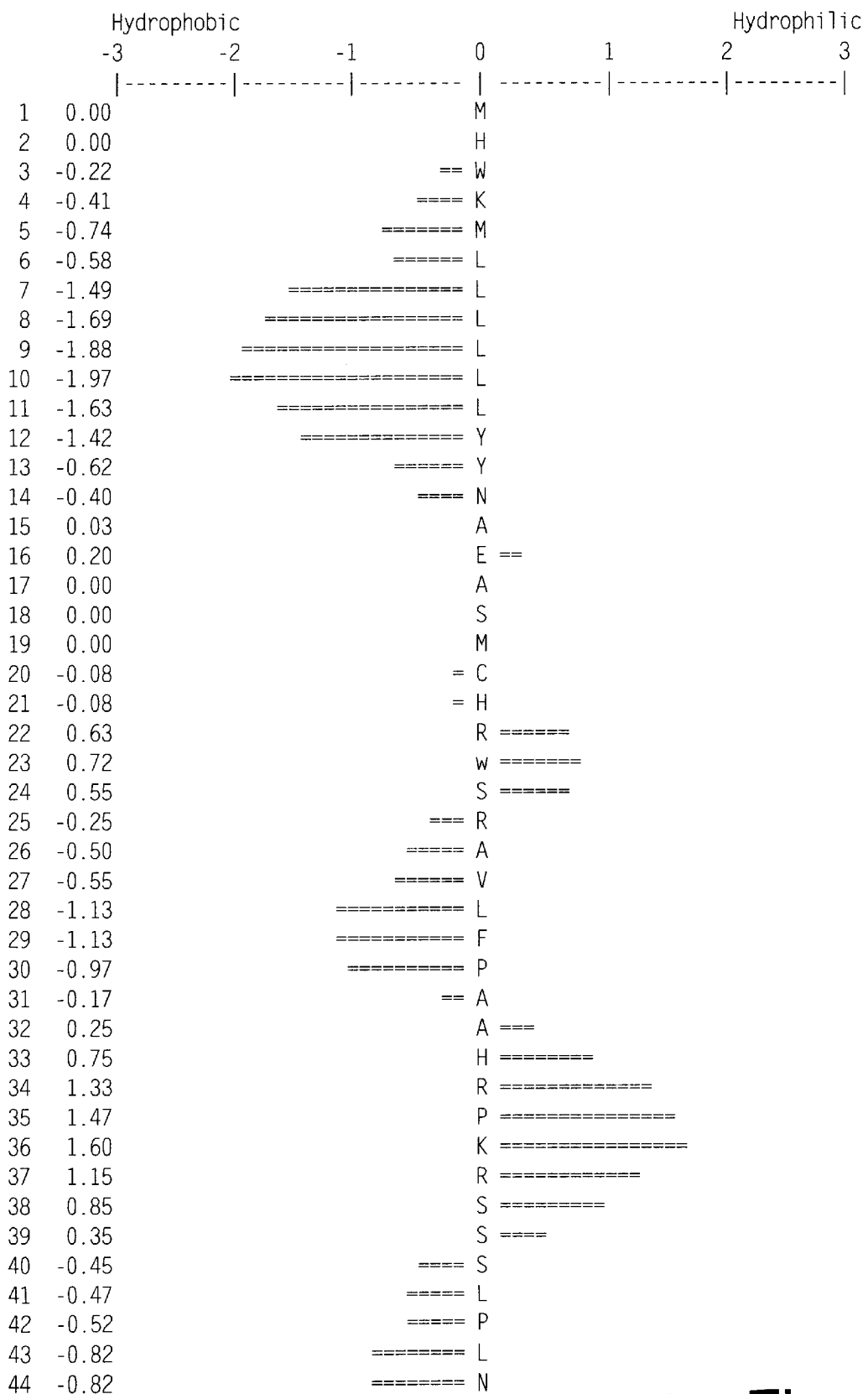
The Figure

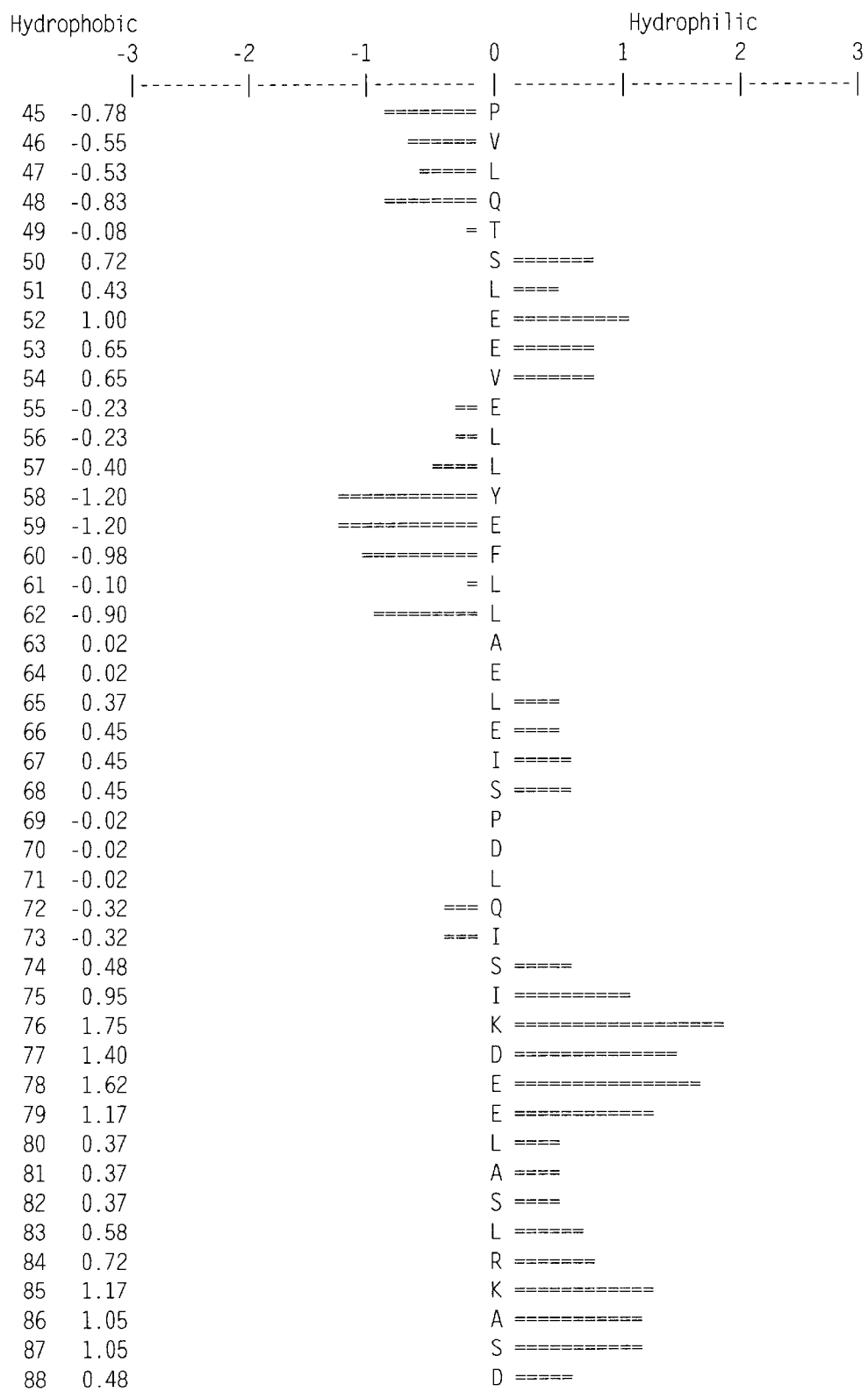
The Figure (continued)

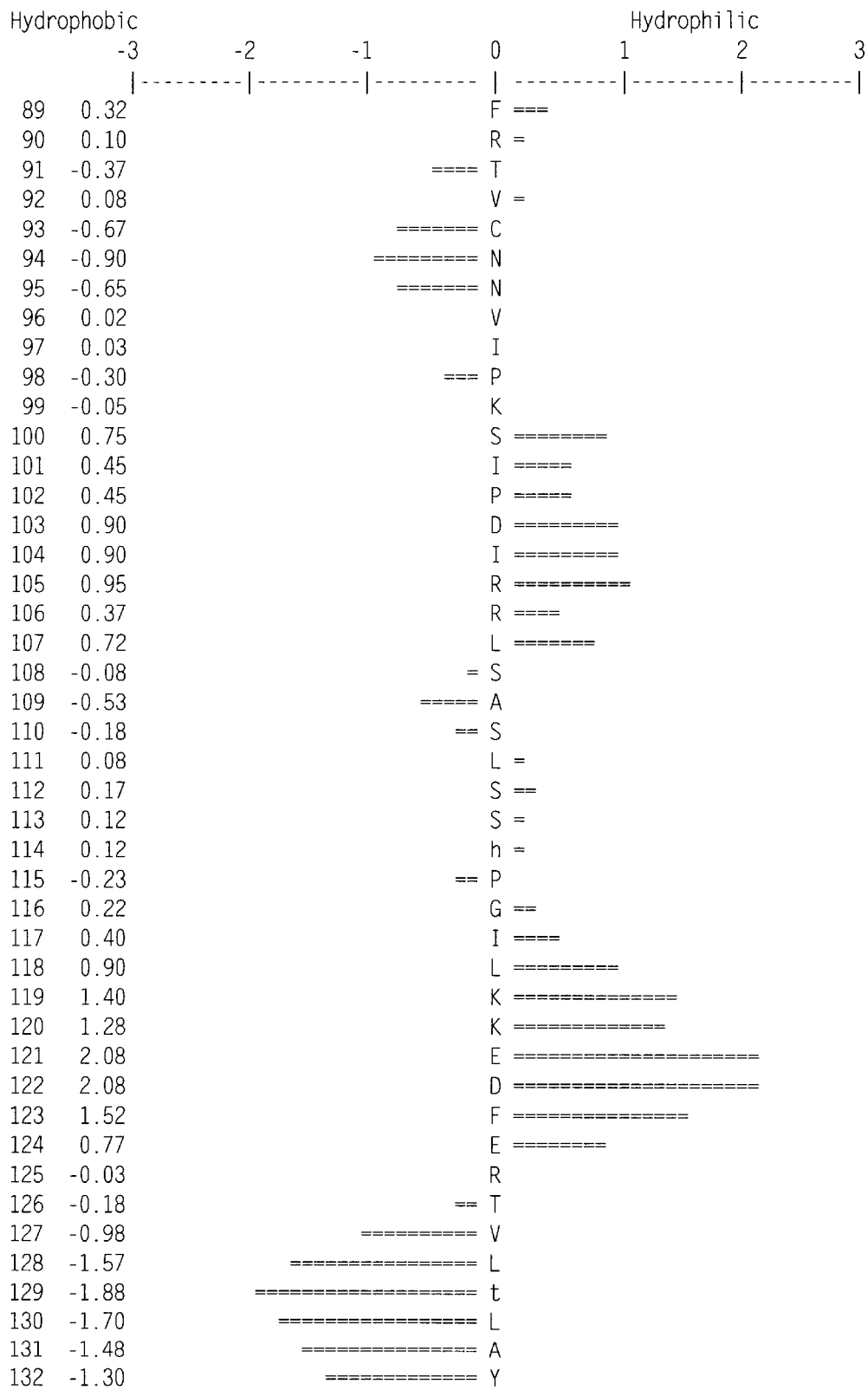
The Figure (continued)

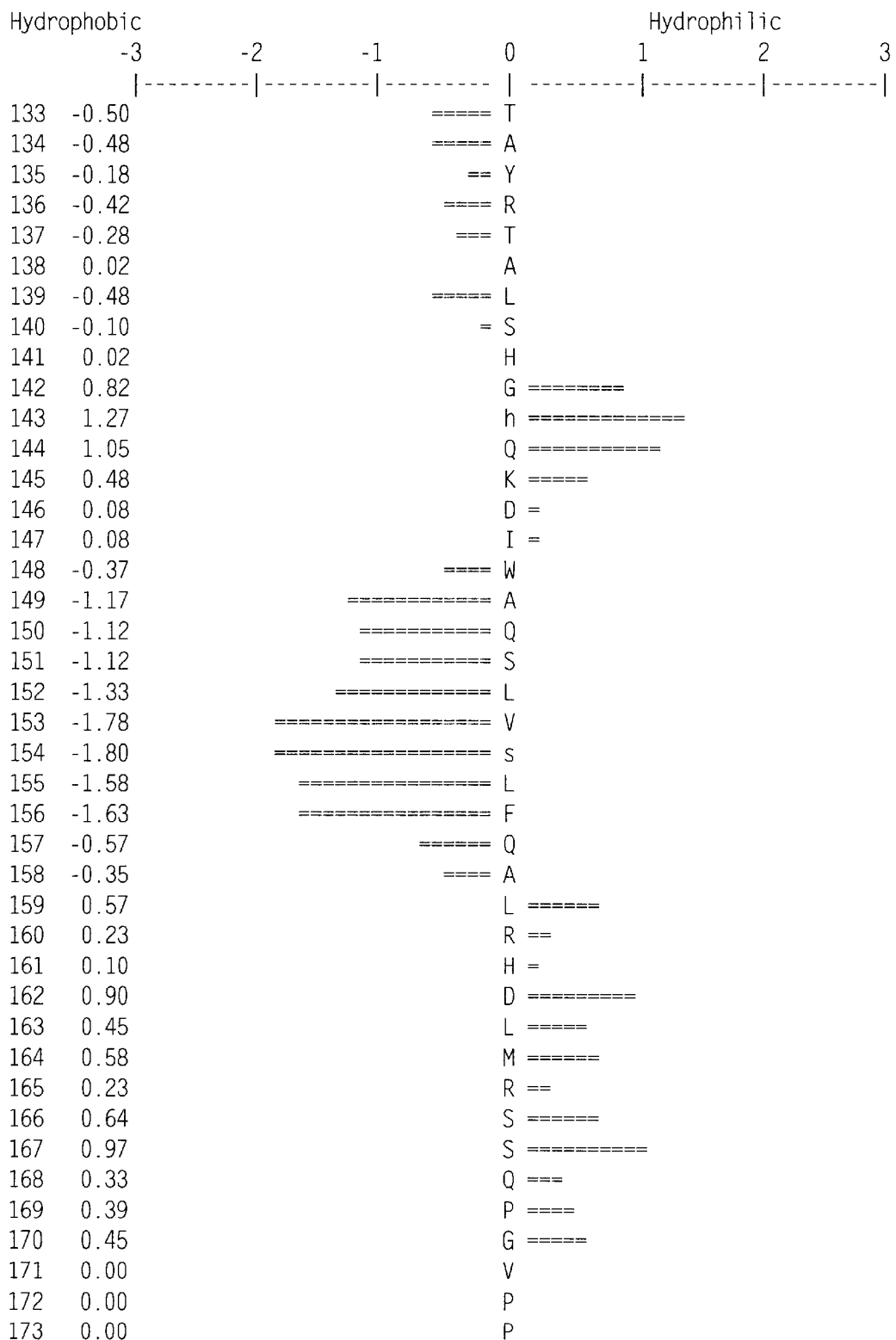
The Figure (concluded)

FOUR-HELICAL BUNDLE PROTEIN ZSIG81

REFERENCE TO RELATED APPLICATIONS

This application is related to Provisional Application No. 60/137,057, filed on Jun. 1, 1999. Under 35 U.S.C. §119(e) (1), this application claims benefit of said Provisional Application.

BACKGROUND OF THE INVENTION

Cellular differentiation of multicellular organisms is controlled by hormones and polypeptide growth factors. These diffusable molecules allow cells to communicate with each other and act in concert to form tissues and organs, and to repair and regenerate damaged tissue. Examples of hormones and growth factors include the steroid hormones, parathyroid hormone, follicle stimulating hormone, the interferons, the interleukins, platelet derived growth factor, epidermal growth factor, and granulocyte-macrophage colony stimulating factor, among others.

Hormones and growth factors influence cellular metabolism by binding to receptor proteins. Certain receptors are integral membrane proteins that bind with the hormone or growth factor outside the cell, and that are linked to signaling pathways within the cell, such as second messenger systems. Other classes of receptors are soluble intracellular molecules.

In general, there is conservation among the cytokine receptors, which are classified into two classes. The cytokine ligands for these receptors have some conserved structural identity, as well, however, the biological activity of these ligands is diverse. The molecules of the present invention belong to a structural class of ligands that is characterized by comprising a four-helical bundle. As a group, the cytokine family of ligands have been extremely valuable as therapeutics and reagents for understanding the growth and maturation of many cell types. The cells influenced by cytokines range from totipotent stem cells to terminally differentiated cells with specialized functions critical to homeostasis of a broad spectrum of living systems. Thus, based on the activities of the cytokine family of proteins there is a need for new cytokines, cytokine agonists and cytokine antagonists, as well as related compounds and methods. The present invention provides such polypeptides for these and other uses that should be apparent to those skilled in the art from the teachings herein.

BRIEF DESCRIPTION OF THE DRAWINGS

The FIGURE illustrates a Hopps Woods Hydrophobicity Plot.

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952–4, 1985), substance P, Flag™ peptide (Hopp et al., *Biotechnology* 6:1204–10, 1988), streptavidin binding peptide, or other antigenic epitope or binding domain. See, in general, Ford et al., *Protein Expression and Purification* 2: 95–107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" denotes a polynucleotide molecule having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of a novel DNA sequence that encodes a four-helical bundle cytokine. The family of four-helical bundle cytokines is described herein and the polynucleotides and polypeptides of the present invention will comprise some or all of the components characterizing the protein family. The polypeptides of the present invention have been designated zsig81.

Sequence analysis revealed an open reading frame of 173 amino acids, with a secretory signal peptide of 17 amino acids at the N-terminus and a mature protein of 156 amino acids. Based on N-terminal sequence analysis of recombinantly expressed human protein, cleavage after residue 4 (His) results in a biologically active molecule of 151 amino acids as shown in SEQ ID NO: 2 from residue 5 (Arg) to residue 156 (Pro). Four-helical cytokine polypeptides generally have a strong signal sequence with a proximal upstream stop codon. In the molecules of the present invention, the human zsig81 encodes a stop codon beginning at nucleotide −30 as shown in SEQ ID NO: 1. The corresponding nucleotide in the mouse ortholog of zsig81 can be found at nucleotide −27 of SEQ ID NO: 3. Those skilled in the art will recognize, however, that some cytokines (e.g., endothelial cell growth factor, basic FGF, and IL-1β) do not comprise conventional secretory peptides and are secreted by a mechanism that is not understood. The cDNA also includes a clear polyadenylation signal, as well as two message instability motifs (ATTTA) in the 3'-untranslated region. These message instability motifs are characteristic of cytokine genes (Shaw and Kamen, *Cell* 46:659–667, 1986).

In general, cytokines are predicted to have a four-alpha helix structure, with helices A, C and D being most important in ligand-receptor interactions, containing conserved motifs among members of the family. The four helices, designated A, B, C, and D have been predicted to span amino acid residues 30 to 44 (helix A), 56–70 (helix B), 86–94 (helix C) and 135–149 (helix D), as shown in SEQ ID NO: 2. Helix C boundaries are predicted to either span residues 80–94 or 86–100 of SEQ ID NO: 2. A structural analysis indicates that the loop structure of zsig81 conforms with other members of the cytokine family in that the A/B loop is long, the B/C loop is short, and the C/D loop is long. This loop structure results in an up-up-down-down helical organization, typical of cytokines. Therefore, the predicted helical structure of zsig81 would include the molecule in the family of short-helix form cytokines with IL-2, IL-4, IL-5, and GM-CSF. Studies using CNTF and IL-6 demonstrated that a CNTF helix can be exchanged for the equivalent helix in IL-6, conferring CTNF-binding properties to the chimera. Thus, it appears that functional domains of four-helical cytokines are determined on the basis of structural homology, irrespective of sequence identity, and can maintain functional integrity in a chimera (Kallen et al., *J. Biol. Chem.* 274:11859–11867, 1999). Therefore, the helical domains of zsig81 will be useful for preparing chimeric fusion molecules, particularly with other short-helix form cytokines to determine and modulate receptor binding specificity. Of particular interest are fusion proteins engineered with helix A and/or helix D, and fusion proteins that combine helical and loop domains from other short-form cytokines such as IL-2, IL-4, IL-15 and GM-CSF. In the amino acid sequence N-terminal to helix A and C-terminal to the secretory signal sequence, there is a proline-rich region. C-terminal to helix D, the amino acid sequence forms a short tail spanning residues 150 to 156. Within the helical regions, residues that are expected to lie within the core of the four-helix bundle occur at residues 30, 33, 34, 37, 40, 41, 44, 56, 59, 60, 63, 66, 67, 70, 80, 83, 84, 87, 90, 91, 94, 135, 138, 139, 142, 145, 146, and 149.

Zsig81 has two Cysteine residues, located at residue 3, which is N-terminal to loop A/B, and at residue 76, which is located in the B/C loop. However, when protein that has been expressed in baculovirus is N-terminally sequenced, the biologically active molecule is a heterogeneous mixture with a significant portion of the protein cleaved after His4, thereby resulting in a molecule with a single cysteine at residue 76. In the mature zsig81 molecule, the two cysteines may form an intramolecular disulfide bond; and in the N-terminally truncated molecule or mature molecule, a single cysteine may form homodimers or heterodimers with another binding partner. Using SDS-PAGE analysis, a homodimeric form of zsig81 protein has been detected. Based on analysis of amino acid charges, the helix A is negatively charged and the C helix is positively charged. The predicted molecular weight of zsig81 is 17,533 Daltons, and there is no apparent glycosylation.

Analysis of the tissue distribution of the human mRNA corresponding to this novel DNA showed that expression was found to be restricted to heart and liver. Within the heart tissue, the highest expression of human mRNA has been localized to the smooth muscle of aorta. While the cDNA is predicted to be approximately 1.7 kb in size, bands identified on Northerns were approximately 5.0 kb. A splice variant containing approximately 2.5 kb 3' untranslated region was identified in human zsig81 mRNA, and is believed to correspond to the 5.0 kb band seen by Northern analysis.

The ortholog from mouse has also been identified and designated zsig81 m. A DNA sequence and corresponding putative amino acid sequence are shown in SEQ ID NOS: 3 and 4, respectively.

SEQ ID NO: 5 is a degenerate polynucleotide sequence that encompasses all polynucleotides that could encode the zsig81 polypeptide of SEQ ID NO: 2 (amino acids 1 or 24 to 354). Thus, zsig81 polypeptide-encoding polynucleotides ranging from nucleotide 134 or 185 to nucleotide 655 of SEQ ID NO: 2 or nucleotide 1 or 52 to 519 of SEQ ID NO: 5 are contemplated by the present invention. Also contemplated by the present invention are fragments and fusions as described herein with respect to SEQ ID NO: 1, which are formed from analogous regions of SEQ ID NO: 5, wherein nucleotides 134 to 184 of SEQ ID NO: 1 correspond to nucleotides 1 to 51 of SEQ ID NO: 5, for the secretory signal sequence; wherein nucleotides 272 to 316 of SEQ ID NO: 1 correspond to nucleotides 139 to 183 of SEQ ID NO: 5, for helix A; wherein nucleotides 350 to 394 of SEQ ID NO: 1 correspond to nucleotides 216 to 261 of SEQ ID NO: 5 for helix B; wherein nucleotides 440 to 466 of SEQ ID NO: 1 correspond to nucleotides 307 to 331 of SEQ ID NO: 5, for helix C; and wherein nucleotide 587 to nucleotide 631 of SEQ ID NO: 1 correspond to nucleotide 454 to nucleotide 499 of SEQ ID NO: 5 for helix D. Table 1 sets forth the one-letter codes used within SEQ ID NO: 5 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Resolution |
| --- | --- | --- | --- |
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NOS: 2 and 4, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NOS: 2 and 4. Variant sequences can be readily tested for functionality as described herein.

One of ordinary skill in the art will also appreciate that different species can exhibit "preferential codon usage." In general, see, Grantham, et al., Nuc. Acids Res., 8:1893–912, 1980; Haas, et al. Curr. Biol., 6:315–24, 1996; Wain-Hobson, et al., Gene, 13:355–64, 1981; Grosjean and Fiers, Gene, 18:199–209, 1982; Holm, Nuc. Acids Res., 14:3075–87, 1986; Ikemura, J. Mol. Biol., 158:573–97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO: 5 serves as a template for optimizing expression of polynucleotides in various cell types and species commonly used in the art and disclosed herein. Sequences containing preferential codons can be tested and optimized for expression in various species, and tested for functionality as disclosed herein.

The present invention further provides variant polypeptides and nucleic acid molecules that represent counterparts from other species (orthologs). These species include, but are not limited to mammalian, avian, amphibian, reptile, fish, insect and other vertebrate and invertebrate species. Of particular interest are zsig81 polypeptides from other mammalian species, including murine, porcine, ovine, bovine, canine, feline, equine, and other primate polypeptides. Orthologs of human zsig81 can be cloned using information and compositions provided by the present invention in combination with conventional cloning techniques. For example, a cDNA can be cloned using mRNA obtained from a tissue or cell type that expresses zsig81 as disclosed herein. Suitable sources of mRNA can be identified by probing northern blots with probes designed from the sequences disclosed herein. A library is then prepared from mRNA of a positive tissue or cell line. The mouse sequence zsig81 is a representative ortholog of the human zsig81, and is disclosed herein as SEQ ID NOS:3 and 4.

An zsig81-encoding cDNA can then be isolated by a variety of methods, such as by probing with a complete or partial human cDNA or with one or more sets of degenerate probes based on the disclosed sequences. A cDNA can also be cloned using the polymerase chain reaction with primers designed from the representative human zsig81 sequences disclosed herein. Within an additional method, the cDNA library can be used to transform or transfect host cells, and expression of the cDNA of interest can be detected with an antibody to zsig81 polypeptide. Similar techniques can also be applied to the isolation of genomnic clones.

The present invention provides polynucleotide molecules including DNA and RNA molecules that encode the zsig81 polypeptides disclosed above.

Zsig81 polynucleotide sequences disclosed herein can also be used as probes or primers to clone 5' non-coding regions of a zsig81 gene. In view of the tissue-specific expression observed for zsig81 by Northern blotting, this gene region is expected to provide for heart- and liver-specific expression. Promoter elements from a zsig81 gene could thus be used to direct the tissue-specific expression of heterologous genes in, for example, transgenic animals or patients treated with gene therapy. Cloning of 5' flanking sequences also facilitates production of zsig81 proteins by "gene activation" as disclosed in U.S. Pat. No. 5,641,670. Briefly, expression of an endogenous zsig81 gene in a cell is altered by introducing into the zsig81 locus a DNA construct comprising at least a targeting sequence, a regulatory sequence, an exon, and an unpaired splice donor site. The targeting sequence is a zsig81 5' non-coding sequence that permits homologous recombination of the construct with the endogenous zsig81 locus, whereby the sequences within the construct become operably linked with the endogenous zsig81 coding sequence. In this way, an endogenous zsig81 promoter can be replaced or supplemented with other regulatory sequences to provide enhanced, tissue-specific, or otherwise regulated expression.

Those skilled in the art will recognize that the sequence disclosed in SEQ ID NO: 1 represents a single allele of human zsig81 and that allelic variation and alternative splicing are expected to occur. Allelic variants of this sequence can be cloned by probing cDNA or genomic libraries from different individuals according to standard procedures. Allelic variants of the nucleotide sequence shown in SEQ ID NO: 1, including those containing silent mutations and those in which mutations result in amino acid sequence changes, are within the scope of the present invention, as are proteins which are allelic variants of SEQ ID NO:2. cDNA molecules generated from alternatively spliced mRNAs, which retain the properties of the zsig81 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

Analysis of chromosomal DNA using the zsig81 polynucleotide sequence is useful for correlating disease with abnormalities localized to chromosome 7. The human zsig81 gene has been localized to chromosome 7q32-q33. Use as a diagnostic could assist physicians in determining the type of disease and appropriate associated therapy, or could assist in genetic counseling. As such, the inventive anti-zsig81 antibodies, polynucleotides, and polypeptides can be used for the detection of zsig81 polypeptide, mRNA or anti-zsig81 antibodies, thus serving as markers and be directly used for detecting genetic diseases or cancers, as described herein, using methods known in the art and described herein. Further, zsig81 polynucleotide probes can be used to detect abnormalities involving chromosome 7q32-q33 as described herein. These abnormalities may be associated with human diseases, or tumorigenesis, spontaneous abortion or other genetic disorders. Thus, zsig81 polynucleotide probes can be used to detect abnormalities or genotypes associated with these defects.

As discussed above, defects in the zsig81 gene itself may result in a heritable human disease state. Molecules of the present invention, such as the polypeptides, antagonists, agonists, polynucleotides and antibodies of the present invention would aid in the detection, diagnosis prevention, and treatment of diseases associated with a zsig81 genetic defect. In addition, zsig81 polynucleotide probes can be used to detect allelic differences between diseased or non-diseased individuals at the zsig81 chromosomal locus. As such, the zsig81 sequences can be used as diagnostics in forensic DNA profiling.

In general, the diagnostic methods used in genetic linkage analysis, to detect a genetic abnormality or aberration in a patient, are known in the art. Most diagnostic methods comprise the steps of (i) obtaining a genetic sample from a potentially diseased patient, diseased patient or potential non-diseased carrier of a recessive disease allele; (ii) producing a first reaction product by incubating the genetic sample with a zsig81 polynucleotide probe wherein the polynucleotide will hybridize to complementary polynucleotide sequence, such as in RFLP analysis or by incubating the genetic sample with sense and antisense primers in a PCR reaction under appropriate PCR reaction conditions; (iii) Visualizing the first reaction product by gel electrophoresis and/or other known method such as visualizing the first reaction product with a zsig81 polynucleotide probe wherein the polynucleotide will hybridize to the complementary polynucleotide sequence of the first reaction; and (iv) comparing the visualized first reaction product to a second control reaction product of a genetic sample from a normal or control individual. A difference between the first reaction product and the control reaction product is indicative of a genetic abnormality in the diseased or potentially diseased patient, or the presence of a heterozygous recessive carrier phenotype for a non-diseased patient, or the presence of a genetic defect in a tumor from a diseased patient, or the presence of a genetic abnormality in a fetus or pre-implantation embryo. For example, a difference in restriction fragment pattern, length of PCR products, length of repetitive sequences at the zsig81 genetic locus, and the like, are indicative of a genetic abnormality, genetic aberration, or allelic difference in comparison to the normal control. Controls can be from unaffected family members, or unrelated individuals, depending on the test and availability of samples. Genetic samples for use within the present invention include genomic DNA, mRNA, and cDNA isolated from any tissue or other biological sample from a patient, such as but not limited to, blood, saliva, semen, embryonic cells, amniotic fluid, and the like. The polynucleotide probe or primer can be RNA or DNA, and will comprise a portion of SEQ ID NO: 1, the complement of SEQ ID NO: 1, or an RNA equivalent thereof. Such methods of showing genetic linkage analysis to human disease phenotypes are well known in the art. For reference to PCR based methods in diagnostics see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)).

Mutations associated with the zsig81 locus can be detected using nucleic acid molecules of the present invention by employing standard methods for direct mutation analysis, such as restriction fragment length polymorphism analysis, short tandem repeat analysis employing PCR techniques, amplification-refractory mutation system analysis, single-strand conformation polymorphism detection, RNase cleavage methods, denaturing gradient gel electrophoresis, fluorescence-assisted mismatch analysis, and other genetic analysis techniques known in the art (see, for example, Mathew (ed.), *Protocols in Human Molecular Genetics* (Humana Press, Inc. 1991), Marian, *Chest* 108:255 (1995), Coleman and Tsongalis, *Molecular Diagnostics* (Human Press, Inc. 1996), Elles (ed.) *Molecular Diagnosis of Genetic Diseases* (Humana Press, Inc. 1996), Landegren (ed.), *Laboratory Protocols for Mutation Detection* (Oxford University Press 1996), Birren et al. (eds.), *Genome Analysis, Vol. 2: Detecting Genes* (Cold Spring Harbor Laboratory Press 1998), Dracopoli et al. (eds.), *Current Protocols in Human Genetics* (John Wiley & Sons 1998), and Richards and Ward, "Molecular Diagnostic Testing," in *Principles of Molecular Medicine*, pages 83–88 (Humana Press, Inc. 1998). Direct analysis of an zsig81 gene for a mutation can be performed using a subject's genomic DNA. Methods for amplifying genomic DNA, obtained for example from peripheral blood lymphocytes, are well-known to those of skill in the art (see, for example, Dracopoli et al. (eds.), *Current Protocols in Human Genetics*, at pages 7.1.6 to 7.1.7 (John Wiley & Sons 1998)).

Positions of introns in the mouse zsig81 gene were determined by identification of genotnic clones, followed by sequencing the intron/exon junctions. The coding regions for the zsig81 molecule are contained in three exons. The first intron junction lies between amino acid residue 8 (Arg) and residue 9 (Ala) in Seq. ID. No. 4. The second intron junction lies between amino acid residue 42 (Glu) and residue 43 (Leu) in Seq. ID. No. 4. The third intron contains the remaining DNA encoding for the C-terminal portion of the molecule, as well as a 3' untranslated region.

Within an embodiment of the invention, the isolated nucleic acid molecules can hybridize under stringent conditions to nucleic acid molecules having the nucleotide sequence of SEQ ID NO: 1 from nucleotide 134 or 185 to 655, or the full length sequence, to nucleic acid molecules having a nucleotide sequence complementary to SEQ ID NO: 1. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe.

A pair of nucleic acid molecules, such as DNA-DNA, RNA-RNA and DNA-RNA, can hybridize if the nucleotide sequences have some degree of complementarity. Hybrids can tolerate mismatched base pairs in the double helix, but the stability of the hybrid is influenced by the degree of mismatch. The $T_m$ of the mismatched hybrid decreases by 1° C. for every 1–1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases.

It is well within the abilities of one skilled in the art to adapt these conditions for use with a particular polynucleotide hybrid. The $T_m$ for a specific target sequence is the temperature (under defined conditions) at which 50% of the target sequence will hybridize to a perfectly matched probe sequence. Those conditions which influence the $T_m$ include, the size and base pair content of the polynucleotide probe, the ionic strength of the hybridization solution, and the presence of destabilizing agents in the hybridization solution. Numerous equations for calculating $T_m$ are known in the art, and are specific for DNA, RNA and DNA-RNA hybrids and polynucleotide probe sequences of varying length (see, for example, Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and *Primer Premier* 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences, >50 base pairs, is performed at temperatures of about 20–25° C. below the calculated $T_m$. For smaller probes, <50 base pairs, hybridization is typically carried out at the $T_m$ or 5–10° C. below the calculated $T_m$. This allows for the maximum rate of hybridization for DNA-DNA and DNA-RNA hybrids.

Following hybridization, the nucleic acid molecules can be washed to remove non-hybridized nucleic acid molecules under stringent conditions, or under highly stringent conditions. Typical stringent washing conditions include washing in a solution of 0.5×–2×SSC with 0.1% sodium dodecyl sulfate (SDS) at 55–65° C. That is, nucleic acid molecules encoding a variant zsig81 polypeptide hybridize with a nucleic acid molecule having the nucleotide sequence of SEQ ID NO: 1 (or its complement) under stringent washing conditions, in which the wash stringency is equivalent to 0.5×–2×SSC with 0.1% SDS at 55–65° C., including 0.5× SSC with 0.1% SDS at 55° C., or 2×SSC with 0.1% SDS at 65° C. One of skill in the art can readily devise equivalent conditions, for example, by substituting SSPE for SSC in the wash solution.

Typical highly stringent washing conditions include washing in a solution of 0.1×0.2×SSC with 0.1% sodium dodecyl sulfate (SDS) at 50–65° C. In other words, nucleic acid molecules encoding a variant zsig81 polypeptide hybridize with a nucleic acid molecule having the nucleotide sequence of SEQ ID NO:1 (or its complement) under highly stringent washing conditions, in which the wash stringency is equivalent to 0.1×–0.2×SSC with 0.1% SDS at 50–65° C., including 0.1×SSC with 0.1% SDS at 50° C., or 0.2×SSC with 0.1% SDS at 65° C.

The present invention also provides isolated zsig81 polypeptides that have a substantially similar sequence identity to the polypeptides of SEQ ID NO:2, or their orthologs. The term "substantially similar sequence identity" is used herein to denote polypeptides comprising at least 70% to 80%, and in certain embodiments at least 90% to 95%, or in other embodiments greater than 95% sequence identity to the sequences shown in SEQ ID NO:2, or their orthologs. The present invention also includes polypeptides that comprise an amino acid sequence having at least 70% to 80%, and in certain embodiments at least 90% to 95%, or in other embodiments greater than 95% sequence identity to the sequence of amino acid residues 1 or 24 to 354 of SEQ ID NO:2. The present invention further includes nucleic acid molecules that encode such polypeptides. Methods for determining percent identity are described below.

The present invention also contemplates zsig81 variant nucleic acid molecules that can be identified using two criteria: a determination of the similarity between the encoded polypeptide with the amino acid sequence of SEQ ID NO:2, and/or a hybridization assay, as described above. Such zsig81 variants include nucleic acid molecules (1) that hybridize with a nucleic acid molecule having the nucleotide sequence of SEQ ID NO:1 (or its complement) under stringent washing conditions, in which the wash stringency is equivalent to 0.5×–2×SSC with 0.1% SDS at 55–65° C., or (2) that encode a polypeptide having at least 70%, at least 80%, at least 90%, at least 95% or greater than 95% sequence identity to the amino acid sequence of SEQ ID NO:2. Alternatively, zsig81 variants can be characterized as nucleic acid molecules (1) that hybridize with a nucleic acid molecule having the nucleotide sequence of SEQ ID NO:1 (or its complement) under highly stringent washing conditions, in which the wash stringency is equivalent to 0.1×0.2×SSC with 0.1% SDS at 50–65° C., and (2) that encode a polypeptide having at least 70% to 80%, and in certain embodiments at least 90% to 95%, or in other embodiments greater than 95% sequence identity to the amino acid sequence of SEQ ID NO:2.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 3 (amino acids are indicated by the standard one-letter codes).

$$\frac{\text{Total number of identical matches}}{[\text{length of the longer sequence plus the number of gaps introduced into the longer sequence in order to align the two sequences}]} \times 100$$

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant zsig81. The FASTA algorithm is described by Pearson and Lipman, *Proc. Nat'l Acad. Sci. USA* 85:2444 (1988), and by Pearson, *Meth. Enzymol.* 183:63 (1990).

Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from four to six.

Variant zsig81 polypeptides or polypeptides with substantially similar sequence identity are characterized as having one or more amino acid substitutions, deletions or additions. These changes are preferably of a minor nature, that is conservative amino acid substitutions (see Table 4) and other substitutions that do not significantly affect the folding or activity of the polypeptide; small deletions, typically of one to about 30 amino acids; and amino- or carboxyl-terminal extensions, such as an amino-terminal methionine residue, a small linker peptide of up to about 20–25 residues, or an affinity tag. The present invention thus includes polypeptides of from about 28 to 354 amino acid residues that comprise a sequence that is at least 70% to 80%, and in certain embodiments at least 90% to 95%, or in other embodiments greater than 95% or more identical to the corresponding region of SEQ ID NO:2. In particular, peptides and polypeptides corresponding to regions of the zsig81 molecules as shown in SEQ ID NO: 2 include the helix A (residues 30–44), helix B (residues 56–70), helix C (comprising residues 86–94) and helix D (residues 135–149) are within the scope of the present invention. Polypeptides comprising affinity tags can further comprise a proteolytic cleavage site between the zsig81 polypeptide and the affinity tag. Preferred such sites include thrombin cleavage sites and factor Xa cleavage sites.

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

TABLE 4

Conservative amino acid substitutions

| Basic: | arginine |
| | lysine |
| | histidine |
| Acidic: | glutamic acid |
| | aspartic acid |
| Polar: | glutamine |
| | asparagine |

TABLE 4-continued

Conservative amino acid substitutions

| | |
|---|---|
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., *J. Am. Chem. Soc.* 113:2722 (1991), Ellman et al., *Methods Enzymol.* 202:301 (1991), Chung et al., *Science* 259:806 (1993), and Chung et al., *Proc. Nat'l Acad. Sci. USA* 90:10145 (1993).

In a second method, translation is carried out in Xenopus oocytes by microinjection of mutated mRNA and chemically aminoacylated suppressor tRNAs (Turcatti et al., *J. Biol. Chem.* 271:19991 (1996)). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395 (1993)).

A limited number of non-conservative amino acids, amino acids that are not encoded by the genetic code, non-naturally occurring amino acids, and unnatural amino acids may be substituted for zsig81 amino acid residues.

Multiple amino acid substitutions can be made and tested using known methods of mutagenesis and screening, such as those disclosed by Reidhaar-Olson and Sauer (*Science* 241:53 (1988)) or Bowie and Sauer (*Proc. Nat'l Acad. Sci. USA* 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832 (1991), Ladner et al., U.S. Pat. No. 5,223,409, Huse, international publication No. WO 92/06204, and region-directed mutagenesis (Derbyshire et al., *Gene* 46:145 (1986), and Ner et al., *DNA* 7: 127, (1988)).

Variants of the disclosed zsig81 nucleotide and polypeptide sequences can also be generated through DNA shuffling as disclosed by Stemmer, *Nature* 370:389 (1994), Stemmer, *Proc. Nat'l Acad. Sci. USA* 91:10747 (1994), and international publication No. WO 97/20078. Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, peptides that bind to and inhibit activation of zsig81 receptor, or polypeptides that bind with anti-zsig81 antibodies, can be recovered from the host cells and rapidly sequenced using modem equipment. These methods allow the rapid determination of the importance of individual amino acid residues in a polypeptide of interest, and can be applied to polypeptides of unknown structure.

Essential amino acids in the polypeptides of the present invention can be identified according to procedures known in the art, such as site-directed mutagenesis or alanine-scanning mutagenesis (Cunningham and Wells, *Science* 244:1081 (1989), Bass et al., *Proc. Nat'l Acad. Sci. USA* 88:4498 (1991), Coombs and Corey, "Site-Directed Mutagenesis and Protein Engineering," in *Proteins: Analysis and Design*, Angeletti (ed.), pages 259–311 (Academic Press, Inc. 1998)). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699 (1996). The identities of essential amino acids can also be inferred from analysis of homologies with zsig81.

The location of zsig81 receptor binding domains can be identified by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306 (1992), Smith et al., *J. Mol. Biol.* 224:899 (1992), and Wlodaver et al., *FEBS Lett.* 309:59 (1992). Moreover, zsig81 labeled with biotin or FITC can be used for expression cloning of zsig81 receptors.

The present invention also includes "functional fragments" of zsig81 polypeptides and nucleic acid molecules encoding such functional fragments. As previously described herein, zsig81 is characterized by a four-helical bundle. Thus, the present invention further provides fusion proteins encompassing (a) polypeptide molecules comprising one or more of the regions described above, and (b) biologically active fragments comprising portions of one or more of the domains. The other polypeptide may be another regions from another cytokine, a non-native and/or an unrelated secretory signal peptide to facilitate secretion of the fusion protein. Thus, as described herein functional domains of zsig81 will be useful for preparing chimeric fusion proteins that combine helical loop domains from other short form cytokines. Such chimeras will have specificity determined by the component regions used (Kallen et al, ibid., 1999). Chimeric molecules can be prepared using one or more helices of secretory signal sequence from zsig81 in combination with corresponding regions from other cytokines.

Routine deletion analyses of nucleic acid molecules can be performed to obtain functional fragments of a nucleic acid molecule that encodes an zsig81 polypeptide. As an illustration, DNA molecules having the nucleotide sequence of SEQ ID NO: 1 can be digested with Bal31 nuclease to obtain a series of nested deletions. The fragments are then inserted into expression vectors in proper reading frame, and the expressed polypeptides are isolated and tested for zsig81, or for the ability to bind anti-zsig81 antibodies. One alternative to exonuclease digestion is to use oligonucleotide-directed mutagenesis to introduce deletions or stop codons to specify production of a desired fragment. Alternatively, particular fragments of an zsig81 gene can be synthesized using the polymerase chain reaction.

Standard methods for identifying functional domains are well-known to those of skill in the art. For example, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 kDa 2–5A synthetase induced by human interferon," in *Biological Interferon Systems, Proceedings of ISIR-TNO Meeting on Interferon Systems,* Cantell (ed.), pages 65–72 (Nijhoff 1987), Herschman, "The EGF Receptor," in *Control of Animal Cell Proliferation, Vol.* 1, Boynton et al., (eds.) pages 169–199 (Academic Press 1985), Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995), and Meisel et al., *Plant Molec. Biol.* 30:1 (1996).

The present invention also contemplates functional fragments of an zsig81 gene that has amino acid changes, compared with the amino acid sequence of SEQ ID NO:2. A variant zsig81 gene can be identified on the basis of structure by determining the level of identity with nucleotide and amino acid sequences of SEQ ID NOs:1 and 2, as discussed above. An alternative approach to identifying a variant gene on the basis of structure is to determine whether a nucleic acid molecule encoding a potential variant zsig81 gene can hybridize to a nucleic acid molecule having the nucleotide sequence of SEQ ID NO:1, as discussed above.

Amino acid sequence changes are made in zsig81 polypeptides so as to minimize disruption of higher order structure essential to biological activity. For example, when the zsig81 polypeptide comprises one or more helices, changes in amino acid residues will be made so as not to disrupt the loop length and conformation characteristics of the protein family. The effects of amino acid sequence changes can be predicted by, for example, computer modeling as disclosed above or determined by analysis of crystal structure (see, e.g., Lapthorn et al., ibid.). Other techniques that can be used, independently or in combination, to analyze and compare the structural features that affect folding of a variant protein or polypeptide to a standard molecule to determine whether such modifications would be significant are well known in the art. For example, comparison of the cysteine pattern in a variant and standard molecule can be made. Mass spectrometry and chemical modification using reduction and alkylation provide methods for determining cysteine residues which are associated with disulfide bonds or are free of such associations (Bean et al., *Anal. Biochem.* 201:216–226, 1992; Gray, *Protein Sci.* 2:1732–1748, 1993; and Patterson et al., *Anal. Chem.* 66:3727–3732, 1994). It is generally believed that if a modified molecule does not have the same cysteine pattern as the standard molecule folding would be affected. Another well known and accepted method for measuring folding is circular dichrosism (CD). Measuring and comparing the CD spectra generated by a modified molecule and standard molecule would be routine (Johnson, *Proteins* 7:205–214, 1990). Crystallography is another well known and accepted method for analyzing folding and structure. Nuclear magnetic resonance (NMR), digestive peptide mapping and epitope mapping are other known methods for analyzing folding and structurally similarities between proteins and polypeptides (Schaanan et al., *Science* 257:961–964, 1992).

A Hopp/Woods hydrophilicity profile of the zsig81 protein sequence as shown in SEQ ID NO:2 can be generated (Hopp et al., *Proc. Natl. Acad. Sci.* 78:3824–3828, 1981; Hopp, *J. Immun. Meth.* 88:1–18, 1986 and Triquier et al., *Protein Engineering* 11:153–169, 1998). The profile is based on a sliding six-residue window. Buried G, S, and T residues and exposed H, Y, and W residues were ignored. Hydrophilicity can be used to determine regions that have the most antigenic potential. For example, in zsig81, hydrophilic regions include amino acid residues 101–107 of SEQ ID NO: 2, amino acid residues 57–62 of SEQ ID NO: 2, amino acid residues 17–22 of SEQ ID NO: 2, amino acid residues 16–21 of SEQ ID NO: 2, and amino acid residues 100–105 of SEQ ID NO: 2.

Amino acid sequence changes are made in zsig81 polypeptides so as to minimize disruption of higher order structure essential to biological activity. For example changes in amino acid residues will be made so as not to disrupt the four-helix bundle characteristic of the protein family. Methods for analyzing the effect of modification in primary sequence on secondary and tertiary structure are described herein. Those skilled in the art will recognize that hydrophilicity will be taken into account when designing alterations in the amino acid sequence of a zsig81 polypeptide, so as not to disrupt the overall profile. Residues within the core of the four-helix bindle can be replaced with a residue as shown in SEQ ID NO: 6, 7, 8, and 9. Of particular interest for replacement are hydrophobic residues selected from the group consisting of Val, Leu and Ile or the group consisting of Met, Gly, Ser, Ala, Tyr and Trp. Cysteine residues at positions 2 and 76 of SEQ ID NO: 2, and the residues predicted to be on the exposed surface of the four-helix bundle will be relatively intolerant of substitution.

Polypeptides of the present invention comprise at least 6, preferably at least 9, more preferably at least 15 contiguous amino acid residues of SEQ ID NO:2. Within certain embodiments of the invention, the polypeptides comprise 20, 30, 40, 50, 100, or more contiguous residues of SEQ ID NO:2, up to the entire mature polypeptide (residues 1 to 156 of SEQ ID NO:2) or the primary translation product (residues −17 to 156 of SEQ ID NO:2). As disclosed in more detail below, these polypeptides can further comprise additional, non-zsig81 polypeptide sequence(s).

Within the polypeptides of the present invention are polypeptides that comprise an epitope-bearing portion of a protein as shown in SEQ ID NO:2. An "epitope" is a region of a protein to which an antibody can bind. See, for example, Geysen et al., *Proc. Natl. Acad. Sci. USA* 81:3998–4002, 1984. Epitopes can be linear or conformational, the latter being composed of discontinuous regions of the protein that form an epitope upon folding of the protein. Linear epitopes are generally at least 6 amino acid residues in length. Relatively short synthetic peptides that mimic part of a protein sequence are routinely capable of eliciting an antiserum that reacts with the partially mimicked protein. See, Sutcliffe et al., *Science* 219:660–666, 1983. Antibodies that recognize short, linear epitopes are particularly useful in analytic and diagnostic applications that employ denatured protein, such as Western blotting (Tobin, *Proc. Natl. Acad. Sci. USA* 76:4350–4356, 1979), or in the analysis of fixed cells or tissue samples. Antibodies to linear epitopes are also useful for detecting fragments of zsig81 such as might occur in body fluids or cell culture media.

Antigenic, epitope-bearing polypeptides of the present invention are useful for raising antibodies, including monoclonal antibodies, that specifically bind to a zsig81 protein. Antigenic, epitope-bearing polypeptides contain a sequence of at least six, preferably at least nine, more preferably from 15 to about 30 contiguous amino acid residues of a zsig81 protein (e.g., SEQ ID NO:2). Polypeptides comprising a larger portion of a zsig81 protein, i.e. from 30 to 50 residues up to the entire sequence, are included. It is preferred that the amino acid sequence of the epitope-bearing polypeptide is selected to provide substantial solubility in aqueous solvents, that is the sequence includes relatively hydrophilic residues, and hydrophobic residues are substantially avoided. Preferred such regions include residues 16–21, 17–22, 57–62, 100–105 and 101–107 of SEQ ID NO:2.

Using the methods discussed herein, one of ordinary skill in the art can identify and/or prepare a variety of polypeptides that are have substantially similar sequence identity to residues −17 to 156 or 1 to 156 of SEQ ID NO: 2, or functional fragments, e.g., residues 5 to 156 of SEQ ID NO: 2, and fusions thereof, and retain the properties of the wild-type protein such as the ability to stimulate proliferation, differentiation or induce specialized cell function.

Regardless of the particular nucleotide sequence of a variant zsig81 sequence, the sequence encodes a polypeptide that is characterized by its proliferative or differentiating activity, or ability to induce specialized cell functions, or by the ability to bind specifically to an anti-zsig81 antibody or antagonist that binds to the zsig81 receptor. More specifically, variant zsig81 genes encode polypeptides which exhibit at least 50% and preferably, greater than 70, 80 or 90%, of the activity of polypeptide encoded by the human zsig81 gene described herein.

For any zsig81 polypeptide, including variants and fusion proteins, one of ordinary skill in the art can readily generate a fully degenerate polynucleotide sequence encoding that variant using the information set forth in Tables 1 and 2 above.

The present invention further provides a variety of other polypeptide fusions (and related multimeric proteins comprising one or more polypeptide fusions). For example, a zsig81 polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin- zsig81 polypeptide fusions can be expressed in genetically engineered cells (to produce a variety of multimeric zsig81 analogs). Auxiliary domains can be fused to zsig81 polypeptides to target them to specific cells, tissues, or macromolecules (e.g., collagen). For example, a zsig81 polypeptide or protein could be targeted to a predetermined cell type by fusing a zsig81 polypeptide to a ligand that specifically binds to a receptor on the surface of the target cell, or fused to an antibody directed to an antigen expressed on a specific target cell type. In this way, polypeptides and proteins can be targeted for therapeutic or diagnostic purposes. A zsig81 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1–9, 1996.

The polypeptides of the present invention, including full-length proteins, fragments thereof and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., N.Y., 1987.

In general, a DNA sequence encoding a zsig81 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zsig81 polypeptide into the secretory pathway of a host cell, a secretory signal sequence (also known as a leader sequence, prepro sequence or pre sequence) is provided in the expression vector. The secretory signal sequence may be that of the zsig81 polypeptide, or may be derived from another secreted protein (e.g., t-PA) or synthesized de novo. The secretory signal sequence is operably linked to the zsig81 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. A signal fusion polypeptide can be made wherein a secretory signal sequence derived from amino acid residue −17 to 1 of SEQ ID NO:2 is operably linked to a DNA sequence encoding another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein. Such fusions may be used in vivo or in vitro to direct peptides through the secretory pathway.

Cultured mammalian cells are suitable hosts within the present invention. Methods for introducing exogenous DNA into mammalian host cells include calcium phosphate-mediated transfection (Wigler et al., Cell 14:725, 1978; Corsaro and Pearson, Somatic Cell Genetics 7:603, 1981: Graham and Van der Eb, Virology 52:456, 1973), electroporation (Neumann et al., EMBO J. 1:841–845, 1982), DEAE-dextran mediated transfection (Ausubel et al., ibid.), and liposome-mediated transfection (Hawley-Nelson et al., Focus 15:73, 1993; Ciccarone et al., Focus 15:80, 1993), and viral vectors (Miller and Rosman, BioTechniques 7:980–90,. 1989; Wang and Finer, Nature Med. 2:714–6, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., J. Gen. Virol. 36:59–72, 1977) and Chinese hamster ovary (e.g. CHO-K1; ATCC No. CCL 61) cell lines. Additional suitable cell lines are known in the art and available from public depositories such as the American Type Culture Collection, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of Agrobacterium rhizogenes as a vector for expressing genes in plant cells has been reviewed by Sinkar et al., J. Biosci. (Bangalore) 11:47–58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from Autographa californica nuclear polyhedrosis virus (AcNPV). DNA encoding the zsig81 polypeptide is inserted into the baculoviral genome in place of the AcNPV polyhedrin gene coding sequence by one of two methods. The first is the traditional method of homologous DNA recombination between wild-type AcNPV and a transfer vector containing the zsig81 flanked by AcNPV sequences. Suitable insect cells, e.g. SF9 cells, are infected with wild-type AcNPV and transfected with a transfer vector comprising a zsig81 polynucleotide operably linked to an AcNPV polyhedrin gene promoter, terminator, and flanking sequences. See, King, L. A. and Possee, R. D., The Baculovirus Expression System: A Laboratory Guide, London, Chapman & Hall; O'Reilly, D. R. et al., Baculovirus Expression Vectors: A Laboratory Manual, New York, Oxford University Press., 1994; and, Richardson, C. D., Ed., Baculovirus Expression Protocols. Methods in Molecular Biology, Totowa, N.J., Humana Press, 1995. Natural recombination within an insect cell will result.in a recombinant baculovirus which contains zsig81 driven by the polyhedrin promoter. Recombinant viral stocks are made by methods commonly used in the art.

The second method of making recombinant baculovirus utilizes a transposon-based system described by Luckow (Luckow, V. A, et al., J Virol 67:4566–79, 1993). This system is sold in the Bac-to-Bac kit (Life Technologies, Rockville, Md.). This system utilizes a transfer vector, pFastBac1™ (Life Technologies) containing a Tn7 transposon to move the DNA encoding the zsig81 polypeptide into a baculovirus genome maintained in E. coli as a large plasmid called a "bacmid." The pFastBac1™ transfer vector utilizes the AcNPV polyhedrin promoter to drive the expression of the gene of interest, in this case zsig81. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins, M. S. and Possee, R. D., J. Gen. Virol. 71:971–6, 1990; Bonning, B. C. et al., J. Gen. Virol. 75:1551–6, 1994; and, Chazenbalk, G. D., and Rapoport, B., J. Biol. Chem. 270:1543–9, 1995. In such transfer vector constructs, a short or long version of the basic protein promoter can be used. Moreover, transfer vectors can be constructed which replace the native zsig81 secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native zsig81 secretory-signal sequence. In addition, transfer vectors can include an in-frame fusion with DNA encoding an epitope tag at the C- or N-terminus of the expressed zsig81 polypeptide, for example, a Glu-Glu epitope tag (Grussenmeyer, T. et al., *Proc. Natl. Acad. Sci.* 82:7952–4, 1985). Using a technique known in the art, a transfer vector containing zsig81 is transformed into *E. Coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses zsig81 is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2-5 \times 10^5$ cells to a density of $1-2 \times 10^6$ cells at which time a recombinant viral stock is added at a multiplicity of infection (MOI) of 0.1 to 10, more typically near 3. The recombinant virus-infected cells typically produce the recombinant zsig81 polypeptide at 12–72 hours postinfection and secrete it with varying efficiency into the medium. The culture is usually harvested 48 hours postinfection. Centrifugation is used to separate the cells from the medium (supernatant). The supernatant containing the zsig81 polypeptide is filtered through micropore filters, usually 0.45 $\mu$m pore size. Procedures used are generally described in available laboratory manuals (King, L. A. and Possee, R. D., ibid.; O'Reilly, D. R. et al., ibid.; Richardson, C. D., ibid.). Subsequent purification of the zsig81 polypeptide from the supernatant can be achieved using methods described herein.

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–65, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

The use of Pichia methanolica as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in Pichia methanolica is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (Aug1 and AUG2) are deleted. For production of secreted proteins, host cells deficient in vacuolar protease genes (PEP4 and PRB1) are preferred. Electropoation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant ($\omega$) of from 1 to 40 milliseconds, most preferably about 20 milliseconds.

Prokaryotic host cells, including strains of the bacteria *Escherichia coli*, Bacillus and other genera are also useful host cells within the present invention. Techniques for transforming these hosts and expressing foreign DNA sequences cloned therein are well known in the art (see, e.g., Sambrook et al., ibid.). When expressing a zsig81 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Expressed recombinant zsig81 polypeptides (or chimeric zsig81 polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can be isolated by exploitation of size, charge and hydrophobicity. For example, immobilized metal ion adsorption (IMAC) chromatography can be used to purify histidine-rich proteins (E. Sulkowski, *Trends in Biochem.* 3:1–7, 1985). Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp.529–39). Within additional embodiments of the invention, a fusion of the polypeptide of interest and an affinity tag (e.g., maltose-binding protein, an immunoglobulin domain) may be constructed to facilitate purification.

ZSIG81 has a domain homologous to the heparin binding domain described previously for CTGF, and exploitation of this property may be useful for purification of zsig81. For a review, see, Burgess et al., *Ann. Rev. of Biochem.* 58:575–606, 1989. Members of the FGF family, which also have a heparin binding domain can be purified to apparent homogeneity by heparin-Sepharose affinity chromatography (Gospodarowicz et al., *Proc. Natl. Acad. Sci.* 81:6963–6967, 1984) and eluted using linear step gradients of NaCl (Ron et al., *J. Biol. Chem.* 268(4):2984–2988, 1993; *Chromatography: Principles & Methods*, pp. 77–80, Pharmacia LKB Biotechnology, Uppsala, Sweden, 1993; in "Immobilized Affinity Ligand Techniques", Hermanson et al., eds., pp. 165–167, Academic Press, San Diego, 1992; Kjellen et al., *Ann. Rev. Biochem.Ann. Rev. Biochem.* 60:443–474, 1991; and Ke et al., *Protein Expr. Purif.* 3(6):497–507, 1992.)

Protein refolding (and optionally reoxidation) procedures may be advantageously used. It is preferred to purify the protein to >80% purity, more preferably to >90% purity, even more preferably >95%, and particularly preferred is a pharmaceutically pure state, that is greater than 99.9% pure with respect to contaminating macromolecules, particularly other proteins and nucleic acids, and free of infectious and pyrogenic agents. Preferably, a purified protein is substantially free of other proteins, particularly other proteins of animal origin.

Zsig81 polypeptides or fragments thereof may also be prepared through chemical synthesis (Merrifield, *J. Am. Chem. Soc.* 85:2149, 1963). Zsig81 polypeptides may be monomers or multimers; glycosylated or non-glycosylated; pegylated or non-pegylated; and may or may not include an initial methionine amino acid residue.

The activity of molecules of the present invention can be measured using a variety of assays that measure cell proliferation, differentiation, chemotaxis or induction of specialized cell functions. Of particular interest are changes in proliferation or differentiation of cells, particularly cells isolated from heart or liver tissue. Proliferation and differentiation can be measured in vitro using cultured cells or in vivo by administering molecules of the claimed invention to the appropriate animal model. Assays measuring cell proliferation or differentiation are well known in the art. For example, assays measuring proliferation include such assays as chemosensitivity to neutral red dye (Cavanaugh et al., *Investigational New Drugs* 8:347–354, 1990, incorporated herein by reference), incorporation of radiolabelled nucleotides (Cook et al., *Analytical Biochem.* 179:1–7, 1989, incorporated herein by reference), incorporation of 5-bromo-2'-deoxyuridine (BrdU) in the DNA of proliferating cells (Porstmann et al., *J. Immunol. Methods* 82:169–179, 1985, incorporated herein by reference), and use of tetrazolium salts (Mosmann, *J. Immunol. Methods* 65:55–63, 1983; Alley et al., *Cancer Res.* 48:589–601, 1988; Marshall et al., *Growth Reg.* 5:69–84, 1995; and Scudiero et al., *Cancer Res.* 48:4827–4833, 1988; all incorporated herein by reference). Assays measuring differentiation include, for example, measuring cell-surface markers associated with stage-specific expression of a tissue, enzymatic activity, functional activity or morphological changes (Watt, *FASEB*, 5:281–284, 1991; Francis, *Differentiation* 57:63–75, 1994; Raes, *Adv. Anim. Cell Biol. Technol. Bioprocesses*, 161–171, 1989; all incorporated herein by reference).

Examples of assays measuring induction of specialized cell functions include: extracellular matrix protein mRNA induction assays (Frazier et al., *J. Invest. Dermatol.* 107:404–411, 1996); $^{35}S$ methionine pulse-chase assays measuring stimulation of matrix protein synthesis (Frazier et al., ibid., 1996); subcutaneous administration of growth factors to mice (Roberts et al., *Proc. Natl. Acad. Sci. USA* 83:4167–4171, 1986); and in situ hybridization to measure changes in mRNA expression (Favaet al.,*Blood* 76:1946–1955, 1990).

Cell migration is assayed essentially as disclosed by Kähler et al. (*Arteriosclerosis, Thrombosis, and Vascular Biology* 17:932–939, 1997). A protein is considered to be chemotactic if it induces migration of cells from an area of low protein concentration to an area of high protein concentration.

Cell adhesion activity is assayed essentially as disclosed by LaFleur et al. (*J. Biol. Chem.* 272:32798–32803, 1997). Briefly, microtiter plates are coated with the test protein, non-specific sites are blocked with BSA, and cells (such as smooth muscle cells, leukocytes, or endothelial cells) are plated at a density of approximately $10^4$–$10^5$ cells/well. The wells are incubated at 37° C. (typically for about 60 minutes), then non-adherent cells are removed by gentle washing. Adhered cells are quantitated by conventional methods (e.g., by staining with crystal violet, lysing the cells, and determining the optical density of the lysate). Control wells are coated with a known adhesive protein, such as fibronectin or vitronectin.

Assays for angiogenic activity are also known in the art. For example, the effect of zsig81 proteins on primordial endothelial cells in angiogenesis can be assayed in the chick chorioallantoic membrane angiogenesis assay (Leung, *Science* 246:1306–1309, 1989; Ferrara, *Ann. NY Acad. Sci.* 752:246–256, 1995). Other suitable assays include microinjection of early stage quail (Coturnix coturnix japonica) embryos as disclosed by Drake et al. (*Proc. Natl. Acad. Sci. USA* 92:7657–7661, 1995); the rodent model of corneal neovascularization disclosed by Muthukkaruppan and Auerbach (*Science* 205:1416–1418, 1979), wherein a test substance is inserted into a pocket in the cornea of an inbred mouse; and the hampster cheek pouch assay (Höckel et al., *Arch. Surg.* 128:423–429, 1993).

The biological activities of zsig81 proteins can be studied in non-human animals by administration of exogenous protein, by expression of zsig81-encoding polynucleotides, and by suppression of endogenous zsig81 expression through antisense or knock-out techniques. Zsig81 proteins can be administered or expressed individually, in combination with other zsig81 proteins, or in combination with non-zsig81 proteins, including other growth factors. Test animals are monitored for changes in such parameters as clinical signs, body weight, blood cell counts, clinical chemistry, histopathology, and the like.

Stimulation of coronary collateral growth can be measured in known animal models, including a rabbit model of peripheral limb ischemia and hind limb ischemia and a pig model of chronic myocardial ischemia (Ferrara et al., *Endocrine Reviews* 18:4–25, 1997). Zsig81 proteins are assayed in the presence and absence of VEGFs, angiopoietins, and basic FGF to test for combinatorial effects. These models can be modified by the use of adenovirus or naked DNA for gene delivery as disclosed in more detail below, resulting in local expression of the test protein(s).

Efficacy of zsig81 polypeptides in promoting wound healing can be assayed in animal models. One such model is the linear skin incision model of Mustoe et al. (*Science* 237:1333, 1987). Subcutaneous implants can be used to assess compounds acting in the early stages of wound healing (Broadley et al., *Lab. Invest.* 61:571, 1985; Sprugel et al., *Amer. J. Pathol.* 129: 601, 1987).

Expression of zsig81 proteins in animals provides models for study of the biological effects of overproduction or inhibition of protein activity in vivo. Zsig81-encoding polynucleotides can be introduced into test animals, such as mice, using viral vectors or naked DNA, or transgenic animals can be produced. In general it is preferred to express a zsig81 protein with a secretory peptide. Suitable secretory peptides include the zsig81 secretory peptide (e.g., residues –17 to 1 of SEQ ID NO:2) and heterologous secretory peptides. A preferred heterologous secretory peptide is that of human tissue plasminogen activator (t-PA). The t-PA secretory peptide may be modified to reduce undesired proteolytic cleavage as disclosed in U.S. Pat. No. 5,641,655.

One in vivo approach for assaying proteins of the present invention utilizes viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acids. For review, see Becker et al., *Meth. Cell Biol.* 43:161–89, 1994; and Douglas and Curiel, *Science & Medicine* 4:44–53, 1997. The adenovirus system offers several advantages. Adenovirus can (i) accommodate relatively large DNA inserts; (ii) be grown to high-titer; (iii) infect a broad range of mammalian cell types; and (iv) be used with many different promoters including ubiquitous, tissue specific, and regulatable promoters. Because adenoviruses are stable in the bloodstream, they can be administered by intravenous injection.

Using adenovirus vectors where portions of the adenovirus genome are deleted, inserts are incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined. Adenoviral vectors containing various deletions of viral genes can be used in an attempt to reduce or eliminate immune responses to the vector. Such adenoviruses are E1 deleted, and in addition contain deletions of E2A or E4 (Lusky et al., *J. Virol.* 72:2022–2032, 1998; Raper et al., *Human Gene Therapy* 9:671–679, 1998). In addition, deletion of E2b is reported to reduce immune responses (Amalfitano, et al., *J. Virol.* 72:926–933, 1998). Generation of so-called "gutless" adenoviruses where all viral transcription units are deleted is particularly advantageous for insertion of large inserts of heterologous DNA. For review, see Yeh and Perricaudet, *FASEB J.* 11:615–623, 1997.

In another embodiment, a zsig81 gene can be introduced in a retroviral vector as described, for example, by Anderson et al., U.S. Pat. No. 5,399,346; Mann et al., *Cell* 33:153, 1983; Temin et al., U.S. Pat. No. 4,650,764; Temin et al., U.S. Pat. No. 4,980,289; Markowitz et al.,*J. Virol.* 62:1120, 1988; Temin et al., U.S. Pat. No. 5,124,263; Dougherty et al., WIPO publication WO 95/07358; and Kuo et al., *Blood* 82:845, 1993.

In an alternative method, the vector can be introduced by "lipofection" in vivo using liposomes. Synthetic cationic lipids can be used to prepare liposomes for in vivo transfection of a gene encoding a marker (Felgner et al., *Proc. Natl. Acad. Sci.* USA 84:7413–7, 1987; Mackey et al., *Proc. Natl. Acad. Sci.* USA 85:8027–31, 1988). The use of lipofection to introduce exogenous genes into specific organs in vivo has certain practical advantages. Molecular targeting of liposomes to specific cells represents one area of benefit. For instance, directing transfection to particular cell types is particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

Within another embodiment target cells are removed from the animal, and the DNA is introduced as a naked DNA plasmid. The transformed cells are then re-implanted into the body of the animal. Naked DNA vectors can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–7, 1992; Wu et al., *J. Biol. Chem.* 263:14621–4, 1988.

Mice engineered to express the zsig81 gene, referred to as "transgenic mice," and mice that exhibit a complete absence of zsig81 gene function, referred to as "knockout mice," can also be generated (Snouwaert et al., *Science* 257:1083, 1992; Lowell et al., *Nature* 366:740–42, 1993; Capecchi, *Science* 244:1288–1292, 1989; Palmiter et al., *Ann. Rev. Genet.* 20:465–499, 1986). Transgenesis experiments can be performed using normal mice or mice with genetic disease or other altered phenotypes. Transgenic mice that over-express zsig81, either ubiquitously or under a tissue-specific or tissue-restricted promoter, can be used to determine whether or not over-expression causes a phenotypic change. Preferred promoters include metallothionein and albumin gene promoters. The metallothionein-1 (MT-1) promoter provides expression in liver and other tissues, often leading to high levels of circulating protein. Over-expression of a wild-type zsig81 polypeptide, polypeptide fragment or a mutant thereof may alter normal cellular processes, resulting in a phenotype that identifies a tissue in which zsig81 expression is functionally relevant and may indicate a therapeutic target for the zsig81, its agonists or antagonists. For example, a preferred transgenic mouse to engineer is one that over-expresses a full-length zsig81 sequence. Such over-expression may result in a phenotype that shows similarity with human diseases. Similarly, knockout zsig81 mice can be used to determine where zsig81 is absolutely required in vivo. The phenotype of knockout mice is predictive of the in vivo effects of zsig81 antagonists. Knockout mice can also be used to study the effects of zsig81 proteins in models of disease, including, for example, cancer, atherosclerosis, rheumatoid arthritis, ischemia, and cardiovascular disease. The human zsig81 cDNA can be used to isolate murine zsig81 mRNA, cDNA and genomic DNA as disclosed above, which are subsequently used to generate knockout mice. These mice may be employed to study the zsig81 gene and the protein encoded thereby in an in vivo system, and can be used as in vivo models for corresponding human diseases. Moreover, transgenic mice expressing zsig81antisense polynucleotides or ribozymes directed against zsig81, described herein, can be used analogously to knockout mice described above.

Antisense methodology can be used to inhibit zsig81 gene transcription to examine the effects of such inhibition in vivo. Polynucleotides that are complementary to a segment of a zsig81-encoding polynucleotide (e.g., a polynucleotide as set froth in SEQ ID NO:1) are designed to bind to zsig81-encoding mRNA and to inhibit translation of such mRNA. Such antisense oligonucleotides can also be used to inhibit expression of zsig81 polypeptide-encoding genes in cell culture.

Proteins of the present invention are useful for modulating the proliferation, differentiation, migration, or metabolism of responsive cell types, which include both primary cells and cultured cell lines. Of particular interest in this regard are hematopoietic cells (including stem cells and mature myeloid and lymphoid cells), endothelial cells, and mesenchymal cells (including fibroblasts, and cardiac and smooth muscle cells). Zsig81 polypeptides are added to tissue culture media for these cell types at a concentration of about 10 pg/ml to about 1000 ng/ml. Those skilled in the art will recognize that zsig81 proteins can be advantageously combined with other growth factors in culture media.

Dendritic cells are the most potent antigen presenting cells (APCs) in the immune system. Dendritic cells are the only cells that present antigen to, and activate, naive $CD4^+T$ cells in vivo (Levin et al., *J. Immunol.* 151:6742–6750, 1993). Dendritic cells are found in primary and secondary lymphoid organs (e.g., thymus, lymph nodes, tonsils, Peyer's patches, and spleen), as well as in non-lymphoid organs and tissues (e.g., heart, liver, lung, gut, and in the skin as epidermal Langerhans cells). Dendritic cells are also prevalent in afferent lymph, but are rare in blood. For reviews, see Steinman, *Ann. Rev. Immunol.* 9:271–296, 1991 and Knight et al., *J. Invest. Dermatol.* 99:33S-38S, 1992.

Dendritic cells are thought to originate from a single hematopoietic progenitor cell. As progenitor cells begin the process of differentiation they migrate to selected tissue and/or organs, where they appear to undergo additional differentiation. If isolated from tissue, dendritic cells are immature; that is, the cells are not fully differentiated, are inefficient at antigen presentation, express low levels of MHC Class II molecules and do not stimulate proliferation of T-cells in an allogenic mixed leukocyte reaction (MLR). However, when immature dendritic cells are exposed to foreign proteins, they become capable of taking up and presenting soluble antigen via newly synthesized MHC Class II molecules, and simultaneously leave their tissue residence and migrate to lymph nodes and spleen. After migrating from the origin tissue, the dendritic cells are mature; that is, they exhibit high levels of MHC Class II, accessory and co-stimulatory molecules, as well as full APC function (Steinman, ibid., 1990 and Ibrahim et al., *Immunol. Today* 16:181–186, 1995). Recently, availability of immortalized dendritic cells have expanded scientists' ability to investigate antigen uptake and processing by dendritic cells and their precursor cells (see, e.g., U.S. Pat. 5,648,219.)

Dendritic cells have been implicated as a causative cell-type in a number of different diseases that involve immune responses, including contact sensitivity, tumor immunity, HIV-1 infection and autoimmunity (e.g., Type I diabetes, multiple sclerosis and rheumatoid arthritis). These cells are believed to play a role in graft rejection, where cells from the allograft migrate into the lymphoid organs of the recipient and initiate a deleterious immune response.

Recent investigations have demonstrated that cytokines play an essential role in the maturation and ability of dendritic cells to present antigen. GM-CSF was found to enhance antigen presentation by Langerhans cells in vivo and tumor immunity in vitro in other dendritic cells (Grabbe et al., *Immunology Today* 16:117–121, 1995.) Other cytokines believed to play a role in dendritic cell function and differentiation include: FLT3 ligand, IL-12, KIT ligand, TNT-α and IL-4 in conjunction with GM-CSF (Shurin et al., *Cytokine & Growth Factor Reviews* 9:37–48, 1998); Stem cell factor, TGF-β, IL-6 and IL-3 (Brugger et al., *Annals N.Y. Acad. Sci.* 872:363–371, 1999).

Molecules of the present invention have been shown to stimulate the proliferation of cells expressing markers associated with dendritic lineage cells. Conditioned medium from human embryonic kidney cells transfected with cDNA for murine zsig81 stimulated proliferation of bone marrow cultures. The bone marrow culture contained multiple cell lineages, at various stages of differentiation, and the outgrowth from the cultures resulted in a significant increase in cells that were $CD80^+$, $CD86^+$, MHC II and $CD11c^+$, which are markers for dendritic cells of a possible lymphoid or myeloid origin. The identification of thymic lymphoid-related dendritic cells are phenotypically distinguishable from myeloid related dendritic cells. While the various functional differences between dendritic cells of lymphoid and myeloid origin have not been fully elucidated, lymphoid related dendritic cells may be involved in self-antigen tolerance, while myeloid related dendritic cells involved in endocytosis of foreign antigens (de St. Groth, *Immunology Today* 19:448–454, 1998.)

Dendritic cells have activities that are specifically associated with the maturity of the cell, i.e., its differentiated state. To identify a cell's maturity, a population of established cells is assayed and analyzed for a set of differentiation markers that are characteristic of the cell's stage in the differentiation pathway. Preferably, this is done by isolating at least a portion of the cells and subjecting this subpopulation to such analysis.

A set of differentiation markers is defined as one or more phenotypic properties that can be identified, and that are specific to a particular cell type and stage of maturity. Differentiation markers are transiently exhibited at various stages of the cell's progression toward terminal differentiation. Pluripotent stem cells that can regenerate without commitment to a specific cell lineage express a set of differentiation markers that are diminished when commitment to a particular cell lineage is made. Precursor cells express a set of differentiation markers that may or may not continue to be expressed as the cells progress down the cell lineage pathway toward maturation. Differentiation markers that are expressed exclusively by mature cells usually represent functional properties, such as cell products, enzymes to produce cell products and receptors. It is possible that with exposure to the appropriate factors, the cell line of the present invention can differentiate and mature into other cells of the monocytic cell lineage. Differentiation markers used for identifying dendritic cells include: Mac-1, F4/80, FcγRII/III receptor (FcR), MHC class I, MHC class II, B7-1, B7-2, ICAM-1, CD44, N418, and NLDC-145.

In immature dendritic cells, F4/80 (Lee et al., *J. Exp. Med.* 161:475, 1985) and FcR (Unkeless, *J. Exp. Med.* 150:580, 1979) are detectable, but at levels lower than those seen in a macrophage using monoclonal antibodies that bind F4/80 (Caltag, San Fransisco, Calif.) and 2.4G2 for FcR binding (PharMingen, San Diego, Calif.); MHC class I is detectable using the monoclonal antibody EH144.3 (Geier et al., J. Immunol. 137:1239, 1986); MHC class II is detectable only at low levels using the monoclonal antibody AF6-120.1 (PharMingen); B7-1 and B7-2 are detectable at low levels (Nabavi et al., *Nature* 360:266, 1992 and Hathcock et al., *Science* 262:905, 1993, respectively) using monoclonal antibodies IG10 (PharMingen) and GL1 (PharMingen); ICAM-1 (Rothein et al., *J. Immunol.* 137:1270, 1986), using monoclonal antibody 3E2 (PharMingen), and CD44 (Lesley et al., *Immunogenetics* 15:313, 1982), using monoclonal antibody IM7 (PharMingen), are detectable at high levels; and at least one of the dendritic cell markers CD11c (Metaly et al., *J. Exp. Med.* 171:1753, 1990), using the monoclonal antibody N418, or DC-205 (Kraal et al., *J. Exp. Med.* 163:981, 1986), using the monoclonal antibodies NLDC-145 (Accurate Chem. and Scientific, Westbury, N.Y.) and 33D1 (Nussenzweig et al., *Proc. Natl. Acad. Sci. USA.* 79:161, 1982), should be detectable. The skilled practitioner would recognize that not all of these differentiation markers may be present and that expression levels may vary. In activated dendritic cells, high levels of MHC class II are detectable; B7-2 and ICAM-1 are expressed at higher levels, and F4/80 is expressed at lower levels than seen in immature dendritic cells.

Analyses of the cell surface using monoclonal antibodies are made using a flow cytometer, see, for example, Fink et al., *J. Exp. Med.* 176:1733, 1992 and Crowley et al., *Cellular Immunol.* 118:108–125, 1989. Briefly, the cells are either combined with monoclonal antibodies directly conjugated to fluorochromes, or with unconjugated primary antibody and subsequently with commercially available secondary antibodies conjugated to fluorochromes. The stained cells are analyzed using a FACScan (Becton Dickinson, Mountain View, Calif.) using LYSYS II or Cell Quest software (Becton Dickinson).

Identification of activated dendritic cells is confirmed by the cells' ability to stimulate the proliferation of allogeneic T cells in a MLR. Briefly, activated dendritic cells are incubated with allogeneic T cells in a 96-well microtiter dish (American Scientific Products, Chicago, Ill.). Stimulation of the T cells to proliferate is measured by incorporation of $^3H$-thymidine. It is preferred to expose the dendritic cells of the present invention to irradiation to slow the proliferation of the dendritic cells and reduce background in the assay caused by incorporation of $^3H$-thymidine by the dendritic cells.

The dendritic cells are activated to induce expression of MHC class II molecules on the cell surface, making these mature dendritic cells competent for antigen processing and presentation. These activated cells (i.e., stimulators) are then exposed to antigen for a time sufficient for antigen presentation. One skilled in the art would recognize that the time required for endocytosis, processing and presentation of antigen is dependent upon the proteinaceous antigen being used for this purpose. Methods for measuring antigen uptake and presentation are known in the art. For example, dendritic cells can be incubated with a soluble protein antigen (e.g., ovalbumin or conalbumin) for 3–24 hours then washed to remove exogenous antigen.

These antigen-presenting stimulator cells are then mixed with responder cells, preferably naive or antigen-primed T lymphocytes. After an approximately 72 hour incubation (for primed T lymphocytes) or approximately 4–7 d period (for naive T lymphocytes), the activation of T cells in response to the processed and presented antigen is measured. In a preferred embodiment, T cell activation is determined by measuring T cell proliferation using $^3H$-thymidine uptake (Crowley et al., *J. Immunol. Meth.* 133:55–66, 1990). The responder cells in this regard can be PBMN cells, cultured T cells, established T cell lines or hybridomas. Responder cell activation can be measured by the production of cytokines, such as L-2, or by determining T cell-specific activation markers. Cytokine production can be assayed by the testing the ability of the stimulator+ responder cell culture supernatant to stimulate growth of cytokine-dependent cells. T cell-specific activation markers may be detected using antibodies specific for such markers.

For T cell proliferation assays, it is preferred to inhibit the proliferation of dendritic cells prior to mixing with T responder cells. This inhibition may be achieved by exposure to gamma irradiation or to an anti-mitotic agent, such as mitomycin C.

Alternatively, activated dendritic cells can be used to induce non-responsiveness in T lymphocytes. In addition to MHC class II recognition, T cell activation requires co-receptors on the antigen-presenting cell (APC; e.g., the dendritic cell) that have been stimulated with co-stimulatory molecules. By blocking or eliminating stimulation of such co-receptors (for instance, by blocking with anti-receptor or anti-ligand antibodies, or by "knocking out" the gene(s) encoding such receptors), presentation of antigen by co-receptor-deficient dendritic cells can be used to render T lymphocytes non-responsive to antigen.

Zsig81 proteins may be used either alone or in combination with other hematopoietic factors such as IL-3, G-CSF, GM-CSF, IL-4, M-CSF, IL-12 or stem cell factor to enhance expansion and mobilization of hematopoietic or mesenchymal stem cells, including precursor stem cells. Cells that can be expanded in this manner include cells isolated from bone marrow, cells isolated from blood, neonatal heart or liver. Zsig81 proteins may also be given directly to an individual to enhance stem cell production and differentiation within the treated individual. In particular, zsig81 can be used for expansion of dendritic cell and dendritic cell precursor populations.

Zsig81 proteins can also be used to identify inhibitors of their activity. Test compounds are added to the assays disclosed above to identify compounds that inhibit the activity of zsig81 protein. In addition to those assays disclosed above, samples can be tested for inhibition of zsig81 activity within a variety of assays designed to measure receptor binding or the stimulation/inhibition of zsig81-dependent cellular responses. For example, zsig81-responsive cell lines can be transfected with a reporter gene construct that is responsive to a zsig81-stimulated. cellular pathway. Reporter gene constructs of this type are known in the art, and will generally comprise a zsig81-activated serum response element (SRE) operably linked to a gene encoding an assayable protein, such as luciferase. Candidate compounds, solutions, mixtures or extracts are tested for the ability to inhibit the activity of zsig81 on the target cells as evidenced by a decrease in zsig81 stimulation of reporter gene expression. Assays of this type will detect compounds that directly block zsig81 binding to cell-surface receptors, as well as compounds that block processes in the cellular pathway subsequent to receptor-ligand binding. In the alternative, compounds or other samples can be tested for direct blocking of zsig81 binding to receptor using zsig81 tagged with a detectable label (e.g., $^{125}$I, biotin, horseradish peroxidase, FITC, and the like). Within assays of this type, the ability of a test sample to inhibit the binding of labeled zsig81 to the receptor is indicative of inhibitory activity, which can be confirmed through secondary assays. Receptors used within binding assays may be cellular receptors or isolated, immobilized receptors.

The activity of zsig81 proteins can be measured with a silicon-based biosensor microphysiometer that measures the extracellular acidification rate or proton excretion associated with receptor binding and subsequent physiologic cellular responses. An exemplary such device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell et al., *Science* 257:1906–1912, 1992; Pitchford et al., *Meth. Enzymol.* 228:84–108, 1997; Arimilli et al., *J. Immunol. Meth.* 212:49–59, 1998; and Van Liefde et al., *Eur. J. Pharmacol.* 346:87–95, 1998. The microphysiometer can be used for assaying adherent or non-adherent eukaryotic or prokaryotic cells. By measuring extracellular acidification changes in cell media over time, the microphysiometer directly measures cellular responses to various stimuli, including zsig81 proteins, their agonists, and antagonists. Preferably, the microphysiometer is used to measure responses of a zsig81-responsive eukaryotic cell, compared to a control eukaryotic cell that does not respond to zsig81 polypeptide. Zsig81-responsive eukaryotic cells comprise cells into which a receptor for zsig81 has been transfected creating a cell that is responsive to zsig81, as well as cells naturally responsive to zsig81 such as cells derived from vascular, cardiac, hematopoietic, or hepatic tissue. Differences, measured by a change, for example, an increase or diminution in extracellular acidification, in the response of cells exposed to zsig81 polypeptide, relative to a control not exposed to zsig81, are a direct measurement of zsig81-modulated cellular responses. Moreover, such zsig81-modulated responses can be assayed under a variety of stimuli. The present invention thus provides methods of identifying agonists and antagonists of zsig81 proteins, comprising providing cells responsive to a zsig81 polypeptide, culturing a first portion of the cells in the absence of a test compound, culturing a second portion of the cells in the presence of a test compound, and detecting a change, for example, an increase or diminution, in a cellular response of the second portion of the cells as compared to the first portion of the cells. The change in cellular response is shown as a measurable change in extracellular acidification rate. Culturing a third portion of the cells in the presence of a zsig81 protein and the absence of a test compound provides a positive control for the zsig81-responsive cells and a control to compare the agonist activity of a test compound with that of the zsig81 polypeptide. Antagonists of zsig81 can be identified by exposing the cells to zsig81 protein in the presence and absence of the test compound, whereby a reduction in zsig81-stimulated activity is indicative of antagonist activity in the test compound.

Zsig81 proteins can also be used to identify cells, tissues, or cell lines that respond to a zsig81-stimulated pathway. The microphysiometer, described above, can be used to rapidly identify ligand-responsive cells, such as cells responsive to zsig81 proteins. Cells are cultured in the presence or absence of zsig81 polypeptide. Those cells that elicit a measurable change in extracellular acidification in the presence of zsig81 are responsive to zsig81. Responsive cells can than be used to identify antagonists and agonists of zsig81 polypeptide as described above.

Inhibitors of zsig81 activity (zsig81 antagonists) include anti-zsig81 antibodies and soluble zsig81 receptors, as well as other peptidic and non-peptidic agents, including ribozymes, small molecule inhibitors, and angiogenically or mitogenically inactive receptor-binding fragments of zsig81 polypeptides. Such antagonists can be use to block biological activities of zsig81, including mitogenic, chemotactic, or angiogenic effects.

The polypeptides, nucleic acids, and antibodies of the present invention may be used in diagnosis or treatment of disorders associated with cell loss or abnormal cell proliferation (including cancer), including impaired or excessive vasculogenesis or angiogenesis and autoimmune disease. Labeled zsig81 polypeptides may be used for imaging tumors or other sites of abnormal cell proliferation.

As would be evident to one of ordinary skill in the art, polyclonal antibodies can be generated from inoculating a variety of warm-blooded animals such as horses, cows, goats, sheep, dogs, chickens, rabbits, mice, and rats with a zsig81 polypeptide or a fragment thereof.

The immunogenicity of a zsig81 polypeptide may be increased through the use of an adjuvant, such as alum (aluminum hydroxide) or Freund's complete or incomplete adjuvant. Polypeptides useful for immunization also include fusion polypeptides, such as fusions of zsig81 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Moreover, human antibodies can be produced in transgenic, non-human animals that have been engineered to contain human immunoglobulin genes as disclosed in WIPO Publication WO 98/24893. It is preferred that the endogenous immunoglobulin genes in these animals be inactivated or eliminated, such as by homologous recombination.

Antibodies are considered to be specifically binding if: 1) they exhibit a threshold level of binding activity, and 2) they do not significantly cross-react with related polypeptide molecules. A threshold level of binding is determined if anti-zsig81 antibodies herein bind to a zsig81 polypeptide, peptide or epitope with an affinity at least 10-fold greater than the binding affinity to control (non-zsig81) polypeptide. It is preferred that the antibodies exhibit a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, G., Ann. NY Acad. Sci. 51: 660–672, 1949).

Whether anti-zsig81 antibodies do not significantly cross-react with related polypeptide molecules is shown, for example, by the antibody detecting zsig81 polypeptide but not known related polypeptides using a standard Western blot analysis (Ausubel et al., ibid.). Examples of known related polypeptides are those disclosed in the prior art, such as known orthologs, and paralogs. Screening can also be done using non-human zsig81, and zsig81 mutant polypeptides. Moreover, antibodies can be "screened against" known related polypeptides, to isolate a population that specifically binds to the zsig81 polypeptides. For example, antibodies raised to zsig81 are adsorbed to related polypeptides adhered to insoluble matrix; antibodies specific to zsig81 will flow through the matrix under the proper buffer conditions. Screening allows isolation of polyclonal and monoclonal antibodies non-crossreactive to known closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), Raven Press, 1993; Getzoff et al., Adv. in Immunol. 43: 1–98, 1988; *Monoclonal Antibodies: Principles and Practice*, Goding, J.W. (eds.), Academic Press Ltd., 1996; Benjamin et al., Ann. Rev. Immunol. 2: 67–101, 1984. Specifically binding anti-zsig81 antibodies can be detected by a number of methods in the art, and disclosed below.

A variety of assays known to those skilled in the art can be utilized to detect antibodies which bind to zsig81 proteins or polypeptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant zsig81 polypeptide.

Alternative techniques for generating or selecting antibodies useful herein include in vitro exposure of lymphocytes to zsig81 protein or peptide, and selection of antibody display libraries in phage or similar vectors (for instance, through use of immobilized or labeled zsig81 protein or peptide). Genes encoding polypeptides having potential zsig81 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. NO. 5,223,409; Ladner et al., U.S. Pat. NO. 4,946,778; Ladner et al., U.S. Pat. NO. 5,403,484 and Ladner et al., U.S. Pat. NO. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the zsig81 sequences disclosed herein to identify proteins which bind to zsig81. These "binding polypeptides" which interact with zsig81 polypeptides can be used for tagging cells; for isolating homolog polypeptides by affinity purification; they can be directly or indirectly conjugated to drugs, toxins, radionuclides and the like. These binding polypeptides can also be used in analytical methods such as for screening expression libraries and neutralizing activity, e.g., for blocking interaction between ligand and receptor, or viral binding to a receptor. The binding polypeptides can also be used for diagnostic assays for determining circulating levels of zsig81 polypeptides; for detecting or quantitating soluble zsig81 polypeptides as marker of underlying pathology or disease. These binding polypeptides can also act as zsig81 "antagonists" to block zsig81 binding and signal transduction in vitro and in vivo. These anti-zsig81 binding polypeptides would be useful for inhibiting zsig81 activity or protein-binding.

Antibodies to zsig81 may be used for tagging cells that express zsig81; for isolating zsig81 by affinity purification; for diagnostic assays for determining circulating levels of zsig81 polypeptides; for detecting or quantitating soluble zsig81 as marker of underlying pathology or disease; in analytical methods employing FACS; for screening expression libraries; for generating anti-idiotypic antibodies; and as neutralizing antibodies or as antagonists to block zsig81 in vitro and in vivo.

Antibodies or polypeptides herein may also be directly or indirectly conjugated to drugs, toxins, radionuclides, enzymes, and the like, and these conjugates used for in vivo diagnostic or therapeutic applications. Moreover, antibodies to zsig81 or fragments thereof may be used in vitro to detect denatured zsig81 or fragments thereof in assays, for example, Western Blots or other assays known in the art.

Antibodies or polypeptides herein can also be directly or indirectly conjugated to drugs, toxins, radionuclides and the like, and these conjugates used for in vivo diagnostic or therapeutic applications. For instance, polypeptides or antibodies of the present invention can be used to identify or treat tissues or organs that express a corresponding anti-complementary molecule (receptor or antigen, respectively, for instance). More specifically, zsig81 polypeptides or anti-zsig81 antibodies, or bioactive fragments or portions thereof, can be coupled to detectable or cytotoxic molecules and delivered to a mammal having cells, tissues or organs that express the anti-complementary molecule.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, Pseudomonas exotoxin, ricin, abrin, saporin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

In another embodiment, polypeptide-toxin fusion proteins or antibody-toxin fusion proteins can be used for targeted cell or tissue inhibition or ablation (for instance, to treat diseases caused by inappropriate growth of cells or tissues). Such molecule fusion proteins thus represent a generic targeting vehicle for cell/tissue-spicific delivery of generic anti-complementary-detectable/cytotoxic molecule conjugates.

Molecules of the present invention can be used to identify and isolate receptors involved in growth and differentiation of zsig81 responsive cells. For example, proteins and peptides of the present invention can be immobilized on a column and membrane preparations run over the column (*Immobilized Affinity Ligand Techniques*, Hermanson et al., eds., Academic Press, San Diego, Calif, 1992, pp.195–202). Proteins and peptides can also be radiolabeled (*Methods in Enzymol.*, vol. 182, "Guide to Protein Purification", M. Deutscher, ed., Acad. Press, San Diego, 1990, 721–737) fluorescent or photoaffinity labeled (Brunner et al., *Ann. Rev. Biochem.* 62:483–514, 1993 and Fedan et al., *Biochem. Pharmacol.* 33:1167–1180, 1984) and specific cell-surface proteins can be identified.

Polynucleotides encoding zsig81 polypeptides are useful within gene therapy applications where it is desired to increase or inhibit zsig81 activity. If a mammal has a mutated or absent zsig81 gene, the zsig81 gene can be introduced into the cells of the mammal. In one embodiment, a gene encoding a zsig81 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et-al., *J. Virol.* 63:3822–28, 1989).

In another embodiment, the zsig81 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Pat. Publication No. WO 95/07358, published Mar. 16, 1995 by Dougherty et al.; and Kuo et al., *Blood* 82:845–852, 1993. Alternatively, the vector can be introduced by lipofection in vivo using liposomes. Synthetic cationic lipids can be used to prepare liposomes for in vivo transfection of a gene encoding a marker (Feigner et al., *Proc. Natl. Acad. Sci. USA* 84:7413–17, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransrritters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–67, 1992; Wu et al., *J. Biol. Chem.* 263:14621–24, 1988.

Antisense methodology can be used to inhibit zsig81 gene transcription, such as to inhibit cell proliferation in vivo. Polynucleotides that are complementary to a segment of a zsig81-encoding polynucleotide (e.g., a polynucleotide as set forth in SEQ ID NO:1) are designed to bind to zsig81-encoding mRNA and to inhibit translation of such mRNA. Such antisense polynucleotides are used to inhibit expression of zsig81 polypeptide-encoding genes in cell culture or in a subject.

For pharmaceutical use, the proteins of the present invention are formulated for parenteral, particularly intravenous or subcutaneous, delivery according to conventional methods. Intravenous administration will be by bolus injection or infusion over a typical period of one to several hours. In general, pharmaceutical formulations will include a zsig81 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remnington: *The Science and Practice of Pharmacy*, Gennaro, ed., Mack Publishing Co., Easton, Pa., 19th ed., 1995. Therapeutic doses will generally be in the range of 0.1 to 100 μg/kg of patient weight per day, preferably 0.5–20 μg/kg per day, with the exact dose determined by the clinician according to accepted standards, taking into account the nature and severity of the condition to be treated, patient traits, etc. Determnination of dose is within the level of ordinary skill in the art. The proteins may be administered for acute treatment, over one week or less, often over a period of one to three days or may be used in chronic treatment, over several months or years. The invention is further illustrated by the following non-limiting examples.

Thus, in summary, the certain embodiments of the present invention include an isolated polypeptide comprising at least nine contiguous amino acid residues of SEQ ID) NO: 2; as well as an isolated polypeptide comprising a sequence of amino acid residues selected from the group consisting of: (a) residues 30–44 of SEQ ID NO: 2; (b) residues 56–70 of SEQ ID NO: 2; (c) residues 86–94 of SEQ ID NO: 2; and (d) residues 135–149 of SEQ ID NO: 2. Furthermore, the polypeptide may comprise residues 80–94 or 86–100 of SEQ ID NO: 2.

The isolated polypeptide of the present may also include a sequence of amino acid residues that is at least 90% identical to amino acid residues 30 to 149 of SEQ ID NO: 2, but also includes a truncated molecule comprising the sequence of amino acid residues comprises residues 5 to 156 of SEQ ID NO: 2. Further embodiments include the mature polypeptide which comprises the sequence of amino acid residues comprises residues 1 to 156 of SEQ ID NO: 2 and the primary translation product which comprises residues −17 to 156 of SEQ ID NO: 2.

In other embodiments, the present invention includes a fusion protein comprising at least two polypeptides, wherein a first polypeptide is selected from the group consisting of: (a) residues 30–44 of SEQ ID NO: 2; (b) residues 56–70 of SEQ ID NO: 2; (c) residues 86–94 of SEQ ID NO: 2; and (d) residues 135–149 of SEQ ID NO: 2. In other aspects, the a second polypeptide of the fusion protein is selected from a functional fragment of another cytokine, an antibody, or a toxin conjugate. In another aspect, the fusion protein comprising a first polypeptide and a second polypeptide, joined by a peptide bond, said first polypeptide comprises a signal sequence and a second polypeptide comprising an a sequence of amino acids as shown in SEQ ID NO: 2 from amino acid residues 30–149. Other embodiments include a fusion protein comprising a first polypeptide and a second polypeptide, joined by a peptide bond, wherein the first polypeptide is a maltose binding protein, the peptide bond is selected from the group consisting of Factor Xa cleavage site, thrombin cleavage site or enterokinase cleavage site, and the second polypeptide comprising an a sequence of amino acids as shown in SEQ ID NO: 2 from amino acid residues 30–149.

In another embodiment, the present invention includes composition comprising a sequence of amino acid residues selected from the group consisting of: (a) residues 30–44 of SEQ ID NO: 2; (b) residues 56–70 of SEQ ID NO: 2; (c) residues 86–94 of SEQ ID NO: 2; and (d) residues 135–149 of SEQ ID NO: 2; and a pharmaceutically acceptable vehicle.

Also included in the present invention are embodiments directed to an isolated polynucleotide encoding a polypeptide comprising: (a) residues 30–44 of SEQ ID NO: 2; (b) residues 56–70 of SEQ ID NO: 2; (c) residues 86–94 of SEQ ID NO: 2; or (d) residues 135–149 of SEQ ID NO: 2. In another aspect, the present invention includes an isolated polynucleotide comprising: (a) nucleotides 272–316 of SEQ ID NO: 1; (b) nucleotides 350–394 of SEQ ID NO: 1; (c) nucleotides 440–466 of SEQ ID NO: 1; or (d) nucleotides 587–631 of SEQ ID NO: 1; and a polynucleotide comprising: (a) nucleotides 139–183 of SEQ ID NO: 5; (b) nucleotides 216–261 of SEQ ID NO: 5; (c) nucleotides 307–331 of SEQ ID NO: 5; or (d) nucleotides 454–499 of SEQ ID NO: 5. Another embodiment of the present invention includes an isolated polynucleotide encoding a polypeptide comprising a sequence of amino acid residues that is at least 90% identical to amino acid residues 30 to 149 of SEQ ID NO: 2.

In another embodiment, the present invention includes expression vectors comprising the zsig81 polynucleotides described herein, and cultured cells containing those expression vectors.

Also included is a method of making a zsig 81 polypeptide comprising: culturing a cell expressing zsig81 under conditions whereby the DNA segment is expressed and the polypeptide is produced; and recovering the polypeptide.

Other embodiments include an antibody which specifically binds to a zsig81 polypeptide.

Other embodiments of the present invention include a method for expansion of hematopoietic cells and hematopoietic cell progenitors comprising culturing bone marrow or peripheral blood cells with a composition comprising an amount of zsig81 polypeptide sufficient to produce an increase in the number of hematopoietic cells in the bone marrow or peripheral blood cells as compared to bone marrow or peripheral blood cells cultured in the absence of zsig81. In addition, the hematopoietic cells and hematopoietic cell progenitors can be lymphoid or myeloid cells. Of particular interest are hematopoietic cells and hematopoietic progenitor cells that are dendritic cells.

In another embodiment, the present invention includes a method of modulating an immune response in a mammal exposed to an antigen comprising: (1) determining a level of antigen-specific antibody; (2) administering a composition comprising zsig81 polypeptide in a pharmaceutically acceptable vehicle; (3) determining a post administration level of antigen-specific antibody; (4) comparing the level of antibody in step (1) to the level of antibody in step (3), wherein a change in antibody level is indicative of modulating the immune response.

Another embodiment includes amethod of detecting the presence of zsig81 RNA in a biological sample, comprising the steps of: (a) contacting a zsig81 nucleic acid probe under hybridizing conditions with either (i) test RNA molecules isolated from the biological sample, or (ii) nucleic acid molecules synthesized from the isolated RNA molecules, wherein the probe has a nucleotide sequence of nucleic acid molecule of claim 20, or its complement; and (b) detecting the formation of hybrids of the nucleic acid probe and either the test RNA molecules or the synthesized nucleic acid molecules, wherein the presence of the hybrids indicates the presence of zsig81 in the biological sample.

Another embodiment of the present invention includes a method of detecting the presence of zsig81 in a biological sample, comprising the steps of: (a) contacting the biological sample with an antibody, or an antibody fragment, of claim 24, wherein the contacting is performed under conditions that allow the binding of the antibody or antibody fragment to the biological sample; and (b) detecting any of the bound antibody or bound antibody fragment.

In another embodiment, the present invention includes a method for stimulating antigenic response to tumor antigens comprising the steps of: (1) isolating hematopoietic cells from a mammal; (2) exposing the isolated hematopoietic cells to a tumor antigen; (3) culturing the exposed cells in a composition comprising an isolated polypeptide of at least nine contiguous amino acid residues of SEQ ID NO: 2; and (4) administering the cultured cells back to the mammal.

The invention is further illustrated by the following non-limiting examples.

EXAMPLES

Example 1

Northern Analysis of zsig81

Northern analyses were performed using Human Multiple Tissue Blots I, III and IV from Clontech (Palo Alto, Calif.). A probe was generated from a gel purified PCR product made from ZC21621 and ZC21622 (SEQ ID NOS: 10 and 11, respectively) as primers and zsig81 as template, that had been radioactively labeled with REDIPRIME™ DNA labeling kit (Amersham, Arlington Heights, Ill.) according to the manufacturer's suggestion. The probe was purified using a NUCTRAP push column (Stratagene). EXPRESSHYB™ (Clontech) solution was used for prehybridization and as a hybridizing solution for the Northern blots. Hybridization took place overnight at 65° C., and the blots were then washed in 2×SSC and 0.05% SDS at RT, followed by a wash in 0.1×SSC and 0.1% SDS at 50° C. One major transcript was observed at size of approximately 5.0 kb and 1.7 kb. The larger message was determined to contain approximately a 2.5 kb of 3' untranslated region. Signals were present in Heart and liver, with decreased expression in lung, kidney, stomach, thyroid, spinal cord, trachea, adrenal, uterus, small intestine and colon tissues. The expression of zsig81 was also examined with Human RNA Master blot (Clontech) as described above. Within heart tissue, zsig81 was localized to smooth muscle aorta using a Clontech Cardiovascular MTN Blot, and mRNA isolated from primary cultured cells.

Example 2

Mapping Human zsig81 Chromosomal Location zsig81 was mapped to human chromosome 7 using the commercially available "GeneBridge 4 Radiation Hybrid Panel" (Research Genetics, Inc., Huntsville, Ala.). The GeneBridge 4 Radiation Hybrid Panel contained DNAs from each of 93 radiation hybrid clones, plus two control DNAs (the HFL donor and the A23 recipient). Mapping was relative to the Whitehead Institute/MIT Center for Genome Research's radiation hybrid map of the human genome (the "WICGR" radiation hybrid map) which was constructed with the GeneBridge 4 Radiation Hybrid Panel.

For the mapping of zsig81 with the "GeneBridge 4 RH Panel", 20 μl reactions were set up in a 96-well microtiter plate (Stratagene, La Jolla, Calif.), and used in a "RoboCycler Gradient 96" thermal cycler (Stratagene). Each of the 95 PCR reactions consisted of 2 μl 10×KlenTaq PCR reaction buffer (CLONTECH Laboratories, Inc., Palo Alto, Calif.), 1.6 μl dNTPs mix (2.5 mM each, PERKIN-ELMER, Foster City, Calif.), 1 μl sense primer, ZC22801 (SEQ ID NO: 12), 1 μl antisense primer, ZC22802 (SEQ ID NO: 13), 2 μl "RediLoad" (Research Genetics, Inc., Huntsville, Ala.), 0.4 μl 50×Advantage KlenTaq Polymerase Mix (Clontech Laboratories, Inc.), 25 ng of DNA from an individual hybrid clone or control and ddH$_2$O for a total volume of 20 μl. The reactions were overlaid with an equal amount of mineral oil and sealed. The PCR cycler conditions were as follows: an initial 1 cycle 5 minute denaturation at 95° C., 35 cycles of a 1 minute denaturation at 95° C., 1 minute annealing at 56° C. and 1.5 minute extension at 72° C., followed by a final 1 cycle extension of 7 minutes at 72° C. The reactions were separated by electrophoresis on a 2% agarose gel (GIBCO-BRL Life Technologies, Gaithersburg, Md.).

The results showed that zsig81 maps 8.12 cR_3000 from the framework marker D7S12 on the WICGR chromosome 7 WICGR radiation hybrid map. Proximal and distal framework markers were D7S512 and WI-5478 respectively. The use of surrounding markers positions zsig81 in the 7q32-q33 region on the integrated LDB chromosome 7 map (The Genetic Location Database, University of Southhampton.

Example 3

Tissue Distribution for Mouse zsig81

A probe was constructed from full length polynucleotide sequence of mouse zsig81, and was used to identify mRNA tissue distribution on a Mouse Multiple Tissue Northern, a Mouse Dot Blot and a Mouse Embryonic Northern (Clontech). The probe was radioactively labeled with REDIPRIME™ DNA labeling kit (Amersham, Arlington Heights, Ill.) according to the manufacturer's suggestion. The probe was purified using a NUCTRAP push column (Stratagene). EXPRESSHYB™ (Clontech) solution was used for prehybridization and as a hybridizing solution for the Northern blots. Hybridization took place overnight at 65° C., and the blots were then washed in 2×SSC and 0.05% SDS at RT, followed by a wash in 0.1×SSC and 0.1% SDS at 65° C. One major transcript was observed at size of approximately 1.7 kb. Signals were present in liver, brain, heart and lung in adult tissue. In the embryonic tissue mRNA expression was highest on day 15, followed by decreased expression on day 17.

Example 4

Chromosome Mapping of Mouse zsig81

Murine zsig81 was mapped in mouse using the commercially available mouse T31 whole genome radiation hybrid (WGRH) panel (Research Genetics, Inc., Huntsville, Ala.) and Map Manager QT linkage analysis program. At P=0.0001, murine Zsig81 linked to the marker D12Mit201 with a LOD score of 13.3. D12Mit201 has been mapped at 23 cM on mouse chromosome 12. This is at the lower border of a known region of synteny or linkage conservation with the region of human chromosome 7 where the human form of zsig81 has been mapped.

The T31 WGRH panel contains DNAs from each of 100 radiation hybrid clones, plus two control DNAs (the 129aa donor and the A23 recipient). For the mapping of murine zsig81 with the T31 WGRH panel, 20 μl reactions were set up in 96-well microtiter plates (Stratagene, La Jolla, Calif.) and used in "RoboCycler Gradient 96" thermal cyclers (Stratagene). Each of the 102 PCR reactions consisted of 2 μl 10×KlenTaq PCR reaction buffer (CLONTECH Laboratories, Inc., Palo Alto, Calif.), 1.6 μl dNTPs mix (2.5 mM each, PERKIN-ELMER, Foster City, Calif.), 1 μl sense primer, ZC21229 (SEQ ID NO: 18), 1 μl antisense primer, ZC21711 (SEQ ID NO: 19), 2 μl "RediLoad" (Research Genetics, Inc., Huntsville, Ala.), 0.4 μl 50×Advantage Klen-Taq Polymerase Mix (Clontech Laboratories, Inc.), 25 ng of DNA from an individual hybrid clone or control and ddH2O for a total volume of 20 μl. The reactions were overlaid with an equal amount of mineral oil and sealed. The PCR cycler conditions were as follows: an initial 1 cycle 5 minute denaturation at 94° C., 35 cycles of a 45 seconds denaturation at 94° C., 45 seconds annealing at 62° C. and 1 minute and 15 seconds extension at 72° C., followed by a final 1 cycle extension of 7 minutes at 72° C. The reactions were separated by electrophoresis on a 2% agarose gel (Life Technologies, Gaithersburg, Md.).

Example 5

Expression Constructs for zsig81

A. Mammalian Expression Constructs

An expression plasmid containing all or part of a polynucleotide encoding zsig81 is constructed via homologous recombination. A fragment of zsig81 cDNA is isolated using PCR that includes the polynucleotide sequence from nucleotide 1 to nucleotide 472 of SEQ ID NO: 1 with flanking regions at the 5' and 3' ends corresponding to the vectors sequences flanking the zsig81 insertion point. The primers for PCR each include from 5' to 3' end: 40 bp of flanking sequence from the vector and 17 bp corresponding to the amino and carboxyl termini from the open reading frame of zsig81.

Ten μl of the 100 μl PCR reaction is run on a 0.8% LMP agarose gel (Seaplaque GTG) with 1×TBE buffer for analysis. The remaining 90 μl of PCR reaction is precipitated with the addition of 5 μl 1 M NaCl and 250 μl of absolute ethanol. The plasmid pCZR199 which has been cut with SmaI. Plasmid pCZR199 was constructed from pZP9 (deposited at the American Type Culture Collection, 10801 University Boulevard, Manassas, Va. 20110–2209, and is designated No. 98668) with the yeast genetic elements taken from pRS316 (deposited at the American Type Culture Collection, 10801 University Boulevard, Manassas, Va. 20110–2209, and is designated No. 77145) pCZR199 is a mammalian expression vector containing an expression cassette having the mouse metallothionein-1 promoter, multiple restriction sites for insertion of coding sequences, a stop codon and a human growth hormone terminator. The plasmid also has an E. coli origin of replication, a mammalian selectable marker expression unit having an SV40 promoter, enhancer and origin of replication, a DHFR gene, the SV40 terminator, as well as the URA3 and CEN-ARS sequences required for selection and replication in S. cerevisiae.

One hundred microliters of competent yeast cells (S. cerevisiae) are independently combined with 10 μl of the various DNA mixtures from above and transferred to a 0.2 cm electroporation cuvette. The yeast/DNA mixtures are electropulsed at 0.75 kV (5 kV/cm), ∞ohms, 25 μF. To each cuvette is added 600 μl of 1.2 M sorbitol and the yeast is plated in two 300 μl aliquots onto two URA-D plates and incubated at 30° C. After about 48 hours, the Ura+ yeast transformants from a single plate are resuspended in 1 ml $H_2O$ and spun briefly to pellet the yeast cells. The cell pellet is resuspended in 1 ml of lysis buffer (2% Triton X-100, 1% SDS, 100 mM NaCl, 10 mM Tris, pH 8.0, 1 mM EDTA). Five hundred microliters of the lysis mixture is added to an Eppendorf tube containing 300 μl acid washed glass beads and 200 μl phenol-chloroform, vortexed for 1 minute intervals two or three times, followed by a 5 minute spin in a Eppendorf centrifuge at maximum speed. Three hundred microliters of the aqueous phase is transferred to a fresh tube, and the DNA precipitated with 600 μl ethanol (EtOH), followed by centrifugation for 10 minutes at 4° C. The DNA pellet is resuspended in 10 μl $H_2O$.

Transformation of electrocompetent E. coli cells (DH10B, GibcoBRL) is done with 0.5–2 ml yeast DNA prep and 40 ul of DH10B cells. The cells are electropulsed at 1.7 kV, 25 μF and 400 ohms. Following electroporation, 1 ml SOC (2% Bacto' Tryptone (Difco, Detroit, Mich.), 0.5% yeast extract (Difco), 10 mM NaCl, 2.5 mM KCl, 10 mM MgC12, 10 mM MgSO4, 20 mM glucose) is plated in 250 μl aliquots on four LB AMP plates (LB broth (Lennox), 1.8% Bacto Agar (Difco), 100 mg/L Ampicillin).

Individual clones harboring the correct expression construct for zsig81 are identified by restriction digest to verify the presence of the zsig81 insert and to confirm that the various DNA sequences have been joined correctly to one another. The insert of positive clones are subjected to sequence analysis. Larger scale plasmid DNA is isolated using the Qiagen Maxi kit (Qiagen) according to manufacturer's instruction.

B. Baculovirus Expression Construct

Construction of pzBV/zSig81.CF (Baculovirus Expression Vector)

An expression vector, pZBVhzSig81, was prepared to express Human zSig81 polypeptide in insect cells. A 483 bp fragment containing sequence for Human zSig81 and the coding sequence for a c-terminal FLAG tag (SEQ ID NO: 20) and encoded BspEI and XbaI restriction sites on the 5' and 3' ends respectively, was generated by PCR amplification from a plasmid containing human zSig81 cDNA (pcDNA3d2 hzsig81-CF) using primers zc26461 (SEQ ID NO: 21) and zc26475 (SEQ ID NO: 22). The PCR reaction conditions were as follows: 25 cycles of 94° C. for 1 minute, 58° C. for 1 minute, and 72° C. for 2 minutes; 1 cycle at 72° C. for 10 minutes; followed by a 4° C. soak. The digested vector was visualized by gel electrophoreses, 0.8% agarose (EM Science, Gibbstown, N.J.) and purified using the Qiaquick Gel Extraction Kit (Qiagen, Valencia, Calif.).

About 20 ng of the purified Human zSig81 fragment was ligated, at room temperature, overnight, to about 5 ng of purified pzBV3L vector. One microliter of the ligation mixture was transformed into Electrocompetant DH10B cells (Life Technologies, Gaithersburg, Md.). Eight clones were picked and grown overnight in LB/Amp broth. Plasmids from the clones were purified by Qiaprep (Qiagen, Valencia, Calif.) mini prep kit. PCR was used to analyse clones for insert using 5' primer ZC2359 (SEQ ID NO: 23) and 3' primer ZC12581 (SEQ ID NO: 24). Each mini prep was diluted 1:100 in distilled, sterile water and 1 $\mu$l used for a 50 $\mu$l reaction (reagents from Life Technologies, Gaithersburg, Md.). Twenty microliters of each reaction was vizualized by gel electrophoresis, 1% agarose. Clone #1 was chosen to transform into cells DH10Bac to produce a "Bacmid".

Baculovirus Expression Construct of Murine zSig81 cee

A 549 bp fragment containing sequence for Murine zSig81 and encoded BamH1 and XbaI restriction sites on the 5' and 3' ends, respectively, was generated by PCR amplification from a plasmid containing Murine zSig81 cDNA (described above) using primers ZC23433 (SEQ ID NO: 25) and ZC23432 (SEQ ID NO:26) utilizing the Expand High Fidelity PCR System (Boehringer Mannheim, Indianapolis, Ind.) as per manufacturers instructions. The PCR conditions were as follows: 1 cycle of 94° C. for 4 minutes, followed by 25 cycles of 94° C. for 45 seconds, 50° C. for 45 seconds, and 72° C. for 2 minutes; 1 Cycle at 72° C. for 10 min; followed by a 10° C. soak. A small portion of the PCR product was visualized by gel electrophoresis (1% NuSieve agarose). The remainder of the fragment was precipitated and resuspended in 5 ul of $H_2O$. The fragment was then digested in a 50 $\mu$l vol. with BamH1 and XbaI restriction enzymes at 37° C. for 3 hrs, then run on agarose gel as described above. About 17.5 nanograms of the restriction digested zSig81M insert and about 53.8 ng of the corresponding vector were ligated overnight at 16° C.

Construction of Expression Vector pZBV37L hzSig81

An expression vector, pZBV37L hzSig81, was prepared to express Human zSig81 polypeptide in insect cells. A 483 bp fragment containing sequence for Human zSig81 and the coding sequence for a c-terminal glu-glu tag and encoded BspEI and XbaI restriction sites on the 5' and 3' ends respectively, was generated by PCR amplification from a plasmid containing human zSig81 cDNA (pcDNA3d2 hzsig81-CF) using primers ZC26461 (SEQ ID NO: 21) and ZC26475 (SEQ ID NO: 22). The PCR reaction conditions were as follows: 25 cycles of 94° C. for 1 minute, 58° C. for 1 minute, and 72° C. for 2 minutes; 1 cycle at 72° C. for 10 minutes; followed by a 4° C. soak. The fragment was visualized by 1% gel electrophoresis. The band was excised and purified using a QIAquick gel extraction kit (Qiagen) and ligated into a BspEI/XbaI digested baculovirus expression vector, pZBV37L. The pZBV37L vector is a modification of the pFastBac1™ (Life Technologies) expression vector, where the polyhedron promoter has been removed and replaced with the late activating Basic Protein Promoter and the EGT leader. The hzSig81 restriction digested fragment and the pZBV37L vector were ligated overnight at room temperature in a 4:1 ratio. Clones were prepared as described above.

Bacmid Production

Five mircroliters of the expression vectors described above were transformed into 50 $\mu$l DH10Bac Max Efficiency competent cells (GIBCO-BRL, Gaithersburg, Md.) according to manufacturer's specifications. A color selection was used to identify those cells having Human zsig81 encoding donor insert that had incorporated into the plasmid (referred to as a "bacmid"). Those colonies, which were white in color, were picked for analysis. Bacmid DNA was isolated from positive colonies using the QiaVac Miniprep8 system (Qiagen) according the manufacturer's directions. Clones were screened for the correct insert by amplifying DNA using primers to the transposable element in the bacmid via PCR using primers ZC447 (SEQ ID NO:27) and ZC976 (SEQ ID NO:28). The PCR reaction conditions were as follows: 35 cycles of 94° C. for 45 seconds, 50° C. for 45 seconds, and 72° C. for 5 minutes; 1 Cycle at 72° C. for 10 min.; followed by 4° C. soak. The PCR product was run on a 1% agarose gel to check the insert size. Those having the correct insert were used to transfect *Spodoptera frugiperda* (Sf9) cells.

1 $\mu$l of a positive clone was transformed into 20 $\mu$l DH10Bac Max Efficiency competent cells (GIBCO-BRL, Gaithersburg, Md.) according to the manufacturer's instruction by heat shock for 45 seconds in a 42° C. waterbath. The transformed cells were then diluted in 980 $\mu$l SOC media (2% Bacto™ Tryptone, 0.5% Bacto™ Yeast Extract, 10 ml 1 M NaCl, 1.5 mM KCl, 10 mM $MgCl_2$, 10 mM $MgSO_4$ and 20 mM glucose) out grown in a shaking incubator at 37° C. for four hours and plated onto Luria Agar plates containing 50 $\mu$g/ml kanamycin, 7 $\mu$g/ml gentanicin (Life Technologies), 10 $\mu$g/ml tetracycline, IPTG (Pharmacia Biotech) and Bluo-Gal (Life Technologies). The plated cells were incubated for 48 hours at 37° C. A color selection was used to identify those cells having human zSig81 encoding donor insert that had incorporated into the plasmid (referred to as a "bacmid"). Those colonies, which were white in color, were picked for analysis by PCR using primers to the transposable element in the bacmid with primers ZC447 (SEQ ID NO: 27) and ZC976 (SEQ ID NO: 28). The PCR reaction conditions were as follows: 35 cycles of 94° C. for 45 seconds, 50° C. for 45 seconds, and 72° C. for 5 minutes; 1 cycle at 72° C. for 10 minutes; followed by a 4° C. soak. The PCR product was run on a 1% agarose gel to check for insert size. Those clones having the correct insert size were used to transfect *Spodoptera frugiperda* (Sf9) cells.

C. Expression of Human zsig81 in *E. coli*

Construction of zsig81 -MBP Fusion Expression Vector PTAP98/zsig81

An expression plasmid containing a polynucleotide encoding part of the human zsig81 fused N-terminally to maltose binding protein (MBP) was constructed via homologous recombination. A fragment of human zsig81 cDNA (SEQ ID NO: 29) was isolated using PCR. Two primers were used in the production of the human zsig81 fragment in a PCR reaction: (1) Primer ZC22990 (SEQ ID NO: 30), containing 40 bp of the vector flanking sequence and 24 bp corresponding to the amino terminus of the human zsig81, and (2) primer ZC22991 (SEQ ID NO: 31), containing 40 bp of the 3' end corresponding to the flanking vector sequence and 21 bp corresponding to the carboxyl terminus of the human zsig81. The PCR reaction conditions were as follows: 25 cycles of 94° C. for 30 seconds, 55° C. for 30 seconds, and 72° C. for 2 minutes; followed by 4° C. soak, run in duplicate. Two ul of the 100 $\mu$l PCR reaction were run on a 1.0% agarose gel with 1×TBE buffer for analysis, and the expected band of approximately 500 bp fragment was seen. The remaining 90 $\mu$l of PCR reaction was combined with the second PCR tube precipitated with 400 $\mu$l of absolute ethanol to be used for recombining into the Sma1 cut recipient vector pTAP98 to produce the construct encoding the MBP-zsig81 fusion, as described below.

Plasmid pTAP98 was derived from the plasmids pRS316 and pMAL-c2. The plasmid pRS316 is a Saccharomyces cerevisiae shuttle vector (Hieter P. and Sikorski, R., *Genetics* 122:19–27, 1989). pMAL-C2 (NEB) is an *E. coli* expression plasmid. It carries the tac promoter driving MalE (gene encoding MBP) followed by a His tag, a thrombin cleavage site, a cloning site, and the rrnB terminator. The vector pTAP98 was constructed using yeast homologous recombination. 100 ng of EcoR1 cut pMAL-c2 was recombined with 1 μg Pvu1 cut pRS316, 1 μg linker, and 1 μg Sca1/EcoR1 cut pRS316. The linker consisted of 100 pmole of ZC19372 (SEQ ID NO: 32); 1 pmole of ZC19351 (SEQ ID NO: 33); 1 pmole of ZC19352 (SEQ ID NO: 34); and 100 pmole of ZC19371 (SEQ ID NO: 35) combined in a PCR reaction. Conditions were as follows: 10 cycles of 94° C. for 30 seconds, 50° C. for 30 seconds, and 72° C. for 30 seconds; followed by 4° C. soak. PCR products were concentrated via 100% ethanol precipitation.

One hundred microliters of competent yeast cells (*S. cerevisiae*) were combined with 10 μl of a mixture containing approximately 1 μg of the human zsig81 insert, and 100 ng of SmaI digested pTAP98 vector, and transferred to a 0.2 cm electroporation cuvette. The yeast/DNA mixture was electropulsed at 0.75 kV (5 kV/cm), infinite ohms, 25 μF. To each cuvette was added 600 μl of 1.2 M sorbitol. The yeast was then plated in two 300 μl aliquots onto two –URA D plates and incubated at 30° C.

After about 48 hours, the Ura+ yeast transformants from a single plate were resuspended in 1 ml $H_2O$ and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 μl acid washed glass beads and 200 μl phenol-chloroform, vortexed for 1 minute intervals two or three times, followed by a 5 minute spin in a Eppendorf centrifuge at maximum speed. Three hundred microliters of the aqueous phase was transferred to a fresh tube, and the DNA precipitated with 600 μl ethanol (EtOH), followed by centrifugation for 10 minutes at 4° C. The DNA pellet was resuspended in 100 μl $H_2O$.

Transformation of electrocompetent *E. coli* cells (MC1061, Casadaban et. al. *J. Mol. Biol.* 138, 179–207) was done with 1 μl yeast DNA prep and 40 μl of MC1061 cells. The cells were electropulsed at 2.0 kV, 25 μF and 400 ohms. Following electroporation, 0.6 ml SOC (2% BactoÎ Tryptone (Difco, Detroit, Mich.), 0.5% yeast extract (Difco), 10 mM NaCl, 2.5 mM KCl, 10 mM MgCl2, 10 mM MgSO4, 20 mM glucose) was plated in one aliquot on LB AMP plates (LB broth (Lennox), 1.8% Bacto™ Agar (Difco), 100 mg/L Ampicillin).

Individual clones harboring the correct expression construct for human zsig81 were identified by PCR screening using oligonucleotides ZC22990 (SEQ ID NO: 30) and ZC22991 (SEQ ID NO: 31). Reaction conditions were as follows: 25 cycles of 94° C. for 30 seconds; 50° C. for 30 seconds; 72° C. for one minute; then followed by a 4° C. soak. Of the positive clones producing a band around 500 bp as seen using agarose gel electrophoresis, 4 were then further screened by expression. Cells were grown in Superbroth II (Becton Dickinson) with 100 μg/ml of ampicillin overnight. 50 μl of the overnight culture was used to inoculate 2 ml of fresh Superbroth II+100 μg/ml ampicillin.

Cultures were grown at 37° C., shaking for 2 hours. 1 ml of the culture was induced with 1 mM IPTG. 2–4 hours later the 250 μl of each culture was mixed with 250 μl acid washed glass beads and 250 μl Thorner buffer with 5% BME and dye(8M urea, 100 mM Tris pH7.0, 10% glycerol, 2 mM EDTA, 5% SDS). Samples were vortexed for one minute and heated to 65° C. for 10 minutes. 20 μl were loaded per lane on a 4%–12% PAGE gel (NOVEX). Gels were run in 1×MES buffer. The positive clones were subjected to sequence analysis. The correct clone was designated pTAP139.

Example 6

Expression of zsig81

A. Mammalian Expression of zsig81

CHO DG44 (Chasin et al., *Som. Cell. Molec. Genet.* 12:555–666, 1986) are plated in 10 cm tissue culture dishes and allowed to grow to approximately 50 to 70% confluency overnight at 37° C., 5% $CO_2$, in Ham's F12/FBS media (Ham's F12 medium, (Gibco BRL, Gaithersburg, Md.), 5% fetal bovine serum (Hyclone, Logan, Utah), 1% L-glutamine (JRH Biosciences, Lenexa, Kans.), 1% sodium pyruvate (Gibco BRL)). The cells are then transfected with the plasmid zsig81/pCZR199, using Lipofectamine™ (Gibco BRL), in serum free (SF) media formulation (Ham's F12, 10 mg/ml transferrin, 5 mg/ml insulin, 2 mg/ml fetuin, 1% L-glutamine and 1% sodium pyruvate). zlipo3/pCZR199 is diluted into 15 ml tubes to a total final volume of 640 μl with SF media. 35 μl of Lipofectamine™ (Gibco BRL) is mixed with 605 μl of SF medium. The Lipofectamine™ mix is added to the DNA mix and allowed to incubate approximately 30 minutes at room temperature. Five milliliters of SF media is added to the DNA:Lipofectamine™ mixture. The cells are rinsed once with 5 ml of SF media, aspirated, and the DNA:Lipofectamine™ mixture is added. The cells are incubated at 37° C. for five hours, then 6.4 ml of Ham's F12/10% FBS, 1% PSN media is added to each plate. The plates are incubated at 37° C. overnight and the DNA:Lipofectamine™ mixture is replaced with fresh 5% FBS/ Ham's media the next day. On day 2 post-transfection, the cells are split into the selection media (nucleoside-free Alpha MEM/dialyzed FBS media with the addition of 50 nM methotrexate (Sigma Chemical Co., St. Louis, Mo.)) in 150 mm plates at 1:10, 1:20 and 1:50. The cells are refed at day 5 post-transfection with fresh selection media. Approximately 10 days post-transfection, two 150 mm culture dishes of methotrexate resistant colonies from each transfection are trypsinized and the cells are pooled and plated into a T-162 flask and transferred to large scale culture for scale-up and dilution cloning.

Cells are plated for subcloning at a density of 0.5, 1 and 5 cells per well in 96 well dishes in selection medium and allowed to grow out for approximately two weeks. The wells are checked for evaporation of medium and brought back to 200 μl per well as necessary during this process. When a large percentage of the colonies in the plate are near confluency, 100 μl of medium is collected from each well for analysis by dot blot, and the are fed with fresh selection medium. The supernatant is applied to nitrocellulose filter in a dot blot apparatus and the filter is treated at 100° C. in a vacuum oven to denature the protein. The filter was incubated in 625 mM tris glycine, pH 9.1, 5 mM βmercaptoethanol, at 65° C., 10 minutes, then in 2.5% non-fat dry milk Western A Buffer (0.25% gelatin, 50 mM TrisHCl pH 7.4, 150 mM NaCl, 5 mM EDTA, 0.05% Igepal CA-630) overnight at 4° C. on a rotating shaker. The filter was incubated with the antibody-HRP conjugate in 2.5% non-fat dry milk Western A buffer for 1 hour at room temperature on a rotating shaker. The filter was washed three times at room temperature in PBS plus 0.01% Tween 20, 15 minutes per wash. The filter was developed with ECL reagent according to manufacturer's directions (Amersham, Arlington Heights, Ill.) and exposed to film (Hyperfilm ECL, (Amersham) approximately 5 minutes. Positive clones are trypsinized from the 96 well dish and transferred to 6 well dishes in selection .medium for scaleup and analysis by Western blot.

B. Yeast Expression

Expression of zsig81 in *Pichia methanolica* utilizes the expression system described in commonly-assigned WIPO publication WO 97/17450. An expression plasmid containing all or part of a polynucleotide encoding zsig81 is constructed via homologous recombination.

An expression vector is built from pCZR190 to express N-terminal tagged zsig81 polypeptides. The pCZR190 vector contains the AUG1 promoter, followed by the aFpp leader sequence and an amino-terminal peptide tag (FLAG; SEQ ID NO: 20), followed by a blunt-ended Sma I restriction site, a translational STOP codon, followed by the AUG1 terminator, the ADE2 selectable marker, and finally the AUG1 3' untranslated region. Also included in this vector are the URA3 and CEN-ARS sequences required for selection and replication in *S. cerevisiae*, and the AmpR and colE1 ori sequences required for selection and replication in *E. coli*. For each construct two linkers are prepared, and along with zsig81, are homologously recombined into the yeast expression vectors described herein.

One hundred microliters of competent yeast cells (*S. cerevisiae*) are independently combined with 10 μl of the various DNA mixtures from above and transferred to a 0.2 cm electroporation cuvette. The yeast/DNA mixtures are electropulsed at 0.75 kV (5 kV/cm), ∞ohms, 25 μF. To each cuvette is added 600 μl of 1.2 M sorbitol and the yeast is plated in two 300 μl aliquots onto two URA-D plates and incubated at 30° C.

After about 48 hours, the Ura+yeast transformants from a single plate are resuspended in 1 ml H$_2$O and spun briefly to pellet the yeast cells. The cell pellet is resuspended in 1 ml of lysis buffer (2% Triton X-100, 1% SDS, 100 mM NaCl, 10 mM Tris, pH 8.0, 1 mM EDTA). Five hundred microliters of the lysis mixture is added to an Eppendorf tube containing 300 μl acid washed glass beads and 200 μl phenol-chloroform, vortexed for 1 minute intervals two or three times, followed by a 5 minute spin in a Eppendorf centrifuge at maximum speed. Three hundred microliters of the aqueous phase is transferred to a fresh tube, and the DNA precipitated with 600 μl ethanol (EtOH), followed by centrifugation for 10 minutes at 4° C. The DNA pellet is resuspended in 100 μl H$_2$O.

Transformation of electrocompetent *E. coli* cells (DH10B, GibcoBRL) is done with 0.5–2 μl yeast DNA prep and 40 ul of DH10B cells. The cells is electropulsed at 2.0 kV, 25 mF and 400 ohms. Following electroporation, 1 ml SOC (2% Bacto' Tryptone (Difco, Detroit, Mich.), 0.5% yeast extract (Difco), 10 mM NaCl, 2.5 mM KCl, 10 mM MgCl2, 10 mM MgSO4, 20 mM glucose) is plated in 250 μl aliquots on four LB AMP plates (LB broth (Lennox), 1.8% Bacto' Agar (Difco), 100 mg/L Ampicillin).

Individual clones harboring the correct expression construct for zsig81 are identified by PCR analysis or restriction digest to verify the presence of the zsig81 insert and to confirm that the various DNA sequences have been joined correctly to one another. The insert of positive clones are subjected to sequence analysis. Larger scale plasmid DNA is isolated using the Qiagen Maxi kit (Qiagen) according to manufacturer's instruction, and the DNA is digested with Not I to liberate the Pichia-zsig81 expression cassette from the vector backbone. The Not I-restriction digested DNA fragment is then transformed into the *Pichia methanolica* expression host, PMAD16. This is done by mixing 100 ml of prepared competent PMAD16 cells with 10 μg of Not I restriction digested zsig81 and transferred to a 0.2 cm electroporation cuvette. The yeast/DNA mixture is electropulsed at 0.75 kV, 25 mF, infinite ohms. To the cuvette is added 1 ml of 1×Yeast Nitrogen Base and 500 ml aliquots are plated onto two ADE DS (0.056% -Ade-Trp-Thr powder, 0.67% yeast nitrogen base without amino acids, 2% D-glucose, 0.5% 200×. tryptophan, threonine solution, and 18.22% D-sorbitol) plates for selection and incubated at 30° C. Clones are picked and screened via Western blot for high-level zsig81 expression and fermented.

C. Baculovirus Expression of zsig81

Expression of pzBV/zSig81.CF (Baculovirus Expression Vector)

An expression vector, pZBVhzSig81, was prepared to express Human zSig81 polypeptide in insect cells as described in Example 2B. Sf9 cells were seeded at 1 million cells per 35 mm plate and allowed to attach for 1 hour at 27° C. Five microliters of bacmid DNA was diluted with 100 μl Sf-900 II SFM (Life Technologies). 25 μl of CellFECTIN™ Reagent (Life Technologies) was diluted with 100 μl Sf-900 II SFM. The bacmid DNA and lipid solutions were gently mixed and incubated 30–45 minutes at room temperature. The media from one plate of cells were aspirated, the cells were washed 1× with 2 ml fresh Sf-900 II SFM media. Eight hundred microliters of Sf-900 II SFM was added to the lipid-DNA mixture. The wash media was aspirated and the DNA-lipid mix added to the cells. The cells were incubated at 27° C. for 24 hours. The DNA-lipid mix was aspirated and 2 ml of Sf-900 II media was added to each plate. The plates were incubated at 27° C., 90% humidity, for 5 days, after which the virus was harvested.

Sf9 cells were seeded as above and 200 μl of post transfection supernatant was added and cultures were allowed to proceed for 72 hrs after which time the virus was harvested.

Sf9 cells were seeded as above and 20 μl of the Primary viral stock was added. Cultures were incubated at 27° C. for 9 days, after which time the virus was harvested according to standard methods known in the art.

20 μl of Secondary Amplified virus stock was placed on SF9s at 500,000 cells per well in 50 mls of SF900H media in a 250 ml vol shake flask for 96 hrs, and virus was harvested as above.

Presence of predicted molecular weight protein in the cell lysate was determined by western analysis using anti-FLAG primary monoclonal antibody and goat anti-mouse HRP secondary. Material was also immunoprecipatated using anti-EE antibody conjugated to sepharose and submitted for n-terminal signal peptidase cleavage point analysis.

Baculovirus Expression of Murine zSig 81 cee

An expression vector, was prepared to express Murine zSig81 polypeptides in insect cells as described in Example 5. A 50 ml culture of Trichoplusia ni (Hi5) cells at 2.2×10$^6$ cells/ml was infected with 22 ml of primary amplification supernatant. The infection culture was allowed to progress for 48 hrs and the cells pelleted via centrifugation and frozen at −20° C. A hypotonic lysis of the pellet was performed as follows: pellet thawed; 2.5 ml of lysis buffer (0.02M Tris-HCl ph8.3, 0.001M EDTA, ,001 DTT, 1 mM Pefabloc, 500 nM Aprotonin, 4 μM Leupeptin, 4 μM E-64, 1% NP-40) was used to resuspend the cells. Lysis was allowed to progress at 4° C. for 15 min. The cellular debris was spun out, and the supernatant was collected and incubated with sepharose beads w/conjugated anti-EE antibody. The beads were washed and submitted to for signal peptidase cleavage point determination.

Sample Preparation: Murine zsig81 CEE samples were supplied on anti-EE beads. The beads were placed in reducing SDS PAGE sample buffer and on a boiling water bath before running on SDS PAGE. (Novex SDS PAGE system and supplies, 4–12% bis-tris MES NuPAGE). These were electrotransferred to Novex PVDF membrane, and then coomassie blue stained. Corresponding anti-EE westerns were performed to identify which bands to excise for N-terminal protein sequencing.

Human zsig81 CF samples were supplied on anti-FLAG beads. The beads were placed in both reducing and non-reducing SDS PAGE sample buffer and on a boiling water bath before running on SDS PAGE. (Novex SDS PAGE system and supplies, 4–12% bis-tris MES NuPAGE). These were electrotransferred to Novex PVDF membrane, and then coomassie blue stained. Corresponding anti-FLAG westerns were performed to identify which bands to excise for N-terminal protein sequencing.

N-terminal sequence analyses were performed on a Models 476A and 494 Protein Sequencer Systems from Perkin Elmer Applied Biosystems Division, Foster City, Calif. Data analysis was performed with Applied Biosystems Model 610A Data Analysis System for Protein Sequencing, version 2.1a (Applied Biosystems Inc. Foster City, Calif.). Most supplies and reagents used were from Applied Biosystems Inc.

The predicted mature start is at Ser18 of the human precursor form and at Thr18 of the murine precursor form.

For the murine form from BV with the C-terminal EE tag (SEQ ID NO: 36) one experimental mature start is at Ser20 of the precursor form. There is an indication that another experimental mature start at Arg22 is present. This second call is ambiguous due to contaminating histone sample.

Human zsig81CF from BV resulted in an experimental mature start at Ser18 of the precursor sequence which is also the predicted mature start. Within this sample there were also minor amounts of precursor sequence starting at His21 and Met 1.

Expression of Arg22 Human zSig81

Based on these results and the observation that homology of human and murine zSig81 are divergent from the initiating methinonine and then converge at arginine 22 led us to prepare baculovirus expression vectors fusing the ecdysteroid UDP-glucasyltransferase (EGT) leader sequence to arginine 22 of both human and murine zSig81.

Sequence analysis of the human zSig81.CEE revealed that all of the zSig81 protein was processed as predicted, leaving Arg 22 as the amino terminal amino acid of the mature peptide. PAGE and western analysis indicate mature zSig81.CEE as isolated, is approximately 50% disulfide linked dimer and 50% monomer.

Bacterial Expression of Human zsig81.

One microliter of pTAP139 sequencing DNA was used to transform strain W3110 (ATCC No. 27325). The cells were electropulsed at 2.0 kV, 25 μF and 400 ohms. Following electroporation, 0.6 ml SOC (2% Bactoë Tryptone (Difco, Detroit, Mich.), 0.5% yeast extract (Difco), 10 mM NaCl, 2.5 mM KCl, 10 mM MgCl2, 10 mM MgSO4, 20 mM glucose) was plated in one aliquot on LB AMP plates (LB broth (Lennox), 1.8% Bacto™ Agar (Difco), 100 mg/L Ampicillin).

Individual colonies were expressed. Cells were grown in Superbroth II (Becton Dickinson) with 100 μg/ml of ampicillin overnight. 50 μl of the overnight culture was used to inoculate 2 ml of fresh Superbroth II+100 μg/ml ampicillin. Cultures were grown at 37° C., shaking for 2 hours. 1 ml of the culture was induced with 1 mM IPTG. 2–4 hours later the 250 μl of each culture was mixed with 250 μl acid washed glass beads and 250 μl Thorner buffer with 5% BME and dye (8M urea, 100 mM Tris pH7.0, 10% glycerol, 2 mM EDTA, 5% SDS). Samples were vortexed for one minute and heated to 65° C. for 10 minutes. 20 μl were loaded per lane on a 4%–12% PAGE gel (NOVEX). Gels were run in 1× MES buffer Example 7

Protein Purification of zsig81

Unless otherwise noted, all operations will be carried out at 4° C. A total of 25 liters of conditioned medium from chinese hamster ovary (CHO) cells or baby hamster kidney cells (BHK) is be sequentially sterile filtered through a 4 inch, 0.2 mM Millipore (Bedford, Mass.) OptiCap capsule filter and a 0.2 mM Gelman (Ann Arbor, Mich.) Supercap 50. The material is then be concentrated to about 1.3 liters using a Millipore ProFlux A30 tangential flow concentrator fitted with a 3000 kDa cutoff Amicon (Bedford, Mass.) S10Y3 membrane. The concentrated material is sterile-filtered with the Gelman filter again as described above. A mixture of protease inhibitors is added to the concentrated conditioned medium to final concentrations of 2.5 mM ethylenediaminetetraacetic acid (EDTA, Sigma Chemical Co. St. Louis, Mo.), 0.001 mM leupeptin (Boehringer-Mannheim, Indianapolis, Ind.), 0.001 mM pepstatin (Boehringer-Mannheim) and 0.4 mM Pefabloc (Boehringer-Mannheim).

Generic screening for protein capture is carried out using a BioCad 700E, Sprint, or Vision workstation (PE Biosystems, Framingham, Mass.) using the column screening module according to the manufacturer's instructions. A 50 ml sample of the concentrated CHO conditioned medium is brought to the appropriate pH by in-line dilution with screening buffer (25 mM Tris, 25 mM MOPS, 25 mM MES, and 25 mM acetate adjusted to the appropriate pH as described below) and pumped sequentially at a flow rate of 2–5 ml/min onto a 1.7 ml Poros HS (PE Biosystems) column equilibrated at pH 4.0, 5.0, and 6.0, onto a 1.7 ml Poros HQ (PE Biosystems) column equilibrated at pH 7.0, 8.0, and 9.0, onto a 1.7 ml Poros HE (PE Biosystems) column at pH 7.4, and onto a 1.7 ml Poros HP2 (PE Biosystems) column equilibrated at pH 7.4 and 1.0–4.0 M NaCl. After sample application, each column is washed with the appropriate equilibration buffer and when the absorbance at 280 nm of the effluent is below 0.05, the Poros HS, HQ, and HE columns are eluted stepwise with 1.0–2.0 M NaCl. The Poros HP2 column is eluted stepwise with water. 1.0 ml fractions is collected and the target protein in each of the column eluates is identified by the automated proteolysis-mass spec procedure described below. Positive identities are confirmed by SDS-PAGE analysis of each eluate fraction according to standard procedures.

Once the binding conditions are established for a particular protein, these conditions are used for its large batch purification. Purity at each step of the purification is assessed by SDS-PAGE and Western blotting with anti-zsig81 antibodies directed against the MBP-fusion of the target protein.

Proteins eluted as described above are detected independent of western blotting or other antibody related strategies. The presence of the desired protein is determined as either a single component or in a complex mixture by analysis of the eluate of a column, collected over several fractions and resulting in a relative quantitation of the amount of zsig81 protein present in each fraction.

The system uses a stepwise combination of proteolytic digestion of protein samples (module 1), chromatographic separation (module 2) and mass spectral analysis (module 3) of the digestion mixture. The three modules of this process are used individually for analysis of protein samples in a manual fashion, resulting in maximal data output, or in the stepwise process of 3 modules in a fully automated set-up, resulting in maximal high throughput.

In the automated set-up, module 1 and 2 are combined in the INTEGRAL Workstation (PE Biosystems, Farmington, Mass.) which is on-line connected to module 3. Module 3 is an LCQ ion-trap mass spectrometer (Finnigan, San Jose, Calif.) equipped with an electrospray source.

To maximize data output, module 1 and 2 are separated and the proteolytic digestion of samples is removed from the automated procedure. A MAGIC HPLC system (Michrom BioResources, Inc., Auburn, Calif.) serves as module 2. Samples are injected either manually or via autoinjector. Module 3 is an LCQ ion-trap mass spectrometer equipped with an electrospray source. Module 3 is on-line connected to module 2.

Module 1: Proteolytic Digestion

Typically, samples are proteolytically digested with trypsin, however, other proteases with defined specificity can be utilized. If necessary, samples are filtered or centrifuged to remove aggregates or other potential particulate matter. In some cases, samples are applied to a size exclusion step by filtration prior to analysis to simplify the resulting digestion mixture and make the identification of peptides related to the desired protein easier. All necessary buffer adjustments are made before proteolytic digestion.

In the automated set-up, the samples are digested on-line on an immobilized trypsin column (PE Biosystems). The injection onto the column is done using the INTEGRAL autoinjector and the resulting peptides are chromatographically separated on module 2.

In the manual approach, samples are digested overnight in solution and injected by hand or via autoinjector onto module 2.

Module 2: Chromatographic Separation

The chromatographic separation of peptides is carried out on a 1 mm ID reverse phase (POROS, PE Biosystems) column (LC-Packings, San Francisco, Calif.). Typically, the column is eluted with a trifluoroacetic acid (TFA)/water, TFA/acetonitrile gradient and the elution of peptides is monitored by UV. In the automated, as well as the- manual approach, peptides are analyzed on-line on module 3 as they elute off the column.

Module 3: Mass Spectral Analysis

The mass spectral analysis of peptides is carried out using the "triple play" approach. First, full mass range scans are taken as the column eluate is sprayed into the source of the mass spectrometer. If a signal above a predetermined intensity threshold is detected, the instrument switches to a setting which provides a high resolution mass measurement, followed by an MS/MS scan.

The MS/MS scan provides the fragmentation pattern which is used to derive the primary sequence of the peptide. Peptide sequences are then used for the identification of the protein. Typically, primary sequence and the nature of the protein is determined using the search algorithm SEQUEST (Finnigan). Mass spectral sample and data analysis are carried out automatically. If necessary, data interpretation to derive peptide sequences is done manually and the protein is identified using a variety of standard database search algorithms.

Ion intensities and number of peptides detected for one protein are used to determine the relative abundance of this protein in different fractions.

If the mass spectral analysis is carried out on all ions observed leading to the analysis of all components in the digestion mixture. In order to simplify the analysis, the mass spectrometer is typically set to analyze only those ions which can be expected following the proteolysis of the desired protein. Through this filter, the analysis becomes amenable to very complex mixtures which potentially contains the desired protein as only a minor component.

Purification from Insect Cells Sf9

Sf9 cells infected with the expression virus, pzBV37Lhzsig81, , from one liter of culture, expressing hzSig81.CEE were lysed by incubation in 150 mM NaCl, 50 mM Tris (pH 8.0), 1% NP-40, COMPLETE™ protease inhibitor cocktail (Roche, Indianapolis, Ind.) for one hour at 4° C. The lysate was cleared of cellular debris by spinning in a centrifuge at 550×g for 15 minutes at 4° C. The supernatent was combined with 4 mL anti-EE monoclonal antibody/sepharose resin and incubated overnight at 4° C. The antibody-resin was collected, washed with 20 column volumes of ice cold PBS, and human zsig81.CEE was eluted with 1 mL 100 mM glycine pH 2.0. The glycine eluate was neutralized with 100 mL Tris pH 8.8 and then dialyzed against 8L of PBS. The dialyzed eluate contained 500 mg/mL protein of which, by PAGE and western analysis, approximately 70% was human zsig81.CEE (zsig81 concentration approximately 350 mg/mL).

Sequence analysis of the human zSig81.CEE revealed that all of the zSig81 protein was processed as predicted, leaving Arg 22 as the amino terminal amino acid of the mature peptide. PAGE and western analysis indicate mature zSig81.CEE as isolated, is approximately 50% disulfide linked dimer and 50% monomer.

Example 8

Adenoviral Expression of zsig81

The protein coding region of zsig81 is amplified by PCR using primers that added FseI and AscI restriction sties at the 5' and 3' termini respectively. PCR primers are used with a template containing the full-length zsig81 cDNA in a PCR reaction as follows: one cycle at 95° C. for 5 minutes; followed by 15 cycles at 95° C. for 1 min., 58° C. for 1 min., and 72° C. for 1.5 min.; followed by 72° C. for 7 min.; followed by a 4° C. soak. The PCR reaction product is loaded onto a 1.2% (low melt) SeaPlaque GTG (FMC, Rockland, Me.) gel in TAE buffer. The zsig81 PCR product is excised from the gel and purified using the QIAquick™ PCR Purification Kit gel cleanup kit as per kit instructions (Qiagen). The PCR product is then digested, phenol/chloroform extracted, EtOH precipitated, and rehydrated in 20 ml TE (Tris/EDTA pH 8). The zsig81 fragment is then ligated into the cloning sites of the transgenic vector pTG12-8 (See, description herein) and transformed into DH10B competent cells by electroporation. Clones containing zsig81 are identified by plasmid DNA miniprep followed by digestion. A positive clone is confirmed by direct sequencing.

The zsig81 cDNA is released from a TG12-8 vector using FseI and AscI enzymes. The cDNA is isolated on a 1% low melt SeaPlaque GTG™ (FMC, Rockland, Me.) gel, and is then excised from the gel. The gel slice is melted at 70° C., extracted twice with an equal volume of Tris buffered phenol, and EtOH precipitated. The DNA is resuspended in 10 µl H$_2$O.

The zsig81 cDNA is cloned into the FseI-AscI sites of a modified pAdTrack CMV (He et al., PNAS 95:2509–2514, 1998). This construct contains the GFP marker gene. The CMV promoter driving GFP expression was replace with the SV40 promoter and the SV40 polyadenylation signal has been replaced with the human growth hormone.polyadenylation signal. In addition, the native polylinker was replaced with FseI, EcoRV, and AscI sites. This modified form of pAdTrach CMV was named pZyTrack. Ligation is performed using the Fast-Link™ DNA ligation and screening kit (Epicentre Technologies, Madison, Wis.). In order to linearize the plasmid, approximately 5 µg of the pZyTrack zsig81 plasmid is digested with PmeI. Approximately 1 µg of the linearized plasmid is cotransformed with 200 ng of supercoiled pAdEasy (He et al., supra.) into BJ5183 cells. The co-transformation is done using a Bio-Rad Gene Pulser at 2.5 kV, 200 ohms and 25 mFa. The entire co-transformation is plated on 4 LB plates containing 25 µg/ml kanamycin. The smallest colonies are picked and expanded in LB/kanamycin and recombinant adenovirus DNA identified by standard DNA miniprep procedures. Digestion of the recombinant adenovirus DNA with FseI-AscI confirms the presence of zsig81. The recombinant adenovirus miniprep DNA is transformed into DH10B competent cells and DNA prepared using a Qiagen maxi prep kit as per kit instructions.

Approximately 5 µg of recombinant adenoviral DNA is digested with Pacd enzyme (New England Biolabs) for 3 hours at 37° C. in a reaction volume of 100 µl containing 20–30 U of PacI. The digested DNA is extracted twice with an equal volume of phenol/chloroform and precipitated with ethanol. The DNA pellet is resuspended in 10 µl distilled water. A T25 flask of QBI-293A cells (Quantum Biotechnologies, Inc. Montreal, Qc. Canada), inoculated the day before and grown to 60–70% confluence, are transfected with the PacI digested DNA. The PacI-digested DNA is diluted up to a total volume of 50 µl with sterile HBS (150 mM NaCl, 20 mM HEPES). In a separate tube, 20 µl DOTAP (Boehringer Mannheim, 1 mg/ml) is diluted to a total volume of 100 µl with HBS. The DNA is added to the DOTAP, mixed gently by pipeting up and down, and left at room temperature for 15 minutes. The media is removed from the 293A cells and washed with 5 ml serum-free MEM-alpha (Gibco BRL) containing 1 mM Sodium Pyruvate (GibcoBRL), 0.1 mM MEM non-essential amino acids (GibcoBRL) and 25 mM HEPES buffer (GibcoBRL). 5 ml of serum-free MEM is added to the 293A cells and held at 37° C. The DNA/lipid mixture is added drop-wise to the T25 flask of 293A cells, mixed gently and incubated at 37° C. for 4 hours. After 4 h the media containing the DNA/lipid mixture is aspirated off and replaced with 5 ml complete MEM containing 5% fetal bovine serum. The transfected cells are monitored for Green Fluorescent Protein (GFP) expression and formation of foci, i.e., viral plaques.

Seven days after transfection of 293A cells with the recombinant adenoviral DNA, the cells expressing the GFP protein start to form foci. These foci are viral "plaques" and the crude viral lysate is collected by using a cell scraper to collect all of the 293A cells. The lysate is transferred to a 50 ml conical tube. To release most of the virus particles from the cells, three freeze/thaw cycles are done in a dry ice/ethanol bath and a 37° C. waterbath.

The crude lysate is amplified (Primary (1°) amplification) to obtain a working "stock" of zsig81 rAdV lysate. Ten 10 cm plates of nearly confluent (80–90%) 293A cells are set up 20 hours previously, 200 µl of crude rAdV lysate added to each 10 cm plate and monitored for 48 to 72 hours looking for CPE under the white light microscope and expression of GFP under the fluorescent microscope. When all of the 293A cells show CPE (Cytopathic Effect) this 1° stock lysate is collected and freeze/thaw cycles performed as described under Crude rAdV Lysate.

Secondary (2°) Amplification of zsig81 rAdV is obtained as follows: Twenty 15 cm tissue culture dishes of 293A cells are prepared so that the cells were 80–90% confluent. All but 20 mls of 5% MEM media is removed and each dish is inoculated with 300–500 µl 1° amplified rAdv lysate. After 48 hours the 293A cells are lysed from virus production and this lysate is collected into 250 ml polypropylene centrifuge bottles and the rAdV purified.

NP-40 detergent is added to a final concentration of 0.5% to the bottles of crude lysate in order to lyse all cells. Bottles are placed on a rotating platform for 10 min. agitating as fast as possible. The debris is pelleted by centrifugation at 20,000 ×G for 15 minutes. The supernatant is transferred to 250 ml polycarbonate centrifuge bottles and 0.5 volumes of 20% PEG8000/2.5 M NaCl solution added. The bottles are shaken overnight on ice. The bottles are centrifuged at 20,000×G for 15 minutes and supernatant discarded into a bleach solution. The white precipitate forms in two vertical lines along the wall of the bottle on either side of the spin mark and is precipitated virus/PEG. Using a sterile cell scraper, the precipitate from 2 bottles is resuspended in 2.5 ml PBS. The virus solution is placed in 2 ml microcentrifuge tubes and centrifuged at 14,000×G in the microfuge for 10 minutes to remove any additional cell debris. The supernatant from the 2 ml microcentrifuge tubes is transferred into a 15 ml polypropylene snapcap tube and adjusted to a density of 1.34 g/ml with cesium chloride (CsCl). The volume of the virus solution is estimated and 0.55 g/ml of CsCl added. The CsCl is dissolved and 1 ml of this solution weighed. The solution is transferred polycarbonate thick-walled centrifuge tubes 3.2 ml (Beckman) and spun at 80,000 rpm (348,000×G) for 3–4 hours at 25° C. in a Beckman Optima TLX microultracentrifuge with the TLA-100.4 rotor. The virus forms a white band. Using wide-bore pipette tips, the virus band is collected.

The virus from the gradient will have a large amount of CsCl, which must be removed before it can be used on cells. Pharmacia PD-10 columns prepacked with Sephadex G-25M (Pharmacia) are used to desalt the virus preparation. The column is equilibrated with 20 ml of PBS. The virus is loaded and allowed to run into the column. Five ml of PBS is added to the column and fractions of 8–10 drops collected. The optical densities of 1:50 dilutions of each fraction is determined at 260 nm on a spectrophotometer, and a clear absorbance peak identified. These fractions are pooled and the optical density (OD) of a 1:25 dilution determined. A formula is used to convert OD into virus concentration: (OD at 260 nm)(25)(1.1×10$^{12}$)=virions/ml. The OD of a 1:25 dilution of the zsig81 rAdV was 0.221, giving a virus concentration of 6×10$^{12}$ virions/ml.

To store the virus, glycerol is added to the purified virus to a final concentration of 15%, mixed gently and stored in aliquots at −80° C.

A protocol developed by Quantum Biotechnologies, Inc. (Montreal, Qc. Canada) is followed to measure recombinant virus infectivity. Briefly, two 96-well tissue culture plates are seeded with $1\times10^4$ 293A cells per well in MEM containing 2% fetal bovine serum for each recombinant virus to be assayed. After 24 hours 10-fold dilutions of each virus from $1\times10^{-2}$ to $1\times10^{-14}$ are made in MEM containing 2% fetal bovine serum. 100 μl of each dilution is placed in each of 20 wells. After 5 days at 37° C. , wells are read either positive or negative for Cytopathic Effect (CPE) and a value for "Plaque Forming Units/ml" (PFU) is calculated.

$TCID_{50}$ formulation used is as per Quantum Biotechnologies, Inc., above. The titer (T) is determined from a plate where virus used is diluted from $10^{-2}$ to $10^{-14}$, and read 6 days after the infection. At each dilution a ratio (R) of positive wells for CPE per the total number of wells is determined.

To Calculate titer of the undiluted virus sample: the factor, "F"=1+d(S-0.5); where "S" is the sum of the ratios (R); and "d" is Log10 of the dilution series, for example, "d" is equal to 1 for a ten-fold dilution series. The titer of the undiluted sample is $T=10^{(1+F)}=TCID_{50}/ml$. To convert $TCID_{50}/ml$ to pfu/ml, 0.7 is subtracted from the exponent in the calculation for titer (T). The zsig81 adenovirus had a titer of $7.1\times10^{10}$ pfu/ml.

Example 9

Transgenic Expression

Transgenic animals expressing zsig81 genes are made using adult, (, 2–8 months, (C57BL/6×C3H/N f1Taconic Farms)), prepubescent fertile females (donors) (C57BL/6× C3H/N f1, 4–5 weeks, (Taconic Farms)) and adult fertile females (C57BL/6×C3H/N f1, 2–4 months, (Taconic Farms) as parents.

The donors are injected with approximately 8 IU/mouse of Pregnant Mare's Serum gonadotrophin (Sigma, St. Louis, Mo.) I.P., and 46–47 hours later, 8 IU/mouse of human Chorionic Gonadotropin (hCG (Sigma)) are administered I.P. to induce superovulation. Fertilized eggs are collected and stored in a 37° C./5% $CO_2$ incubator until microinjection.

10–20 micrograms of plasmid DNA containing a cDNA of the zsig81 gene is linearized, gel-purified, and resuspended in 10 mM Tris pH 7.4, 0.25 mM EDTA pH 8.0, at a final concentration of 5–10 nanograms per microliter for microinjection. Plasmid DNA is microinjected into harvested eggs and are penetrated with an injection needle, into one or both of the haploid pronuclei.

The following day 2-cell embryos are transferred into pseudopregnant recipients. The recipients are returned to cages in pairs, and allowed 19–21 days gestation. After birth, 19–21 days postpartum is allowed before weaning. The 25 weanlings are sexed and placed into separate sex cages, and a 0.5 cm biopsy (used for genotyping) is snipped off the tail with clean scissors.

Genomic DNA is prepared from the tail snips using a Qiagen Dneasy kit following the manufacturer's instructions. Genomic DNA is analyzed by PCR using primers designed to the human growth hormone (hGH) 3' UTR portion of the transgenic vector. A region unique to the human sequence is identified from an alignment of the human and mouse growth hormone 3' UTR DNA sequences, ensuring that the PCR reaction does not amplify the mouse sequence. Primers ZC17251 (SEQ ID NO: 14) and ZC17252 (SEQ ID NO: 15) amplify a 368 base pair fragment of hGH.

In addition, primers ZC17156 (SEQ ID NO: 16) and ZC17157 (SEQ ID NO: 17), which hybridize to vector sequences and amplify the cDNA insert, is often used along with the hGH primers. In experiments, DNA from animals positive for the transgene generate two bands, a 368 base pair band corresponding to the hGH 3' UTR fragment and a band of variable size corresponding to the cDNA insert.

Once animals are confirmed to be transgenic (TG), they are bred back with C57B1/6 wild-type mates. As pups are born and weaned, the sexes are separated, and their tails snipped for genotyping.

To check for expression of a transgene in a live animal, a small partial hepatic biopsy is collected. The collected liver biopsy is transferred to a 14 ml polypropylene round bottom tube and snap frozen in liquid nitrogen and then stored on dry ice.

Analysis of the mRNA expression level of each transgene is done using an RNA solution hybridization assay.

Example 10

Bone Marrow Assay of zsig81
A. Isolation of Non-adherent Low Density Marrow Cells:

Fresh mouse femur aspirate (marrow) was obtained from 6–10 week old male Balb/C or C57BL/6 mice. The marrow was then washed with RPMI+10% FBS (JRH, Lenexa Kans.; Hyclone, Logan Utah) and suspended in RPMI+10% FBS as a whole marrow cell suspension. The whole marrow cell suspension was then subjected to a density gradient (Nycoprep, 1.077, Animal; Gibco BRL) to enrich for low density, mostly mononuclear, cells as follows: The whole marrow cell suspension (About 8 ml) was carefully pipeted on top of about 5 ml Nycoprep gradient solution in a 15 ml conical tube, and then centrifuged at 600×g for 20 minutes. The interface layer, containing the low density mononuclear cells, was then removed, washed with excess RPMI+10% FBS, and pelleted by centrifugation at 400×g for 5–10 minutes. This pellet was resuspended in RPMI+10% FBS and plated in a T-75 flask at approximately $10^6$ cells/ml, and incubated at 37° C. 5% $CO_2$ for approximately 2 hours. The resulting cells in suspension were Non-Adherent Low Density (NA LD) Marrow Cells.
B. 96-Well Assay NA LD Mouse Marrow Cells were plated at 25,000 to 45,000 cells/well in 96 well tissue culture plates in RPMI+ 10% FBS+1 ng/mL mouse Stem Cell Factor (mSCF) (R&D Systems, Minneapolis, Minn.), plus 5% conditioned medium from one of the following: (1) 293 cells expressing adenoviral zsig81, or (2) adenovirus infected 293 cells not expressing zsig81. These cells were then subjected to a variety of cytokine treatments to test for expansion or differentiation of hematopoietic cells from the marrow. To test, the plated NA LD mouse marrow cells were subjected to mouse Interleukin 4 (mIL-4), mouse Macrophage-Colony stimulating factor (mM-CSF) (R&D Systems), or one of a panel of other cytokines (R&D Systems). Serial dilution of mIL-4, mM-CSF, or the other cytokines, were tested, with 2-fold serial dilution from about 50 ng/ml down to about 6.25 ng/ml concentration. After 8 to 12 days the 96-well assays were scored for cell proliferation by Alamar blue assay (Accumed, Chicago, Ill.).
C. Mouse Bone Marrow Assays Using Human zSig81.CEE Isolated From Baculovirus.

NA LD mouse bone marrow cells were plated at 200,000 cells/well in 24 well tissue culture dishes. The culture medium was supplemented with 2 ng/mL stem cell factor (R&D systems, Minn., Minn.), plus one of the following: 1)

15 ng/mL murine L4 (R&D systems, Minn., Minn.) 2) 15 ng/mL murine GM-CSF 3) 50 ng/mL human zSig81.CEE 4) nothing 5) 15 ng/mL murine IL-4 (R&D systems, Minn., Minn.) and 50 ng/mL human zSig8I.CEE 6) 15 ng/mL murine GM-CSF (R&D systems, Minn., Minn.) and 50 ng/mL human zSig81.CEE. At day 6 following initiation there was significant outgrowth in cultures containing murine zSig81, IL-4, or GM-CSF alone, or in combination. In addition, cells cultured in the presence zSig81 displayed morphologies that were absent in cultures not containing zSig81.

In another experiment, NA LD mouse bone marrow cells were plated 200,000 cells/well in 24-well tissue culture dishes. The culture medium was supplemented with 2 ng/ml stem cell factor (R&D Systems, Minn. Minn.), plus one of the following: (1) 15 ng/ml murine HL-4 (R&D Systems), (2) 2% conditioned medium (CM) from 293 cells expressing mzSig81, (3) 2% CM from adenovirus infected 293 cells not expressing zsig81, (4) nothing, (5) 15 ng/ml murine IL-4 (R&D Systems) plus 2% CM from 293 cells expressing murine zsig81, (6) 15 ng/ml MIL-4 (R&D Systems) plus 2% CM from adenovirus infected 293 cells. At culture days 4 and 6, the cultures containing zsig81 or IL-4 were much denser than cultures containing SCF or control CM. Furthermore, the cells cultured in the presence of mzsig81 had a different morphology from those cultured in the absence of mzsig81. The cells from cultures (2), (4), (5) and (6) were removed and stained with antibodies against B220 (Pharmingen, San Diego, Calif.) or CD-80 (Pharmingen). There were no B220 positive cells observed in any of the cultures. Cells exposed to mzsig81 were positive for CD-80 and cells not exposed to mzsig81 were negative for CD-80. These data suggest that cells proliferating in the presence of zsig81 are of the dendritic lineage.

Human bone marrow cells were plated at 800,00 cells/well in 12-well culture dishes containing culture medium with 2.5 mg/ml FLT-3 (R&D Systems) and of the following: (1) nothing, (2) hIL-4 (R&D Systems), (3) BHK CM containing hzsig81, (4) BHK CM, (5) hIL-4 (R&D Systems) and BHK CM. At day 12 of culturing, the cells cultured in the presence of IL-4, hzsig81, and hzsig81 plus IL-4, all displayed similar morphologies that were not seen in cultures not exposed to hzsig81 or IL-4. In addition, cultures containing hzsig81 contained more cells. At day 12, the cells were removed and stained antibodies against CD80 (Pharmingen), CD11c (Pharmingen), or HLA-DR (Pharmingen). Cells cultured in the presence of hzsig81 showed increased staining for CD-80, CD11c, and HLA-DR. The increase was equal to that seen for cells cultured in the presence of hIL-4, and was not seen in control cultures containing BHK CM without zsig81 or IL-4. The data suggest that the proliferating cells are dendritic lineage because these markers are found on mature dendritic cells.

Additional evidence that zsig81 targets dendritic cells was seen when iodinated zsig81 was found to bind to an immature dendritic cells line (JAWS II, ATCC No. CRL-1194). The binding was inhibited in a dose dependent manner by unlabeled hzsig81, but not by other cytokines.

Example 11

Mixed Lymphocyte Reaction (MLR)
A. Preparation of Stimulator Cells (Dendritic Cells)

A mouse dendritic cell line, JAWS II (CRL-11904; American Type Culture Collection, 10801 University Boulevard, Manassas, Va. 20110–2209) is grown to high density (1–2×$10^6$ cells/ml) in α-MEM (Minimal Essential Medium, alpha-modification, containing 10% fetal bovine serum (FBS), 1 mM sodium pyruvate, 4 mM glutamine) +5 ng/ml murine GM-CSF. Additional cytokines used to activate the cells include interferon-γ (100 U/ml), tumor necrosis factor-α (10 ng/ml), and interleukin-4 (10 ng/ml). The culture supernatant containing the nonadherent cells is pooled with adherent cells removed by washing with Versene and the cells are resuspended at $3 \times 10^5$ cells/ml in RPMI-1640 medium (containing 10% FBS, 10 mM HEPES, 4 mM glutamine, $5.7 \times 10^{-5}$ M 2-mercaptoethanol, 50 μg/ml gentamycin, 100 U/ml penicillin, 100 μg/ml streptomycin).

Splenic dendritic cells are isolated by the method of Swiggard et al. (*Curr. Protocols Immunol.* 3.7.1–3.7.11, 1992) from spleens of C57B1/6 and BALB/c mice. Briefly, single cell suspensions of spleen cells are generated by digestion with collagenase and a low density fractionation. The low density fraction is obtained by centrifugation of the cells through a low density solution (refractive index of approximately 1.364) of bovine serum albumin (BSA) in phosphate-buffered saline (PBS) onto a high density cushion (refractive index of approximately 1.385) of BSA in PBS and contains primarily dendritic cells, macrophages, and some B cells. Cells are resuspended at 37° C. in RPMI medium at $1 \times 10^7$ cells/ml and 4 ml of the suspension is plated per 60 mm tissue culture plate. After a 90 minute incubation at 37° C., nonadherent cells are gently removed, adherent cells are washed with RPMI, and incubated in RPMI for an additional 30–60 min. Nonadherent cells are again removed and adherent cells gently washed with RPMI and incubated in RPMI for 12–20 hours at 37° C. Splenic dendritic cells detached during the final incubation and are isolated as nonadherent cells. The nonadherent splenic dendritic cells are resuspended in RPMI at $3 \times 10^5$ cells/ml.

JAWS II and splenic dendritic stimulator cells are irradiated for 40 minutes in a $^{137}$Cs irradiator (Gammacell 40, Nordion International Inc., Kanata, Ontario, Canada) at 550 rads/min before use in the MLR.

B. Preparation of Responder Cells (T Cells)

Spleens and lymph nodes are removed from C57B1/6 or BALB/c mice (Jackson Labs, Bar Harbor, Me.). Spleen cell suspensions in BSS-BSA buffer are made by mechanical disruption of the spleen between glass slides. Red blood cells are lysed by resuspending the spleen cell pellet in 0.9 ml dH$_2$O followed quickly by addition of 0.1 ml 10×Lymph node cell suspensions in BSS are made by teasing the nodes with sterile forceps and are pooled with the autologous spleen cell suspension and filtered through nylon cloth filters to remove debris.

The single cell suspension of spleen and lymph node cells is loaded onto a nylon wool column pre-equilibrated at 37° C. with BSS+5% FBS. After incubation at 37° C. for 45 minutes, the T cells are eluted with 37° C. with BSS+5% FBS (12 ml per 1.5 g nylon wool column loaded with approximately $1.5 \times 10^8$ total spleen+lymph node cells). The T cells (usually 80–90% pure) are resuspended in RPMI at $3 \times 10^6$ cells/ml.

C. Incubation Conditions for MLR $3 \times 10^5$ responder cells per well (96-well plate) are mixed in duplicate with increasing numbers of irradiated stimulator cells (usually $3 \times 10^3$, $1 \times 10^4$, $3 \times 10^4$ cells) in a final volume of 200 μl. Controls includes responder cells alone and stimulator cells alone. A syngeneic MLR includes responder and stimulator cells from the same mouse strain (e.g., C57B1/6 or BALB/c), whereas an allogeneic MLR has stimulator cells incubated with responder cells from a different strain (e.g., C57B1/6 or JAWS II stimulator cells with BALB/c responder cells). The MLR cultures are incubated at 37° C. for approximately 72–76 hours before addition of 1 μCi/well ³H-thymidine to assay proliferation of responder cells. Cultures are harvested 16–20 hours later with a Skatron cell harvester (Skatron, Sterling, Va.), and the incorporated ³H-thymidine is determined with a Wallac Betaplate liquid scintillation counter (Pharmacia).

When JAWS II cells are induced with a combination of factors that stimulate allogeneic T cells, the JAWS H cells proliferate. JAWS II cells are induced with TNF-α, IFN-γ, GM-CSF and L-4. In addition, the JAWS II cell line do not stimulate proliferation in syngeneic T cells.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated polypeptide comprising a sequence of amino acid residues that is 95% identical to the amino acid residues as shown in SEQ ID NO:2 from residue 5 to residue 156, and wherein the polypeptide is capable of expanding cells of a dendritic lineage from bone marrow.

2. The isolated polypeptide of claim 1, wherein the cells are positive for markers selected from the group consisting of CD-80, CD11c, and HFA-DR.

3. The isolated polypeptide of claim 1, wherein the sequence of amino acids is 95% identical to the amino acid residues as shown in SEQ ID NO:2 from residue 1 to residue 156.

4. The isolated polypeptide of claim 1, wherein the sequence of amino acids is 95% identical to the amino acid residues as shown in SEQ ID NO:2 from residue −17 to residue 156.

5. An isolated polypeptide comprising a sequence of amino acid residues as shown in SEQ ID NO:2 from residue 5 to residue 156.

6. The isolated polypeptide of claim 5, wherein the polypeptides comprises residues 1 to 156.

7. The isolated polypeptide of claim 5, wherein the polypeptide comprises residues −17 to 156.

8. The isolated polypeptide of claim 5, wherein the polypeptide is capable of expanding cells of a dendritic lineage from bone marrow.

9. The isolated polypeptide of claim 5, wherein the cells are positive for markers selected from the group consisting of CD-80, CD11c, and HFA-DR.

* * * * *

SEQUENCE LISTING

<160> NUMBER OF SEQ ID NOS: 36

<210> SEQ ID NO 1
<211> LENGTH: 1600
<212> TYPE: DNA
<213> ORGANISM: Homo sapiens
<220> FEATURE:
<221> NAME/KEY: CDS
<222> LOCATION: (134)...(655)
<221> NAME/KEY: sig_peptide
<222> LOCATION: (134)...(184)

<400> SEQUENCE: 1

```
gaattcggct cgaggcaaaa ggaagggagg gaagcactcc atcatctcac tgggaagaac      60
ggcacgggca tacctgcagc tactggggtt ccactgggct tgaggtcga ttttcacct     120 tttgaaggac aag atg cat tgg aag atg ttg ctg ctt ctg ctg ttg tat      169
            Met His Trp Lys Met Leu Leu Leu Leu Leu Tyr
                -15                    -10 tac aat gct gag gct tct atg tgc cac agg tgg agc agg gct gtg ctc      217
Tyr Asn Ala Glu Ala Ser Met Cys His Arg Trp Ser Arg Ala Val Leu
 -5              1               5                      10 ttc cct gcc gcc cac cgg cca aag agg tcc tca tca ctg cca ttg aac      265
Phe Pro Ala Ala His Arg Pro Lys Arg Ser Ser Ser Leu Pro Leu Asn
             15                  20                      25 cca gtc ctg cag acc tcc ctg gag gag gtg gag ctg ctc tac gag ttc      313
Pro Val Leu Gln Thr Ser Leu Glu Glu Val Glu Leu Leu Tyr Glu Phe
             30                  35                      40 ctg ctg gcc gaa ctt gag atc agc cct gac ctg cag atc tcc atc aag      361
Leu Leu Ala Glu Leu Glu Ile Ser Pro Asp Leu Gln Ile Ser Ile Lys
    45                   50                  55 gac gag gag ctg gcc tcc ttg cgg aag gcc tca gac ttc cgc acc gtc      409
Asp Glu Glu Leu Ala Ser Leu Arg Lys Ala Ser Asp Phe Arg Thr Val
 60              65                   70                      75 tgc aac aac gtc atc ccc aag agc atc cca gac atc cgc cgg ctc agc      457
Cys Asn Asn Val Ile Pro Lys Ser Ile Pro Asp Ile Arg Arg Leu Ser
             80                  85                      90 gcc agc ctc tcc agc cac cct ggc atc ctc aag aaa gaa gac ttt gaa      505
Ala Ser Leu Ser Ser His Pro Gly Ile Leu Lys Lys Glu Asp Phe Glu
             95                  100                     105 agg aca gtg ctg acc ctg gcc tac aca gcc tac cgc aca gcc ctg tcc      553
Arg Thr Val Leu Thr Leu Ala Tyr Thr Ala Tyr Arg Thr Ala Leu Ser
        110                  115                     120 cac ggc cat cag aag gac atc tgg gcg cag tcc ctc gtt agc ctc ttc      601
His Gly His Gln Lys Asp Ile Trp Ala Gln Ser Leu Val Ser Leu Phe
    125                  130                     135 cag gcc ctg agg cac gac ttg atg cgc tcc tca cag ccg gga gta cct      649
Gln Ala Leu Arg His Asp Leu Met Arg Ser Ser Gln Pro Gly Val Pro
140                  145                     150                 155 ccc tga gagactggcc cacaccagga cctcagagca gggaccagca cagtaatcca      705
Pro
```

-continued

```
gaaagtcttc attctctact ccatttacag agaccagcaa caaaacactt accgctgaca      765
cagagcagca gagatcaaac agtaaccccg atgctctttt ctccttgtag tttcctggaa      825
gacacatctg attcatgcca tcatgtgacc tgggctggaa gaaagggctg gaatggtcat      885
tcaagacgcc tccatgggca gaatggtttg cctatggcag gcagaattct gatatgcttc      945
aacccagagc agtggccaca cactcaagag tgagaacagg cgtgagccac cgtgcctggc     1005
ccaggatcta aaaactttct aagtttcctc catcgttggc atcctcacag ctatctccaa     1065
tgtcactcaa gagacatcaa cagacattta actgctgcag acttcattgc tctgtcacct     1125
caccttgaat ctaacaaatc aaagtatttc tgcaggtcca atggtctaaa atcaaatgct     1185
tgttaaatga cttttacaa cacccttac tttcctaatc catttcaatc ttatttttt       1245 tattgtggta aaaacacat cacgtaaaat gtaccatctt aaccattttt aagcatatgg      1305
tacagcagtg ttaactccat gcatgttgtg aaacagaccc ccggaacttt ctcatcttgt     1365
aattctgaag ttctataccc accgaacaac tcctctttc cccttccccc tgcctgcccc      1425
agctcttggc accattattc tgctttctgt ttttgagagt ctgactactt aagatacctc     1485
atacaagcgg gatctggctt acatttcttg agcattgtat tctggaaaag tgtttccttc     1545
ctctgaaaaa tgggtagagt tctgaaggag aactactggt cttattgtac acttg         1600
```

<210> SEQ ID NO 2
<211> LENGTH: 173
<212> TYPE: PRT
<213> ORGANISM: Homo sapiens
<220> FEATURE:
<221> NAME/KEY: SIGNAL
<222> LOCATION: (1)...(17)

<400> SEQUENCE: 2

```
Met His Trp Lys Met Leu Leu Leu Leu Tyr Tyr Asn Ala Glu
        -15                 -10                 -5

Ala Ser Met Cys His Arg Trp Ser Arg Ala Val Leu Phe Pro Ala Ala
  1               5                  10                  15

His Arg Pro Lys Arg Ser Ser Ser Leu Pro Leu Asn Pro Val Leu Gln
                 20                  25                  30

Thr Ser Leu Glu Glu Val Glu Leu Leu Tyr Glu Phe Leu Leu Ala Glu
             35                  40                  45

Leu Glu Ile Ser Pro Asp Leu Gln Ile Ser Ile Lys Asp Glu Glu Leu
         50                  55                  60

Ala Ser Leu Arg Lys Ala Ser Asp Phe Arg Thr Val Cys Asn Asn Val
     65                  70                  75

Ile Pro Lys Ser Ile Pro Asp Ile Arg Arg Leu Ser Ala Ser Leu Ser
 80                  85                  90                  95

Ser His Pro Gly Ile Leu Lys Lys Glu Asp Phe Glu Arg Thr Val Leu
                100                 105                 110

Thr Leu Ala Tyr Thr Ala Tyr Arg Thr Ala Leu Ser His Gly His Gln
            115                 120                 125

Lys Asp Ile Trp Ala Gln Ser Leu Val Ser Leu Phe Gln Ala Leu Arg
        130                 135                 140

His Asp Leu Met Arg Ser Ser Gln Pro Gly Val Pro Pro
    145                 150                 155
```

<210> SEQ ID NO 3
<211> LENGTH: 1547
<212> TYPE: DNA
<213> ORGANISM: Mus musculus

```
<220> FEATURE:
<221> NAME/KEY: CDS
<222> LOCATION: (212)...(733)
<221> NAME/KEY: sig_peptide
<222> LOCATION: (212)...(262)

<400> SEQUENCE: 3
ggattcggca cgagggagag gtaccaactt ctgtcccacc caagaggctg catccgcctc      60
catcctgtgg agccagggag aggcccttgc tttccttata gacaagaaag ggcagtaaga    120
actctgtcct ctcgctgaga agagcagggg tccacctgca gccctggggg tcccgcagga    180
atagaaggtc agcttgtctc cctcctggaa g atg tcc tgg aag gcg ctg acg      232
                                   Met Ser Trp Lys Ala Leu Thr
                                                         -15 att ctg ctg gta ttc tcc agc acc cag gcc act gcg tcc tgc agg tgg      280
Ile Leu Leu Val Phe Ser Ser Thr Gln Ala Thr Ala Ser Cys Arg Trp
-10              -5                   1                 5 agc agg gcc gca ctg ttc cca gct gcc cat cgg cca aag agg tcc ttg      328
Ser Arg Ala Ala Leu Phe Pro Ala Ala His Arg Pro Lys Arg Ser Leu
             10              15              20 tca ctg cca ttg aat cca gtc ctg cag acc tcc ctg gag gag gtg gaa      376
Ser Leu Pro Leu Asn Pro Val Leu Gln Thr Ser Leu Glu Glu Val Glu
         25              30              35 ctg ctg tat gag ctc ttg cta gct gaa att gag atc agc cca gac ctg      424
Leu Leu Tyr Glu Leu Leu Leu Ala Glu Ile Glu Ile Ser Pro Asp Leu
     40              45              50 gag atc tcc atc aag gac gag gag cta gct tcc ctg cgg aag gcc ttg      472
Glu Ile Ser Ile Lys Asp Glu Glu Leu Ala Ser Leu Arg Lys Ala Leu
 55              60              65              70 agt ttc cac tca atc tgc aat aac ata atc ccc aag cgt atc cca gat      520
Ser Phe His Ser Ile Cys Asn Asn Ile Ile Pro Lys Arg Ile Pro Asp
                 75              80              85 atc cga agg ctg agt gcc aac ctg gca aac cac cct gga atc ctc aag      568
Ile Arg Arg Leu Ser Ala Asn Leu Ala Asn His Pro Gly Ile Leu Lys
             90              95             100 aaa gaa gac ttt gag agg ata aca tta acc ctg gcg tac aca gcc tat      616
Lys Glu Asp Phe Glu Arg Ile Thr Leu Thr Leu Ala Tyr Thr Ala Tyr
         105             110             115 cgg aca gcc tta tct gaa ggg cat cag aag gac atc tgg gct cag tcc      664
Arg Thr Ala Leu Ser Glu Gly His Gln Lys Asp Ile Trp Ala Gln Ser
     120             125             130 ctc atc agc cta ttc cag gcc ctg agg cat gac ttg atg cgg tcc tcg      712
Leu Ile Ser Leu Phe Gln Ala Leu Arg His Asp Leu Met Arg Ser Ser
135             140             145             150 agc cct gct gtg tca tcc tga gagaatggct catgctagaa ctttgaagca         763
Ser Pro Ala Val Ser Ser
                155 ggaacaggca cacacagtct tctagaactt tcatcctcta ctgcactttc agagaaaagt    823 atatacttcc cacacagaat agcaaagata aatgagtcac cccaatattt tttgtccctt    883 gttgcttcca gacagacata tccgacctat gttataatgt tacctgagaa aaggctagac    943 tggactttca agatgcctcc agaggccaac tggtctacct ggtaatgagc agacttctga   1003 gatatactta cacacatacc caagagtagg gactgaggat ggagtctgag catggcagga   1063 ggatggtggg cagattcctt tggttctaag ggatctgtgt tgaatgaata ttttctggca   1123 ggttctatgg taaatataaa aaaggcagag atgcattcaa attaatatgc tattagccaa   1183 gaaggatata cttggcttgc cccaaagcca tgaagaagac tctgtatttt ggtgacctac   1243 ttgacttggt ggaaatgcta gcagtccacc catgccctat catttcaatg tagaagccag   1303
```

-continued

```
gctaaagcat agtgccttcc taatgaaaga ggtaacacca ctatgcgtgt ttttcctaaa    1363
ataccatagc actgtcagcg acttgggtgc tcctaaaaaa attcgctttc agatgacaga    1423
ttgtttacct ttcaaatgct gatttttttt ctttcaaaat gttagtttga tatctgttca    1483
ttatttatat taaatactgg ttgatattta aaaaaaaaaa aaaaaaaaaa accattgcgg    1543
ccgc                                                                 1547
```

<210> SEQ ID NO 4
<211> LENGTH: 173
<212> TYPE: PRT
<213> ORGANISM: Mus musculus
<220> FEATURE:
<221> NAME/KEY: SIGNAL
<222> LOCATION: (1)...(17)

<400> SEQUENCE: 4

```
Met Ser Trp Lys Ala Leu Thr Ile Leu Leu Val Phe Ser Ser Thr Gln
     -15                 -10                 -5
Ala Thr Ala Ser Cys Arg Trp Ser Arg Ala Ala Leu Phe Pro Ala Ala
      1               5                  10                  15
His Arg Pro Lys Arg Ser Leu Ser Leu Pro Leu Asn Pro Val Leu Gln
                 20                  25                  30
Thr Ser Leu Glu Glu Val Glu Leu Leu Tyr Glu Leu Leu Ala Glu
             35                  40                  45
Ile Glu Ile Ser Pro Asp Leu Glu Ile Ser Ile Lys Asp Glu Leu
         50                  55                  60
Ala Ser Leu Arg Lys Ala Leu Ser Phe His Ser Ile Cys Asn Asn Ile
 65                  70                  75
Ile Pro Lys Arg Ile Pro Asp Ile Arg Arg Leu Ser Ala Asn Leu Ala
 80                  85                  90                  95
Asn His Pro Gly Ile Leu Lys Lys Glu Asp Phe Glu Arg Ile Thr Leu
                100                 105                 110
Thr Leu Ala Tyr Thr Ala Tyr Arg Thr Ala Leu Ser Glu Gly His Gln
             115                 120                 125
Lys Asp Ile Trp Ala Gln Ser Leu Ile Ser Leu Phe Gln Ala Leu Arg
         130                 135                 140
His Asp Leu Met Arg Ser Ser Ser Pro Ala Val Ser Ser
         145                 150                 155
```

<210> SEQ ID NO 5
<211> LENGTH: 519
<212> TYPE: DNA
<213> ORGANISM: Artificial Sequence
<220> FEATURE:
<223> OTHER INFORMATION: Degenerate sequence derived from human zsig81
    protein sequence
<220> FEATURE:
<221> NAME/KEY: misc_feature
<222> LOCATION: (1)...(519)
<223> OTHER INFORMATION: n = A,T,C or G

<400> SEQUENCE: 5

```
atgcaytgga aratgytnyt nytnytnytn ytntaytaya aygcngargc nwsnatgtgy     60
caymgntggw snmgngcngt nytnttyccn gcngcncaym gnccnaarmg nwsnwsnwsn    120
ytnccnytna ayccngtnyt ncaracnwsn ytngargarg tngarytnyt ntaygartty    180
ytnytngcng arytngarat hwsnccngay ytncarathw snathaarga ygargarytn    240
gcnwsnytnm gnaargcnws ngayttymgn acngtntgya ayaaygtnat hccnaarwsn    300
```

```
athccngaya thmgnmgnyt nwsngcnwsn ytnwsnwsnc ayccnggnat hytnaaraar      360
gargayttyg armgnacngt nytnacnytn gcntayacng cntaymgnac ngcnytnwsn      420
cayggncayc araargayat htgggcncar wsnytngtnw snytnttyca rgcnytnmgn      480
caygayytna tgmgnwsnws ncarccnggn gtnccnccn                            519
```

```
<210> SEQ ID NO 6
<211> LENGTH: 15
<212> TYPE: PRT
<213> ORGANISM: Artificial Sequence
<220> FEATURE:
<223> OTHER INFORMATION: variant derived from human helix A
<220> FEATURE:
<221> NAME/KEY: VARIANT
<222> LOCATION: (1)...(1)
<223> OTHER INFORMATION: Xaa = Ala, Ile or Leu
<220> FEATURE:
<221> NAME/KEY: VARIANT
<222> LOCATION: (4)...(4)
<223> OTHER INFORMATION: Xaa = Met, Gly, Ala, Thr or Ser
<220> FEATURE:
<221> NAME/KEY: VARIANT
<222> LOCATION: (5)...(11)
<223> OTHER INFORMATION: Xaa = Val, Ile or Leu
<220> FEATURE:
<221> NAME/KEY: VARIANT
<222> LOCATION: (12)...(12)
<223> OTHER INFORMATION: Xaa = Tyr, Phe or Trp
<220> FEATURE:
<221> NAME/KEY: VARIANT
<222> LOCATION: (15)...(15)
<223> OTHER INFORMATION: Xaa = Leu, Ile or Val

<400> SEQUENCE: 6

Xaa Gln Thr Xaa Xaa Glu Glu Xaa Glu Leu Xaa Xaa Glu Phe Xaa
 1               5                  10                  15

<210> SEQ ID NO 7
<211> LENGTH: 15
<212> TYPE: PRT
<213> ORGANISM: Artificial Sequence
<220> FEATURE:
<223> OTHER INFORMATION: variant derived from human helix B
<220> FEATURE:
<221> NAME/KEY: VARIANT
<222> LOCATION: (1)...(1)
<223> OTHER INFORMATION: Xaa = Val, Leu or Ile
<220> FEATURE:
<221> NAME/KEY: VARIANT
<222> LOCATION: (4)...(4)
<223> OTHER INFORMATION: Xaa = Arg, His or Lys
<220> FEATURE:
<221> NAME/KEY: VARIANT
<222> LOCATION: (5)...(5)
<223> OTHER INFORMATION: Xaa = Glu or Asp
<220> FEATURE:
<221> NAME/KEY: VARIANT
<222> LOCATION: (8)...(11)
<223> OTHER INFORMATION: Xaa = Val, Ile or Leu
<220> FEATURE:
<221> NAME/KEY: VARIANT
<222> LOCATION: (12)...(12)
<223> OTHER INFORMATION: Xaa = Arg, Lys or His
<220> FEATURE:
<221> NAME/KEY: VARIANT
<222> LOCATION: (15)...(15)
<223> OTHER INFORMATION: Xaa = Ser, Gly, Ala, Thr or Met

<400> SEQUENCE: 7

Xaa Ser Ile Xaa Xaa Glu Glu Xaa Ala Ser Xaa Xaa Lys Ala Xaa
 1               5                  10                  15
```

```
<210> SEQ ID NO 8
<211> LENGTH: 9
<212> TYPE: PRT
<213> ORGANISM: Artificial Sequence
<220> FEATURE:
<223> OTHER INFORMATION: variant derived from human helix C
<220> FEATURE:
<221> NAME/KEY: VARIANT
<222> LOCATION: (2)...(5)
<223> OTHER INFORMATION: Xaa = Val, Ile or Leu
<220> FEATURE:
<221> NAME/KEY: VARIANT
<222> LOCATION: (6)...(6)
<223> OTHER INFORMATION: Xaa = Ser, Met, Gly, Ala or Thr
<220> FEATURE:
<221> NAME/KEY: VARIANT
<222> LOCATION: (9)...(9)
<223> OTHER INFORMATION: Xaa = Leu, Val or Ile

<400> SEQUENCE: 8

Asp Xaa Arg Arg Xaa Xaa Ala Ser Xaa
 1               5

<210> SEQ ID NO 9
<211> LENGTH: 15
<212> TYPE: PRT
<213> ORGANISM: Artificial Sequence
<220> FEATURE:
<223> OTHER INFORMATION: variant derived from human helix D
<220> FEATURE:
<221> NAME/KEY: VARIANT
<222> LOCATION: (1)...(4)
<223> OTHER INFORMATION: Xaa = Val, Ile or Leu
<220> FEATURE:
<221> NAME/KEY: VARIANT
<222> LOCATION: (5)...(5)
<223> OTHER INFORMATION: Xaa = Tyr, Trp or Phe
<220> FEATURE:
<221> NAME/KEY: VARIANT
<222> LOCATION: (8)...(8)
<223> OTHER INFORMATION: Xaa = Val, Ile or Leu
<220> FEATURE:
<221> NAME/KEY: VARIANT
<222> LOCATION: (11)...(11)
<223> OTHER INFORMATION: Xaa = Asp or Glu
<220> FEATURE:
<221> NAME/KEY: VARIANT
<222> LOCATION: (12)...(12)
<223> OTHER INFORMATION: Xaa = Leu, Val or Ile
<220> FEATURE:
<221> NAME/KEY: VARIANT
<222> LOCATION: (15)...(15)
<223> OTHER INFORMATION: Xaa = Ser, Gly, Met, Ala or Thr

<400> SEQUENCE: 9

Xaa Val Ser Xaa Xaa Gln Ala Xaa Arg His Xaa Xaa Met Arg Xaa
 1               5                  10                  15

<210> SEQ ID NO 10
<211> LENGTH: 22
<212> TYPE: DNA
<213> ORGANISM: Artificial Sequence
<220> FEATURE:
<223> OTHER INFORMATION: oligonucleotide primer ZC21621

<400> SEQUENCE: 10
gggctgtgcg gtaggctgtg ta                                          22

<210> SEQ ID NO 11
<211> LENGTH: 22
<212> TYPE: DNA
<213> ORGANISM: Artificial Sequence
```

```
<220> FEATURE:
<223> OTHER INFORMATION: oligonucleotide primer ZC21622

<400> SEQUENCE: 11
aagaacggca cgggcatacc tg                                          22

<210> SEQ ID NO 12
<211> LENGTH: 18
<212> TYPE: DNA
<213> ORGANISM: Artificial Sequence
<220> FEATURE:
<223> OTHER INFORMATION: oligonucleotide primer ZC22801

<400> SEQUENCE: 12
aacggcacgg gcatacct                                               18

<210> SEQ ID NO 13
<211> LENGTH: 18
<212> TYPE: DNA
<213> ORGANISM: Artificial Sequence
<220> FEATURE:
<223> OTHER INFORMATION: oligonucleotide primer ZC22802

<400> SEQUENCE: 13
gaagcctcag cattgtaa                                               18

<210> SEQ ID NO 14
<211> LENGTH: 25
<212> TYPE: DNA
<213> ORGANISM: Artificial Sequence
<220> FEATURE:
<223> OTHER INFORMATION: oligonucleotide primer ZC17251

<400> SEQUENCE: 14
tctggacgtc ctcctgctgg tatag                                       25

<210> SEQ ID NO 15
<211> LENGTH: 25
<212> TYPE: DNA
<213> ORGANISM: Artificial Sequence
<220> FEATURE:
<223> OTHER INFORMATION: oligonucleotide primer ZC17252

<400> SEQUENCE: 15
ggtatggagc aagggggcaag ttggg                                      25

<210> SEQ ID NO 16
<211> LENGTH: 27
<212> TYPE: DNA
<213> ORGANISM: Artificial Sequence
<220> FEATURE:
<223> OTHER INFORMATION: oligonucleotide primer ZC17156

<400> SEQUENCE: 16
gagtggcaac ttccagggcc aggagag                                     27

<210> SEQ ID NO 17
<211> LENGTH: 27
<212> TYPE: DNA
<213> ORGANISM: Artificial Sequence
<220> FEATURE:
<223> OTHER INFORMATION: oligonucleotide primer ZC17157

<400> SEQUENCE: 17
cttttgctag cctcaaccct gactatc                                     27
```

<210> SEQ ID NO 18
<211> LENGTH: 18
<212> TYPE: DNA
<213> ORGANISM: Artificial Sequence
<220> FEATURE:
<223> OTHER INFORMATION: oligonucleotide primer ZC21229

<400> SEQUENCE: 18
ggccagcaga acgaagca                                                18

<210> SEQ ID NO 19
<211> LENGTH: 18
<212> TYPE: DNA
<213> ORGANISM: Artificial Sequence
<220> FEATURE:
<223> OTHER INFORMATION: oligonucleotide primer ZC21711

<400> SEQUENCE: 19
cctgcctgcc gtttcttc                                                18

<210> SEQ ID NO 20
<211> LENGTH: 8
<212> TYPE: PRT
<213> ORGANISM: Artificial Sequence
<220> FEATURE:
<223> OTHER INFORMATION: FLAG peptide tag

<400> SEQUENCE: 20

Asp Tyr Lys Asp Asp Asp Asp Lys
 1               5

<210> SEQ ID NO 21
<211> LENGTH: 31
<212> TYPE: DNA
<213> ORGANISM: Artificial Sequence
<220> FEATURE:
<223> OTHER INFORMATION: oligonucleotide primer ZC26461

<400> SEQUENCE: 21
tcagtcgtcc ggaaggtgga gcagggctgt g                                 31

<210> SEQ ID NO 22
<211> LENGTH: 52
<212> TYPE: DNA
<213> ORGANISM: Artificial Sequence
<220> FEATURE:
<223> OTHER INFORMATION: oligonucleotide primer ZC26475

<400> SEQUENCE: 22
cgactgatct agactagtcc atcggcatgt attcgggagg tactcccggc tg          52

<210> SEQ ID NO 23
<211> LENGTH: 17
<212> TYPE: DNA
<213> ORGANISM: Artificial Sequence
<220> FEATURE:
<223> OTHER INFORMATION: oligonucleotide primer ZC2359

<400> SEQUENCE: 23
agggacctga gcgagtc                                                 17

<210> SEQ ID NO 24
<211> LENGTH: 33
<212> TYPE: DNA
<213> ORGANISM: Artificial Sequence
<220> FEATURE:

<223> OTHER INFORMATION: oligonucleotide primer ZC12581

<400> SEQUENCE: 24
tcgagctact tatcgtcatc gtccttatag tcg    33

<210> SEQ ID NO 25
<211> LENGTH: 27
<212> TYPE: DNA
<213> ORGANISM: Artificial Sequence
<220> FEATURE:
<223> OTHER INFORMATION: oligonucleotide primer ZC23433

<400> SEQUENCE: 25
ctccggatcc atgtcctgga aggcgct    27

<210> SEQ ID NO 26
<211> LENGTH: 31
<212> TYPE: DNA
<213> ORGANISM: Artificial Sequence
<220> FEATURE:
<223> OTHER INFORMATION: oligonucleotide primer ZC23432

<400> SEQUENCE: 26
gcatgagcca tctagacagg atgacacagc a    31

<210> SEQ ID NO 27
<211> LENGTH: 17
<212> TYPE: DNA
<213> ORGANISM: Artificial Sequence
<220> FEATURE:
<223> OTHER INFORMATION: oligonucleotide primer ZC447

<400> SEQUENCE: 27
taacaatttc acacagg    17

<210> SEQ ID NO 28
<211> LENGTH: 18
<212> TYPE: DNA
<213> ORGANISM: Artificial Sequence
<220> FEATURE:
<223> OTHER INFORMATION: oligonucleotide primer ZC976

<400> SEQUENCE: 28
cgttgtaaaa cgacggcc    18

<210> SEQ ID NO 29
<211> LENGTH: 1635
<212> TYPE: DNA
<213> ORGANISM: Homo sapiens

<400> SEQUENCE: 29
atgaaaatcg aagaaggtaa actggtaatc tggattaacg gcgataaagg ctataacggt     60
ctcgctgaag tcggtaagaa attcgagaaa gataccggaa ttaaagtcac cgttgagcat    120
ccggataaac tggaagagaa attcccacag gttgcggcaa ctggcgatgg ccctgacatt    180
atcttctggg cacacgaccg ctttggtggc tacgctcaat ctggcctgtt ggctgaaatc    240
accccggaca aagcgttcca ggacaagctg tatcgtttta ctgggatgc cgtacgttac    300 aacggcaagc tgattgctta cccgatcgct gttgaagcgt tatcgctgat ttataacaaa    360
gatctgctgc cgaacccgcc aaaaacctgg aagagatcc cggcgctgga taaagaactg    420
aaagcgaaag gtaagagcgc gctgatgttc aacctgcaag aaccgtactt cacctggccg    480
ctgattgctg ctgacggggg ttatgcgttc aagtatgaaa acggcaagta cgacattaaa    540

```
gacgtgggcg tggataacgc tggcgcgaaa gcgggtctga ccttcctggt tgacctgatt      600
aaaaacaaac acatgaatgc agacaccgat tactccatcg cagaagctgc ctttaataaa      660
ggcgaaacag cgatgaccat caacggcccg tgggcatggt ccaacatcga caccagcaaa      720
gtgaattatg gtgtaacggt actgccgacc ttcaagggtc aaccatccaa accgttcgtt      780
ggcgtgctga gcgcaggtat taacgccgcc agtccgaaca aagagctggc aaaagagttc      840
ctcgaaaact atctgctgac tgatgaaggt ctggaagcgg ttaataaaga caaaccgctg      900
ggtgccgtag cgctgaagtc ttacgaggaa gagttggcga agatccacg tattgccgcc       960 accatggaaa acgcccagaa aggtgaaatc atgccgaaca tcccgcagat gtccgctttc     1020
tggtatgccg tgcgtactgc ggtgatcaac gccgccagcg tcgtcagac tgtcgatgaa      1080 gccctgaaag acgcgcagac taattcgagc tcccaccatc accatcacca cgcgaattcg     1140
gtaccgctgg ttccgcgtgg atcctctatg tgccacaggt ggagcagggc tgtgctcttc     1200
cctgccgccc accggccaaa gaggtcctca tcactgccat tgaacccagt cctgcagacc     1260
tccctggagg aggtggagct gctctacgag ttcctgctgg ccgaacttga gatcagccct     1320
gacctgcaga tctccatcaa ggacgaggag ctggcctcct tgcggaaggc ctcagacttc     1380
cgcaccgtct gcaacaacgt catccccaag agcatcccag acatccgccg gctcagcgcc     1440
agcctctcca gccaccctgg catcctcaag aaagaagact ttgaaaggac agtgctgacc     1500
ctggcctaca cagcctaccg cacagccctg tcccacggcc atcagaagga catctgggcg     1560
cagtccctcg ttagcctctt ccaggccctg aggcacgact tgatgcgctc ctcacagccg     1620
ggagtacctc cctga                                                     1635

<210> SEQ ID NO 30
<211> LENGTH: 64
<212> TYPE: DNA
<213> ORGANISM: Artificial Sequence
<220> FEATURE:
<223> OTHER INFORMATION: oligonucleotide primer ZC22990

<400> SEQUENCE: 30
tcaccacgcg aattcggtac cgctggttcc gcgtggatcc tctatgtgcc acaggtggag      60
cagg                                                                  64

<210> SEQ ID NO 31
<211> LENGTH: 61
<212> TYPE: DNA
<213> ORGANISM: Artificial Sequence
<220> FEATURE:
<223> OTHER INFORMATION: oligonucleotide primer ZC22991

<400> SEQUENCE: 31
tctgtatcag gctgaaaatc ttatctcatc cgccaaaaca tcaggaggt actcccggct       60 g                                                                     61

<210> SEQ ID NO 32
<211> LENGTH: 40
<212> TYPE: DNA
<213> ORGANISM: Artificial Sequence
<220> FEATURE:
<223> OTHER INFORMATION: oligonucleotide primer ZC19372

<400> SEQUENCE: 32
tgtcgatgaa gccctgaaag acgcgcagac taattcgagc                           40
```

```
<210> SEQ ID NO 33
<211> LENGTH: 60
<212> TYPE: DNA
<213> ORGANISM: Artificial Sequence
<220> FEATURE:
<223> OTHER INFORMATION: oligonucleotide primer ZC19351

<400> SEQUENCE: 33
acgcgcagac taattcgagc tcccaccatc accatcacca cgcgaattcg gtaccgctgg      60

<210> SEQ ID NO 34
<211> LENGTH: 60
<212> TYPE: DNA
<213> ORGANISM: Artificial Sequence
<220> FEATURE:
<223> OTHER INFORMATION: oligonucleotide primer ZC19352

<400> SEQUENCE: 34
actcactata gggcgaattg cccgggggat ccacgcggaa ccagcggtac cgaattcgcg      60

<210> SEQ ID NO 35
<211> LENGTH: 42
<212> TYPE: DNA
<213> ORGANISM: Artificial Sequence
<220> FEATURE:
<223> OTHER INFORMATION: oligonucleotide primer ZC19371

<400> SEQUENCE: 35
acggccagtg aattgtaata cgactcacta tagggcgaat tg                        42

<210> SEQ ID NO 36
<211> LENGTH: 5
<212> TYPE: PRT
<213> ORGANISM: Artificial Sequence
<220> FEATURE:
<223> OTHER INFORMATION: Glu Glu peptide tag

<400> SEQUENCE: 36

Glu Tyr Pro Met Glu
 1               5
```